(12) United States Patent
Wilson et al.

(10) Patent No.: US 9,410,873 B2
(45) Date of Patent: Aug. 9, 2016

(54) FLUIDICS APPARATUS FOR SURFACE ACOUSTIC WAVE MANIPULATION OF FLUID SAMPLES, USE OF FLUIDICS APPARATUS AND PROCESS FOR THE MANUFACTURE OF FLUIDICS APPARATUS

(75) Inventors: Rab Wilson, Glasgow (GB); Jonathan M. Cooper, Glasgow (GB); Julien Reboud, Glasgow (GB)

(73) Assignee: The University Court of the University of Glasgow (GB)

( * ) Notice: Subject to any disclaimer, the term of this patent is extended or adjusted under 35 U.S.C. 154(b) by 0 days.

(21) Appl. No.: 14/000,958

(22) PCT Filed: Feb. 24, 2012

(86) PCT No.: PCT/GB2012/000192
§ 371 (c)(1),
(2), (4) Date: Aug. 22, 2013

(87) PCT Pub. No.: WO2012/114076
PCT Pub. Date: Aug. 30, 2012

(65) Prior Publication Data
US 2013/0330247 A1    Dec. 12, 2013

(30) Foreign Application Priority Data

Feb. 24, 2011 (GB) .................................. 1103211.7

(51) Int. Cl.
*G01N 1/00* (2006.01)
*G01N 1/28* (2006.01)
(Continued)

(52) U.S. Cl.
CPC ............ *G01N 1/286* (2013.01); *B01L 3/50273* (2013.01); *B01L 3/502707* (2013.01);
(Continued)

(58) Field of Classification Search
None
See application file for complete search history.

(56) References Cited

U.S. PATENT DOCUMENTS 4,336,514 A * 6/1982 Paige .............................. 333/195
5,455,178 A * 10/1995 Fattinger ....................... 436/164
(Continued)

FOREIGN PATENT DOCUMENTS

CN    1455985       11/2003
CN    2744401 Y    12/2005
(Continued)

OTHER PUBLICATIONS

Allison, et al. (2008) AIAA Journal of Propulsion and Power 24:547-553, "Ultrasonic Propulsion".
(Continued)

*Primary Examiner* — Jennifer Wecker
(74) *Attorney, Agent, or Firm* — Swanson & Bratschun, L.L.C.

(57) ABSTRACT

A fluidics apparatus for manipulation of at least one fluid sample is disclosed. A manipulation surface locates the fluid sample. A surface acoustic wave (SAW) generation material layer is provided. This is a polycrystalline material, textured polycrystalline material, biaxially textured polycrystalline material, microcrystalline material, nanocrystalline material, amorphous material or composite material. A transducer electrode structure arranged at the SAW generation material layer provides SAWs at the manipulation surface for interaction with the fluid sample. The manipulation surface has a phononic structure, for affecting the transmission, distribution and/or behavior of SAWs at the manipulation surface. The apparatus is typically manufactured by reel-to-reel processes, to reduce the unit cost to a level at which the apparatus can be considered to be disposable after a single use.

14 Claims, 27 Drawing Sheets

(51) Int. Cl.
*G01N 29/22* (2006.01)
*B06B 1/00* (2006.01)
*B01L 3/00* (2006.01)

(52) U.S. Cl.
CPC ......... *G01N29/222* (2013.01); *B01L 3/502792* (2013.01); *B01L 2200/10* (2013.01); *B01L 2300/0816* (2013.01); *B01L 2400/0436* (2013.01); *B01L 2400/0439* (2013.01); *B01L 2400/0496* (2013.01); *G01N 2291/0423* (2013.01)

(56) References Cited

U.S. PATENT DOCUMENTS

| | | | |
|---|---|---|---|
| 5,906,549 | A | 5/1999 | Kubica |
| 6,210,128 | B1 | 4/2001 | Rife |
| 6,362,543 | B1 * | 3/2002 | Ellis ............... 310/26 |
| 6,459,080 | B1 | 10/2002 | Yin |
| 6,568,052 | B1 | 5/2003 | Rife |
| 6,603,118 | B2 | 8/2003 | Ellson |
| 6,707,038 | B2 | 3/2004 | Ellson |
| 6,710,335 | B2 | 3/2004 | Ellson |
| 6,739,531 | B2 | 5/2004 | Taylor |
| 6,777,245 | B2 | 8/2004 | Wixforth |
| 6,809,315 | B2 | 10/2004 | Ellson |
| 6,855,925 | B2 | 2/2005 | Ellson |
| 7,103,949 | B2 | 9/2006 | Rife |
| 7,172,897 | B2 | 2/2007 | Blackburn |
| 7,405,395 | B2 | 7/2008 | Ellson |
| 7,459,304 | B2 | 12/2008 | Gauer |
| 7,731,412 | B2 | 6/2010 | Sparey-Taylor |
| 7,880,563 | B2 | 2/2011 | Khelif |
| 7,942,568 | B1 | 5/2011 | Branch |
| 8,415,619 | B2 | 4/2013 | Goodlett |
| 2001/0055529 | A1 | 12/2001 | Wixforth |
| 2003/0175947 | A1 | 9/2003 | Liu |
| 2004/0042915 | A1 | 3/2004 | Rife |
| 2004/0101975 | A1 | 5/2004 | Gauer |
| 2004/0115097 | A1 | 6/2004 | Wixforth |
| 2004/0257906 | A1 | 12/2004 | Scriba |
| 2006/0060769 | A1 | 3/2006 | Bousse |
| 2007/0128046 | A1 | 6/2007 | Gonnella |
| 2007/0140041 | A1 | 6/2007 | Sparey-Taylor |
| 2007/0252083 | A1 | 11/2007 | Arscott |
| 2007/0264161 | A1 * | 11/2007 | Rathgeber ............... 422/100 |
| 2008/0094937 | A1 | 4/2008 | Li |
| 2008/0211602 | A1 | 9/2008 | Khelif |
| 2009/0098027 | A1 | 4/2009 | Tabata |
| 2010/0139377 | A1 * | 6/2010 | Huang et al. .............. 73/61.75 |
| 2010/0191277 | A1 | 7/2010 | McEwen |
| 2010/0200092 | A1 * | 8/2010 | Beltram et al. ............... 137/828 |
| 2010/0206696 | A1 | 8/2010 | Kondoh |
| 2012/0145890 | A1 * | 6/2012 | Goodlett et al. ............. 250/282 |
| 2012/0149126 | A1 | 6/2012 | Wilson |
| 2013/0213488 | A1 * | 8/2013 | Weitz et al. .................... 137/13 |
| 2013/0330247 | A1 | 12/2013 | Wilson |
| 2014/0083174 | A1 | 3/2014 | Rebound |

FOREIGN PATENT DOCUMENTS

| | | |
|---|---|---|
| CN | 101301990 | 11/2008 |
| EP | 1183102 | 3/2002 |
| EP | 1246699 | 10/2002 |
| EP | 1286774 | 3/2003 |
| EP | 1289133 | 3/2003 |
| EP | 1366356 | 12/2003 |
| EP | 1377364 | 1/2004 |
| EP | 1409722 | 4/2004 |
| JP | 11114467 A | 4/1999 |
| JP | 2008104966 A | 5/2008 |
| WO | WO 02/071051 | 9/2002 |
| WO | WO 03055976 | 7/2003 |
| WO | WO 2004/076047 A1 | 9/2004 |
| WO | WO 2005/100953 | 10/2005 |
| WO | WO 2006/087496 | 8/2006 |
| WO | WO 2007/118224 | 10/2007 |
| WO | WO 2007/128045 | 11/2007 |
| WO | WO 2007/128046 A1 | 11/2007 |
| WO | WO 2007/132211 A1 | 11/2007 |
| WO | WO 2007128046 A1 * | 11/2007 |
| WO | WO 2008/040008 | 4/2008 |
| WO | WO 2008/089174 A2 | 7/2008 |
| WO | WO 2009/073402 A2 | 6/2009 |
| WO | WO 2009/122340 | 10/2009 |
| WO | WO 2011/023949 | 3/2011 |
| WO | WO 2011/060369 A1 | 5/2011 |
| WO | WO 2012/099291 A1 | 7/2012 |
| WO | WO 2012/114076 | 8/2012 |
| WO | WO 2012/156755 | 11/2012 |

OTHER PUBLICATIONS

Alvarez, et al., (2007) 16$^{th}$ Australasian Fluid Mechanics Conference (AFMC) 621-624, "Microaerosol and Nanoparticle Synthesis for Drug Delivery via Surface Acoustic Wave Atomization".

Alvarez, et al., (2008) Nanotechnology 19:455103, "Rapid generation of protein aerosols and nanoparticles via surface acoustic wave atomization".

Baek et al., (2010) Lab on a Chip 10:909-917, "Wireless induction heating in a microfluidic device for cell lysis".

Batchelor G. K. (1951) Q. J. Mech. Appl. Math 4:29-41, "Note on a class of solutions of the Navier-Stokes equations representing steady rotationally-symmetric flow".

Benchabane et al. (2005) Ultrasonics Symposium IEEE 2.922-925, "Silicon phononic crystal for surface acoustic waves".

Benchabane et al. (2006) Photonic Crystal Materials and Devices III 6182:18216, "Elastic band gaps for surface modes in an ultrasonic lithium niobate photonoic crystal".

Bennes et al. (2007) IEEE Transactions on Ultrasonics Ferroelectrics and Frequency Control 54(10):2146-2151, "Detection and high-precision positioning of liquid droplets using SAW Systems".

Beyssen et al.(2005) Ultrasonics Symposium IEEE 2:1028-1031, "Surface acoustic wave microfluidic device".

Borthwick et al., (2005) Anal. Chem. 77:7242-7245, "Improvement of Immunodetection of Bacterial Spore Antigen by Ultrasonic Cavitation".

Bourquin et al. (2011) Lab Chip 11:2725-2730, "Integrated immunoassay using tuneable surface acoustic waves and lensfree detection".

Bourquin et al. (2010) Lab on a Chip, "Tuneable surface acoustic waves for fluid and particle manipulations on disposable chips".

Bourquin et al. (2011) Adv Mater 23:1458-1462, "Phononic Crystals for Shaping Fluids".

Chen et al. (2008), Electrophoresis 29:1844-1851, "On-line cell lysis and DNA extraction on a microfluidic biochip fabricated by microelectromechanical system technology".

Cheng et al. (1998) Nature Biotechnology 16:541-546, "Preparation and hybridization analysis of DNA/RNA from *E. coli* on microfabricated bioelectronic chips".

Di Carlo et al. (2003) Lab on a Chip 3:287-291, "Reagentless mechanical cell lysis by nanoscale barbs in microchannels for sample preparation".

Djafari-Rouhani B et al. (2008) Photonics and Nanostructures—Fundamentals and Applications 6:32-37, "Absolute band gaps and waveguiding in free standing and supported phononic crystal slabs".

Dogheche et al. (2002) Applied Physics Letters vol. 81, No. 7 p. 81(7):1329, "Thick LiNbO3 layers on diamond-coated silicon for surface acoustic wave filters".

Du X. Y. et al.(2007) Journal of Physics: Conference Series, 76:012035, "ZnO film for application in surface acoustic wave device".

Du, X.Y. et al., (2009) Journal of Applied Physics 105(2):024508-7, "Microfluidic pumps employing surface acoustic waves generated in ZnO thin films".

Eckart C., (1948) Phys. Rev. 73:68-76, "Vorticies and Streams Caused by Sound Waves".

(56) References Cited

OTHER PUBLICATIONS

Ehlers K. M. & Koiller J. (2011) Math Comput Model 53:1489-1504, "Could cell membranes produce acoustic streaming? Making the case for Synechococcus self-propulsion".
Ehlers K. M., Samuel A. D., Berg H. C., & Montgomery R. (1996) Proc Natl Acad Sci 93:8340-8343, "Do cyanobacteria swim using traveling surface waves?".
Ennis W.J., Lee C., Plummer M., & Menses P. (2011) Plast Reconstr Surg. 127(Suppl 1):935, "Current status of the use of modalities in wound care: electrical stimulation and ultrasound therapy".
Eschbach et al. (2001) J. Appl. Toxicol 21:513-519, "Improved Erythrocyte Lysis Assay in Microtitre Plates for Sensitive Detection and Efficient Measurement of Haemolytic Compounds from Ichthyotoxic Algae".
Franke et al. (2010) Lab Chip 10:789-794, "Surface acoustic wave actuated cell sorting (SAWACS)".
Friend J. & Yeo L. (2011) Rev Mod Phys 83:647, "Microscale acoustofluidics: Microfluidics driven via acoustics and ultrasonics".
Frommelt, T. et al., (2008) IEEE Transactions on 55(10):2298-2305, "Flow patterns and transport in Rayleigh surface acoustic wavestreaming: combined finite element method and raytracing numerics versus experiments. Ultrasonics, Ferroelectrics and Frequency Control".
Fu et al., (2010) Sensors and Actuators B: Chemical 143:606-619, "Recent developments on ZnO films for acoustic wave bio-sensing and microfluidics applications: a review".
Guenneau S., Movchan A., Petursson G., Ramakrishna S.A. (2007) New J. Phys. 9:1-18, "Acoustic metamaterials for sound focusing and confinement".
Hall et al., (2007) IEEE transactions on ultrasonics, 54:569-575 "ferroelectrics, and frequency control".
Heron et al. (2010) Anal. Chem. 82:3985-3989, "Surface Acoustic Wave Nebulization of Peptides As a Microfluidic Interface for Mass Spectrometry".
Ho et al., (2011)Anal. Chem. 83(9):3260-6 "Paper-based microfluidic surface acoustic wave sample delivery and ionization source for rapid and sensitive ambient mass spectrometry".
Hodgson et al. (2009) Appl. Phys. Lett.94:024102-024103, "Transmitting high power of acoustic radiation via fluid couplants into superstrates for microfluidics".
Hongyu Yupp. and Eun Sok K., (2004) Micro-Electro Mechanical Systems, 17th IEEE International Conference on, p. 486-489, "Ultrasonic underwater thruster".
Hon K. M. T. & Ito K. (1997) International Journal of the Japan Society for Precision Engineering 31:1, "Development of ultra-small sized servo actuator with brushless DC motor, planetary gear drive and optical rotary encoder".
Hsu J. and Wu T., (2006) Phys Rev. B, 74, 144303, "Efficient formulation for band-structure calculations of two dimensional phononic-crystal plates".
Kim et al. (2005) Sensors and Actuators B 107(2):535-545, "A device for fabricating protein chips by using a surface acoustic wave atomizer and electrostatic deposition".
Kondoh et al. (2009) Sensors and Actuators A 149:292-297, "Development of temperature-control system for liquid droplet using surface acoustic wave devices".
Kondoh et al. (2005) IEEE transactions on ultrasonics, ferroelectrics, and frequency control 52(10), "Liquid Heating Effects by SAW Streaming on the Piezoelectric Substrate".
Kuo N. K., Zuo C., Piazza G. (2009) Joint Meeting of the European Frequency and Time Forum and the IEEE International Frequency Control Symposium 10-13, "Demonstration of inverse acoustic band gap structures in AIN and integration with piezoelectric contour mode wideband transducers".
Kuo, C.H. and Z. Ye, (2004) Journal of Physics D-Applied Physics 37(15):2155-2159, "Sonic crystal lenses that obey the lensmaker's formula".
Kurosawa et al. (1995) Sensors and Actuators 50(1-2):69-74, "Surface acoustic wave atomizer".

Kurosawa M., Takahashi M., & Higuchi T. (1996) IEEE Trans Ultrason Ferroelectr Freq Control 43: 901-906, "Ultrasonic linear motor using surface acoustic waves".
Laude V., Wilm M., Benchabane S., Khelif A. (2004) Ultrasonics Symposium, 2004 IEEE 2:10461049, "Full band gaps for surface acoustic waves in piezoelectric phononic crystals".
Laugharn et al., Methods and Apparatus for acoustically controlling liquid solutions in microfluidic devices WO01070381 (Covaris, Inc.) and family.
Lee D. W. & Cho Y.-H., (2007) Sensors and Actuators B 124:84-89, "A continuous electrical cell lysis device using a low dc voltage for a cell transport and rupture".
Li H. et al. (2007) Biomedical Microdevices, Kluwer Academic Publishers, BO 9(5):647-656, "Surface acoustic wave concentration of particle and bioparticle suspensions".
Lighthill J., (1978) J. Sound Vib., 61:391-418 "Acoustic streaming".
Mohammadi, S., et al., (2007) Electronics Letters, 43(16):898-899, "Complete phononic bandgaps and bandgap maps in twodimensional silicon phononic crystal plates".
Mohammadi, S., et al., (2008) Applied Physics Letters 92(22):3, "Evidence of large high frequency complete phononic band gaps in silicon phononic crystal plates".
Moroney et al. (1991), Appl. Phys. Lett., 59:774-776, "Microtransport induced by ultrasonic Lamb waves".
Morton et al. (2008) PNAS 105(21):7434-7438; doi:10.1073/pnas.0712398105.
Muller C et al. (2007) Zinc Oxide Materials and Devices II 6474:647413-647415, "Surface acoustic wave devices".
Neuzil P. et al, (2006) Mol. BioSyst. 2:292-298, "Disposable real-time microPCR device: lab-on-a-chip at a low cost".
Nyborg W., (1965) Academic Press, New York, "Acoustic Streaming".
Olsson, R.H., et al., (2008) Sensors and Actuators a-Physical 145:87-93, "Microfabricated VHF acoustic crystals and waveguides".
Pal et al. (2009), Colloid and Polymer Science 287(4):481-485, "Hybrid ZnO/polymer thin films prepared by RF magnetron sputtering".
Pennec Y. et al. (2005) Appl. Phys. Lett. 87:261912-261913, "Acoustic channel drop tunneling in a phononic crystal".
Prada C., Clorennec D., Murray T. W., Royer D. (2009) J. Acoust. Soc. Am. 126:620-625, "Influence of the anisotropy on zerogroup velocity Lamb modes".
Qi et al. (2009), Lab on Chip 9:2184-2193, "Miniature inhalation therapy platform using surface acoustic wave microfluidic atomization".
Qiu C., Liu Z., Mei J., Shi J. (2005) Appl. Phys. Lett. 87:104101-104103, "Mode-selecting acoustic filter by using resonant tunnelling of two-dimensional double phononic crystals".
Raghaven R. V., Friend J. R., Yeo L. Y. (2010) Micorfluid. Nanofluid. 7:73-84, "Particle concentration via acoustically driven microcentrifugation: microPIV flow visualization and numerical modelling studies".
Renaudin A. et al., (2009) Sensors and Actuators B: Chemical, 138(1), 374-382, "Monitoring SAW-actuated microdroplets in view of biological Applications".
Renaudin et al. (2006) Sensors and Actuators B 113:389, "SAW nanopump for handling droplets in view of biological applications".
Sankaranarayanan et al. (2008) Phys. Rev. E Stat. Phys. Plasmas Fluids Relat. Interdiscip. Topics 77: 066308, "Flow induced by acoustic streaming on surface-acoustic-wave devices and its applications in biofouling removal: A computational study and comparisons to experiment".
Scheerschmidt, G., Kirk, K. J., McRobbie G., (2010) Journalism of Magnetism and Magnetic Materials 322:1628-1630, "Resonance modes of magnetically generated surface waves in acoustic wave guide systems".
Schneider et al. (2008) ChemPhysChem 9: 641-645, "An Acoustically Driven Microliter Flow Chamber on a Chip (μFCC) for Cell-Cell and Cell-Surface Interaction Studies".
Sethu et al. (2004) Anal. Chem. 76:6247-6253, "Continuous Flow Microfluidic Device for Rapid Erythrocyte Lysis".

(56) References Cited

OTHER PUBLICATIONS

Shi et al. (2009) Lab Chip 9:2890, "Acoustic tweezers: patterning cells and microparticles using standing surface acoustic waves (SSAW)".

Shi, J. et al., (2008) Lab on a Chip, 8(2), 221-223, "Focusing microparticles in a microfluidic channel with standing surface acoustic waves (SSAW)".

Shilton et al. (2008), J. Appl. Phys. 104:014910, "Particle concentration and mixing in microdrops driven by focused surface acoustic waves".

Shiokawa et al. (1989) Proc IEEE Ultrason. Symp. 641:643-646, "Liquid streaming and droplet formation caused by leaky Rayleigh waves".

Siegrist et al. (2010) Lab on a Chip 10:363-371, "Validation of a centrifugal microfluidic sample lysis and homogenization platform for nucleic acid extraction with clinical samples".

Sinclair M. J. (2000) Seventh Intersociety Conf. on Thermal and Thermomechanical Phenomena in Electronic Systems1: 127-132, "A high force low area MEMS thermal actuator".

Smith et al. (1969) IEEE T. Microw. Theory 17:856-864.

Sritharan K. et al, (2006) Applied Physics Letters, AIP,American Institiute of Physics, Melville, NY, US, 88(5):54102-054102, "Acoustic mixing at low Retnold's numbers".

Strobl et al. (2004), IEEETrans. Ultrason, Ferroelect. Freq. Control 51:1432-1436.

Su Y-C L..L & Pisano A. P. (2002) J Microelectromech Syst 11: 736, "A water-powered osmotic microactuator".

Tai Y-C & Muller R. S. (1989) Sens Actuators 20:49-55, "IC-processed electrostatic synchronous micromotors".

Tan A. C. H. And Hoover F. S., (2010) IEEE Oceans p. 1-9, "Thrust and wake characterisation in small, robust ultrasonic thrusters".

Tan et al. (2009) Physical Review Letters 103:024501, "Interfacial Jetting Phenomena Induced by Focused Surface Vibrations".

Tan et al. (2007), Lab on a Chip, 7(5):618-625, "Microparticle collection and concentration via a miniature surface acoustic wave device".

Taylor et al. (2001) Analytical Chemistry 73:492-496, "Lysing Bacterial Spores by Sonication through a Flexible Interface in a Microfluidic System".

Überall H (1973) Phys. Acoustics: principles and methods 10:1-57, " Surface Waves in Acoustics".

Vasseur, J.O. et al., (2008) Physical Review B (Condensed Matter and Materials Physics), 77(8):085415-15, "Absolute forbidden bands and waveguiding in two-dimensional phononic crystal plates".

Waters et al. (1998) Anal. Chem. 70(1):158-162, "Microchip Device for Cell Lysis, Multiplex PCR Amplification, and Electrophoretic Sizing".

Watson B. et al. (2009) J Micromech Microeng 19: 022001, "Piezoelectric ultrasonic resonant motor with stator diameter less than 250 μm: the Proteus motor".

Watson B. et al., (2010) J. Micromech. Microeng. 20:115018, "Modelling and testing of a piezoelectric ultrasonic micro-motor suitable for in vivo micro-robotic applications".

Wilson et al. (2010) Anal. Chem.82:2119-2123.

Wilson I. G., (1997) Applied and Environmental Microbiology, 63(10):3741-3751, "Inhibition and Facilitation of Nucleic Acid Amplification".

Wixforth A, Gauer C, Scriba J, Wassermeier M, Kircher R (2003) Microfluidics, BioMEMS, and Medical Microsystems 4982:235-242, "Flat fluidics: a new route toward programmable biochips".

Wixforth A. (2006) Journal of the Association for Laboratory Automation 11:399-405, "Acoustically Driven Programmable Microfluidics for Biological and Chemical Applications".

Wixforth A., (2003) Superlattices and Microstructures 33:389-396, "Acoustically-driven planar microfluidics".

Wu T. T. et al, (2009) Applied Physics Letters, AIP, American Institiute of Physics, Melville, NY, US, 94(10):101913-101913, "Utilization of phononic-crystal reflective gratings in a layered surface acoustic wave device".

Wu T. T., Hsu C. H., Sun J. H. (2006) Appl. Phys. Lett. 89:171912-171913, "Design of a highly magnified directional acoustic source based on the resonant cavity of two-dimensional phononic crystals".

Wu, T. & Chang, I., (2005) Journal of Applied Physics, 98(2), 024903-7, "Actuating and detecting of microdroplet using slanted finger interdigital transducers".

Wu, T.T., L.C. Wu, and Z.G. Huang, (2005)Journal of Applied Physics, 97(9): 7, "Frequency band-gap measurement of two-dimensional air/silicon phononic crystals using layered slanted finger interdigital transducers".

Wu, T.T., Z.G. Huang, and S.Y. Liu, (2005) Zeitschrift Fur Kristallographie, 220(9-10): 841-847, "Surface acoustic wave band gaps in micro-machined air/silicon phononic structures—theoretical calculation and experiment".

Yager et al. (2006), Nature 442:412-418, "Microfluidic diagnostic technologies for global public health".

Yang et al., (2009) Nanotechnology 20(46):465201, "Solution-processed flexible ZnO transparent thin-film transistors with a polymergate dielectric fabricated by microwave heating,".

Yatsuda H. and Yamanouchil K., (2000) IEEE Trans. Ultrason. Ferroelectr. Freq. Control, 47:140-147.

Yeo L. and Friend J. R., (2009) Biomicrofluidics, 3:012002, "Ultrafast microfluidics using surface acoustic waves".

Zhang et al. (2009) Applied Acoustics 70:1137-1142, "Rapid Concentration of Particle and Bioparticle Suspension Based on Surface Acoustic Wave".

International search report on PCT/GB2010/001600, dated Sep. 2, 2011.

International Search Report on PCT/GB2012/000192 dated Jun. 1, 2012.

International Search Report on PCT/GB2012/051133 dated Dec. 13, 2012.

UKIPO search report on GB 1103211.7 dated Jun. 30, 2011.

UKIPO search report on GB0914762.0, dated Dec. 15, 2009.

UKIPO Search Report on GB1108462.1 dated Sep. 6, 2011.

UKIPO search report on GB1221614.9 dated Mar. 7, 2013.

UKIPO search report on GB1315755.7 dated Feb. 26, 2014.

English translation of CN search report on 201080049008.X dated Aug. 26, 2013.

http://medicalphysicsweb.org/cws/article/research/26443—"Ultrasound that won't have you in stitches—MedicalPhysicsWeb.pdf".

http://www.arobella.com/products/qoustic-description.htm—"Description—Qoustic Wound Therapy System™—Arobella Medical, LLC—Sound .pdf".

http://www.celleration.com/mist-therapy/—"Mist Therapy << Celleration.pdf".

http://www.misonix.com/medical/products/sonicone/—"Misonix—SonicOne O. R..pdf".

http://www.technologyreview.com/biomedicine/17215/—"An Ultrasonic Tourniquet to Stop Battlefield Bleeding_MIT Technology Review.pdf".

Standard F756—08, Standard Practice for Assessment of Hemolytic Properties of Materials, ASTM, Mar. 2009.

Guttenberg, et al. (2005) Lab Chip 5:308-317, "Planar chip device for PCR and hybridization with surface acoustic wave pump".

Wilson et al. (2011) Lab on a Chip 11:323-328, "Phononic crystal structures for acoustically driven microfluidic manipulations".

Bloch, et al. 1979 IEEE Ultrasonics Symposium pp. 687-690, "Selective reflection of surface acoustic waves by periodic dot arrays".

Wu, et al. (2004) Physical Review B 69:094301, "Surface and bulk acoustic waves in two-dimensional phononic crystal consisting of materials with general anisotropy".

\* cited by examiner

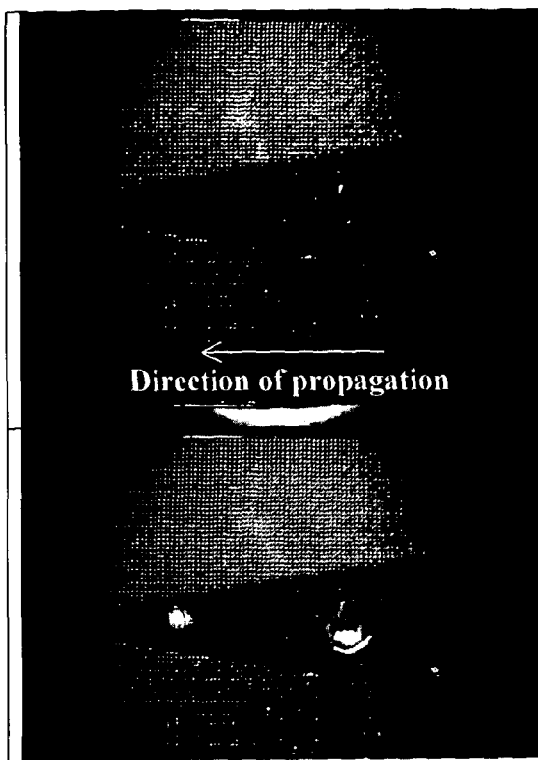
Fig. 8
Fig. 9
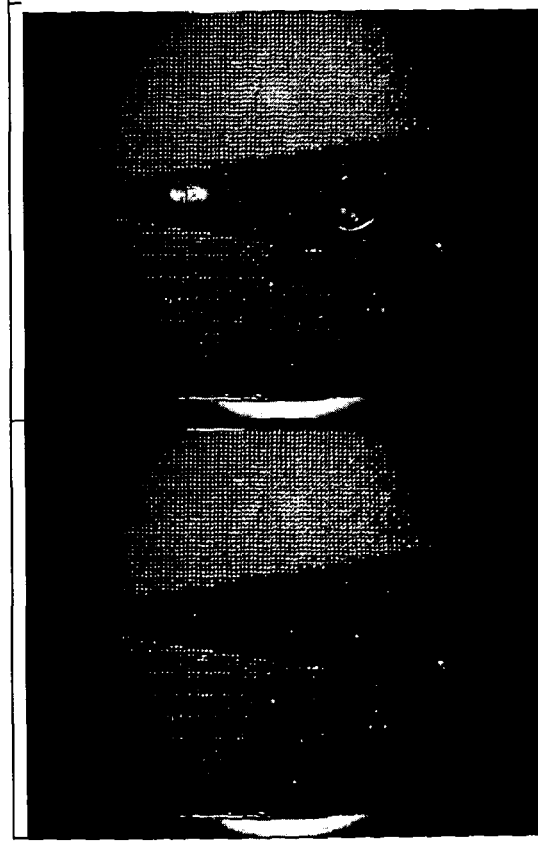
Fig. 10
Fig. 11

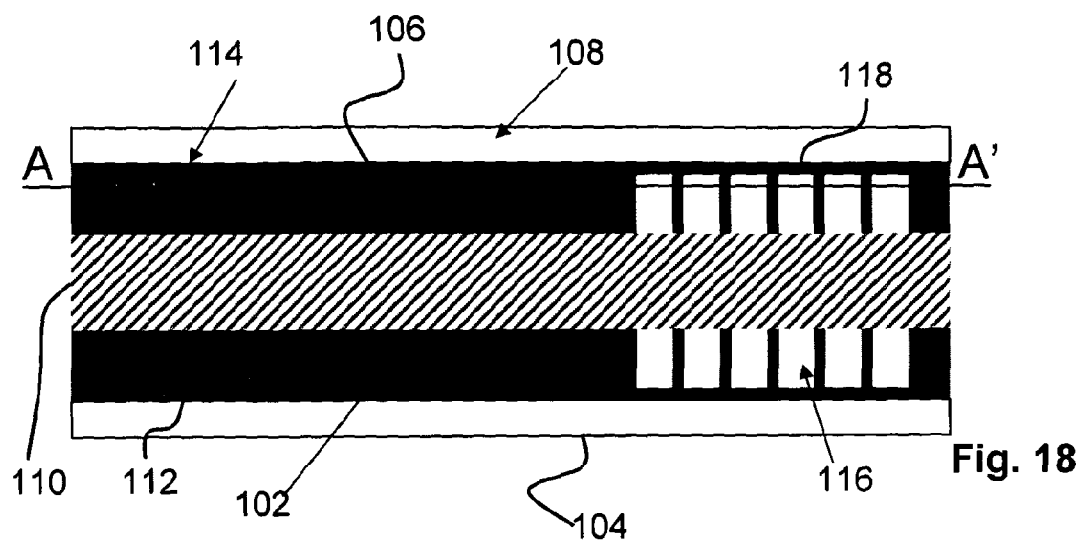
Fig. 18
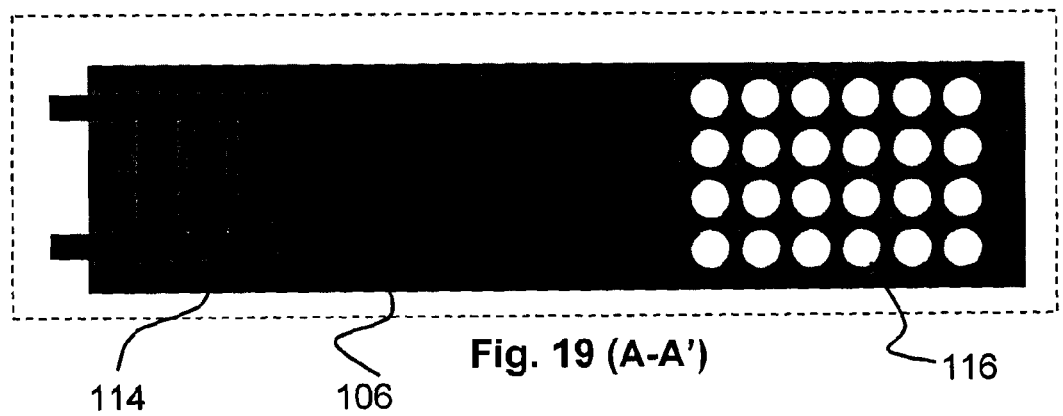
Fig. 19 (A-A')
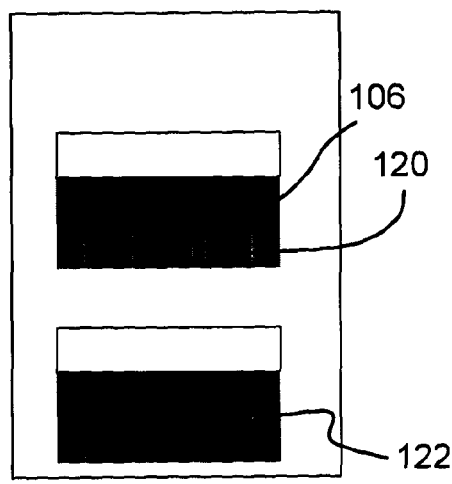
Fig. 20
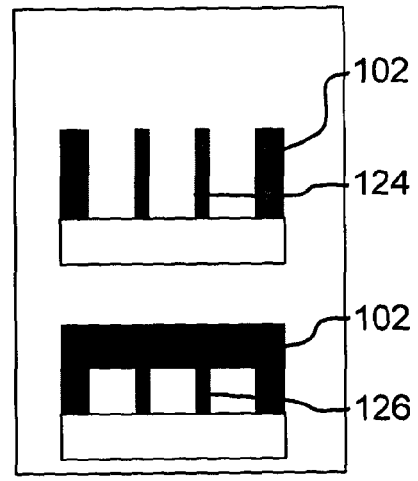
Fig. 21

FLUIDICS APPARATUS FOR SURFACE ACOUSTIC WAVE MANIPULATION OF FLUID SAMPLES, USE OF FLUIDICS APPARATUS AND PROCESS FOR THE MANUFACTURE OF FLUIDICS APPARATUS

RELATED APPLICATIONS

This application is a 35 U.S.C. §371 national phase application of PCT/GB2012/000192 (WO 2012/114076), filed on Feb. 24, 2012, entitled "Fluidics Apparatus for Surface Acoustic Wave Manipulation of Fluid Samples, Use of Fluidics Apparatus and Process for the Manufacture of Fluidics Apparatus", which application claims the benefit of GB 1103211.7, filed Feb. 24, 2011, which are each incorporated herein by reference in its entirety.

BACKGROUND TO THE INVENTION

1. Field of the Invention

The present invention relates to fluidics apparatus, uses of such apparatus and processes for the manufacture of such apparatus. Of particular, but not necessarily exclusive, interest is fluid sample manipulation in a microfluidics context. The invention has particular, but not exclusive, application to the manipulation of liquid droplets, for example in biological, biochemical, medical, veterinary and chemical assays, analysis, diagnosis, and synthesis and production of reagents and chemicals.

The present invention further relates to methods for lysing cells and to the use of a fluidics apparatus for lysing cells in a fluid sample. The invention further relates to methods for nebulising fluid samples and to the use of a fluidics apparatus for nebulising a fluid sample. This is of interest, for example, in the treatment of a sample for mass spectrometry and other analytical techniques. The invention further relates to methods for heating fluid samples and to the use of a fluidics apparatus for heating a fluid sample. Still further, the invention relates to methods for carrying out polymerase chain reaction (PCR) on a sample using a corresponding fluidics apparatus, optionally including heating of the sample.

2. Related Art

Microfluidics devices are well known for handling and analysing small volumes of fluids. For example, WO 2005/100953 discloses a system for measuring viscosity of fluids. Fluids are moved along microfluidic passageways using a thermal pump.

Alternative approaches to microfluidics liquid handling include the use of surface acoustic wave devices, as described in US 2007/0140041. In that document, there is disclosed the problem of mixing two microfluidics streams at a manifold, since at microfluidics dimensions, some liquids flow via laminar flow, and the lack of turbulence makes mixing difficult. Accordingly, US 2007/0140041 seeks to improve mixing between two fluid flows at a microfluidics manifold using surface acoustic waves (SAWs). A SAW transducer is located in contact with the manifold in order to promote mixing of the fluid streams at the manifold junction.

Surface acoustic waves (SAWs, the most common being Rayleigh waves) are acoustic waves that can be caused to travel along the surface of a material. Surface acoustic waves can be conveniently formed at the surface of a piezoelectric material by the application of a suitable electrical signal to an electrode arrangement at the surface of the piezoelectric material. A suitable electrode arrangement utilizes interdigitated electrodes, where a first electrode has an arrangement of parallel electrode fingers having a regular spacing between the fingers. A corresponding second electrode of similar shape has fingers which protrude into the gaps between the fingers of the first electrode. The combination of the electrode arrangement and the piezoelectric material forms a transducer.

SAW transducers are known particularly for use in frequency filters in telecommunications devices such as mobile telephones. In such a filter, there is an input transducer and an output transducer. The input signal is applied to the input transducer, to form a series of SAWs which propagate to the output transducer. At the output transducer, the SAWs are converted back into an electrical signal. For example, Dogheche et al [E. Dogheche, V. Sadaune, X. Lansiaux, D. Remiens, and T. Gryba "Thick $LiNbO_3$ layers on diamond-coated silicon for surface acoustic wave filters" Applied Physics Letters Vol. 81, No. 7 (12 Aug. 2002) p. 1329] disclose the fabrication of piezoelectric films for SAW filters. Typically, such filters are formed using known piezoelectric substrates such as quartz, $LiTaO_3$ or $LiNbO_3$. However, the formation of suitable interdigitated electrode patterns on the surface of such substrates by conventional photolithography whilst providing a filter operable up to suitable telecommunications frequencies is difficult. Accordingly, Dogheche et al formed thick (around 1 µm thick) piezoelectric $LiNbO_3$ layers on diamond-coated silicon and demonstrated their operation as SAW filters at 293 MHz.

It has also been noted that it is possible to provide quasi crystalline structures in order to manipulate SAWs. It has been shown to be possible to use a variety of phononic band-gap structures to affect an acoustic wavefront generated in a piezoelectric material. For example, Wu et al [Wu, T. T., Z. G. Huang, and S. Y. Liu, "Surface acoustic wave band gaps in micro-machined air/silicon phononic structures—theoretical calculation and experiment" Zeitschrift Fur Kristallographie, 2005. 220(9-10): p. 841-847] discuss their investigations of the phononic band gaps in structures formed by micromachining silicon with a square lattice arrangement of holes. The transducer was formed with interdigitated electrodes having parallel fingers. Furthermore, Wu et al [Wu, T. T., L. C. Wu, and Z. G. Huang, "Frequency band-gap measurement of two-dimensional air/silicon phononic crystals using layered slanted finger interdigital transducers" Journal of Applied Physics, 2005. 97(9): p. 7] disclose the results of investigations using a similar phononic crystal using electrodes with interdigitated non-parallel fingers in the form of a fan shape. Furthermore, in a purely theoretical paper, Kuo and Ye [Kuo, C. H. and Z. Ye, "Sonic crystal lenses that obey the lensmaker's formula" Journal of Physics D-Applied Physics, 2004. 37(15): p. 2155-2159] discuss the properties of structures that could be used to focus acoustic waves.

The term "phononic crystal" is used as an analogy to a "photonic crystal". In a photonic crystal, a periodic structure causes reflections due to scattering of incident light, thereby allowing interference between the reflected light and the incident light as it propagates through the "crystal" (which typically is formed of an arrangement of dielectric materials based on a regular array, such as a Bragg reflector), at one or more wavelengths and angles of incidence. This interference manifests itself as a prevention of propagation of the light through the crystal at a certain wavelength (or range of wavelengths) and direction. Thus, there is a "band gap" of frequencies at which light cannot propagate through the photonic crystal. A phononic crystal, by analogy, has a periodic arrangement of discontinuities or variations in the mechanical properties of the material or materials making up the phononic crystal. Such a phononic crystal can prevent acoustic or mechanical waves of specific wavelength from propagating through the crystal. Since SAWs can be formed at tightly defined frequencies, the effect of phononic crystals on the propagation of SAWs has been studied by several groups.

Mohammadi et al (2007) [Mohammadi, S., et al., "Complete phononic bandgaps and bandgap maps in two-dimensional silicon phononic crystal plates" Electronics Letters, 2007. 43(16): p. 898-899] disclose the formation of complete phononic band gap structures using a square array of holes or a hexagonal array of holes in a silicon plate. In a publication from the same group, Mohammadi et at (2008) [Mohammadi, S., et al., "Evidence of large high frequency complete phononic band gaps in silicon phononic crystal plates" Applied Physics Letters, 2008. 92(22): p. 3] discuss the formation of large complete phononic band gaps using a hexagonal array of holes through a silicon plate.

Olsson et al [Olsson, R. H., et al., "Microfabricated VHF acoustic crystals and waveguides" Sensors and Actuators a—Physical, 2008. 145: p. 87-93] disclose the formation of acoustic bandgaps in a structure formed by including periodic arrays of tungsten scatterers in a silica matrix. Waveguides for the acoustic waves are provided by removing selected scatterers along a desired path.

Vasseur et al [Vasseur, J. O. et al., 2008. Absolute forbidden bands and waveguiding in two-dimensional phononic crystal plates. Physical Review B (Condensed Matter and Materials Physics), 77(8), 085415-15] set out a study of phononic bandgaps in a two dimensional phononic crystal plate formed by arrays of cylinders of a first material in a plate of a second material.

US 2008/0211602 discloses an acoustic wave device with a piezoelectric layer with transducer electrodes formed over a substrate, there being an omnidirectional acoustic mirror formed between the piezoelectric layer and the substrate.

Other workers have used SAWs in the manipulation of liquids. For example, Renaudin et al [A. Renaudin, P. Tabourier, V. Zhang, J. C. Camart and C. Druon "SAW nanopump for handling droplets in view of biological applications" Sensors and Actuators B, 113, 2006, p. 389] report on the fabrication and development of a SAW device for microfluidics for biological applications. SAWs at about 20 MHz are generated by interdigitated electrode transducers laid on a $LiNbO_3$ piezoelectric substrate. Droplets are transported along the surface of the transducer where hydrophilic micro tracks are provided between hydrophobic areas. Furthermore, the same research group [Renaudin, A. et al., 2009. Monitoring SAW-actuated microdroplets in view of biological applications. Sensors and Actuators B: Chemical, 138(1), 374-382] set out a method for determining the position of the droplet using echo signals detected by interdigitated transducers.

Du et al [Du, X. Y. et al., 2009. Microfluidic pumps employing surface acoustic waves generated in ZnO thin films. Journal of Applied Physics, 105(2), 024508-7] propose using ZnO thin films on Si substrates to form surface acoustic wave operated microfluidic pumps.

Frommelt et al [Frommelt, T. et al., 2008. Flow patterns and transport in Rayleigh surface acoustic wave streaming: combined finite element method and raytracing numerics versus experiments. Ultrasonics, Ferroelectrics and Frequency Control, IEEE Transactions on, 55(10), 2298-2305] investigate the patterns of liquid flow and particle transport inside a droplet subjected to surface acoustic waves.

Shi et al [Shi, J. et al., 2008. Focusing microparticles in a microfluidic channel with standing surface acoustic waves (SSAW). Lab on a Chip, 8(2), 221-223] propose using opposed interdigitated transducers to form an aligned arrangement of beads moving along a channel.

Wu and Chang [Wu, T. & Chang, I., 2005. Actuating and detecting of microdroplet using slanted finger interdigital transducers. Journal of Applied Physics, 98(2), 024903-7] disclose the movement of droplets on a SAW substrate by control of the signal applied to interdigitated transducers having fingers arranged in a slanting configuration.

Tan et al [Tan, M. K., J. R. Friend, and L. Y. Yeo, "Microparticle collection and concentration via a miniature surface acoustic wave device" Lab on a Chip, 2007. 7(5): p. 618-625] disclose the use of SAWs to collect microparticles such as pollen particles in a droplet of water. A water droplet is conveyed along a SAW transducer via a fluidic track.

Concentration of microparticles in droplets by asymmetric application of surface acoustic waves has also been described. Techniques described for breaking the symmetry of a surface acoustic wave involve aligning a drop on the edge of a parallel electrode interdigital transducer [A. Zhang, W. Liu, Z. Jiang and J. Fei, *Appl. Acoust.*, 2009, 70, 1137-1142.], positioning a gel to partially absorb the surface acoustic wave reflection (so that only part of the drop lies in the transmission pathway) [H. Li, J. R. Friend and L. Y. Yeo, *Biomed. Microdev.*, 2007, 9, 647-656], or using a more complex IDT that focuses the surface acoustic wave [R Shilton, M. Tan and L. Yeo, and J. Friend, *J. Appl. Phys.*, 2008, 104, 014910] using circular transducers with a fixed frequency and excitation pathway.

Bennes et al [J. Bennes, S Alzuage, F. Chemoux, S. Ballandras, P. Vairac, J-F Manceau and F. Bastien, "Detection and high-precision positioning of liquid droplets using SAW systems" IEEE Transactions on Ultrasonics Ferroelectrics and Frequency Control, 2007, 54(10): p. 2146-2151] disclose droplet detection and positioning using SAWs. The SAW devices used are formed from lithium niobate substrates ($LiNbO_3$ cut (XY1)/128°). Bennes et al explain that the droplets are moved due to the refraction of incoming SAWs along the substrate surface at the air/liquid interface, producing a resultant force which can have a component directed along the substrate surface. The $LiNbO_3$ substrate is treated to make it hydrophobic—this increases the contact angle with an aqueous droplet and decreases the force required to move the droplet by interaction with SAWs.

WO 02071051 discloses acoustic ejection of biomolecular samples for mass spectrometry.

WO 2007/128045 discloses the use of a SAW transducer to atomize a liquid droplet from a substrate coupled to a piezoelectric transducer by a fluid coupling layer, thereby forming zeolite nanocrystals.

Fluidics systems may be useful in the analysis of biological samples, for example in point-of-care diagnostic applications and portable biosensors. However, biological samples present a particular challenge for sample manipulation and analysis in fluidics, particularly microfluidics. Preparation of biological samples is often complex, involving multiple steps. Notably, for a biological sample containing cells the molecule of interest may be an intracellular molecule, such that sample preparation requires a cell disruption step in order to render intracellular molecules accessible for analysis and applications such as immunodiagnostics and pathogen detection.

There are a variety of ways to disrupt cells in order to release intracellular molecules for analysis. Cells are enclosed by a lipid bilayer called the plasma membrane (also known as the cell membrane, or cytoplasmic membrane), which defines the boundaries of the cell, Cell disruption by rupture of the plasma membrane is termed cell lysis, and this can be achieved by a variety of chemical and physical methods.

A typical chemical lysis procedure involves numerous steps, including the addition of lytic agents (e.g. enzymes, detergents), washing (usually using centrifugation steps), and elution of the processed samples for further analysis. Physical lysis procedures include heating and mechanical methods such as agitation with small particles (e.g. glass beads) and sonication (or ultrasonication). Sonication typically involves transmitting mechanical energy, via an immersed probe that oscillates with high frequency, to a solution containing cells in suspension, and resultant cavitation (the creation and collapse of microscopic bubbles) ruptures cells in the sample.

Chemical cell lysis procedures have been integrated into microfluidic systems [P. Sethu, M. Anahtar, L. L. Moldawer, R. G. Tompkins, and M. Toner, Continuous Flow Microfluidic Device for Rapid Erythrocyte Lysis, *Anal. Chem.* 2004, 76, 6247-6253; X. Chen, D. F. Cui and C. C. Liu, On-line cell lysis and DNA extraction on a microfluidic biochip fabricated by microelectromechanical system technology, *Electrophoresis* 2008, 29, 1844-1851]. However, these methods require lytic agents, which may significantly dilute the molecule of interest and thereby compromise sensitivity of subsequent detection steps. These methods also require a cumbersome liquid-driving system to move the liquids around the chip, which is impractical for point-of-care applications. Removal of lytic and/or eluting agents may be required for downstream processing or analysis of the sample, for example because these agents inhibit reactions (e.g. PCR-based amplification of nucleic acids), or because they compromise the molecule of interest.

Techniques have been developed for chemical-free lysis of cells in samples on microfluidic platforms. These include heating [S. Baek, J. Min and J.-H. Park, Wireless induction heating in a microfluidic device for cell lysis, Lab on a Chip, 2010, 10, 909-917], applying an electric field [D. W. Lee, Y.-H. Cho, A continuous electrical cell lysis device using a low dc voltage for a cell transport and rupture, *Sensors and Actuators B*, 2007, 124, 84-89], or using mechanical forces to disrupt the cells by the combined action of magnetic fields [J. Siegrist, R. Gorkin, M. Bastien, G. Stewart, R. Peytavi, H. Kido, M. Bergeron and M. Madou, Validation of a centrifugal microfluidic sample lysis and homogenization platform for nucleic acid extraction with clinical samples, *Lab on a Chip*, 2010, 10, 363-371], by using filter structures [D. Di Carlo, K.-H. Jeong and L. P. Lee, Reagentless mechanical cell lysis by nanoscale barbs in microchannels for sample preparation, *Lab on a Chip*, 2003, 3, 287-291] or by ultrasonication [M. T. Taylor, P. Belgrader, B. J. Furman, F. Pourahmadi, G. T. A. Kovacs and M. A. Northrup, Lysing Bacterial Spores by Sonication through a Flexible Interface in a Microfluidic System, *Analytical Chemistry* 2001, 73, 492-496 and M. T. Taylor, Apparatus and method for rapid disruption of cells or viruses, WO03055976 (Cepheid, Inc.)].

However, heat, electric fields or cavitation may compromise molecules of interest. Electrical lysis may be integrated in a microfluidics chip with other functions [J. Cheng, E. L. Sheldon, L. Wu, A. Uribe, L. O. Gerrue, J. Carrino, M. J. Heller, J. P. O'Connell, Preparation and hybridization analysis of DNA/RNA from *E. coli* on microfabricated bioelectronic chips, *Nature Biotechnology,* 1998, 16, 541-546], but other physical lysis methods require the addition of external actuations into the system to move the fluids around the chip, in a similar fashion as chemical-based lysis platforms. This has been a particular difficulty hindering the development of fully integrated "sample-to-answer" solutions for molecular diagnostics [P. Yager, T. Edwards, E. Fu, K Helton, K. Nelson, M. R. Tam and B. H. Weigl, Microfluidic diagnostic technologies for global public health, *Nature*, 2006, 442, 412-418].

SUMMARY OF THE INVENTION

The present invention builds on the work set out in PCT/GB2010/001600 (unpublished as at 2 Feb. 2011 but published as WO2011/023949 on 3 Mar. 2011). In that patent application, a fluidics apparatus is disclosed in which a fluid sample is manipulated using surface acoustic waves (SAWs). The transmission, distribution and/or behaviour of the SAWs is affected by an arrangement of surface acoustic wave (SAW) scattering elements in the apparatus.

In PCT/GB2010/001600, the SAWs are generated using an interdigitated transducer electrode structure on a 128° Y-cut X-propagating piezoelectric $LiNbO_3$ single crystal wafer. $LiNbO_3$ single crystal wafers are expensive. Therefore the disclosure in PCT/GB2010/001600 is to allow coupling between the piezoelectric $LiNbO_3$ single crystal wafer and a removable superstrate, the SAWs generated by the piezoelectric $LiNbO_3$ single crystal wafer being transmitted to the superstrate via a coupling medium. It is then the superstrate which provides a sample manipulation surface and the required arrangement of SAW scattering elements. The advantage of this is that the sample can be allowed to contaminate only the superstrate and not the piezoelectric $LiNbO_3$ single crystal wafer. Then the superstrate can be disposed of and the piezoelectric $LiNbO_3$ single crystal wafer can be re-used with a new superstrate and a new sample. This is cost-effective, since the superstrate can be manufactured relatively efficiently, for example by moulding.

However, the present inventors have found that the apparatus described above, though advantageous in many respects, is susceptible of some improvement. In particular, the performance of the apparatus can depend strongly on the alignment between the piezoelectric transducer and the SAW scattering elements on the superstrate. In the situation where the alignment is controlled by the user (e.g. in replacing one superstrate with a fresh superstrate), the subsequent performance of the apparatus can be difficult to predict. Furthermore, the performance of the device similarly depends on the coupling between the piezoelectric transducer and the superstrate. With all of this in mind, it is still preferred to use such apparatus in diagnostic applications, and other applications, in which the apparatus may not realistically be able to be used more than once, due to potential problems of contamination.

The present invention aims to address at least one of these problems. Preferably, the present invention reduces, ameliorates, avoids or even overcomes at least one of these problems.

Accordingly, in a first preferred aspect, the present invention provides a fluidics apparatus for manipulation of at least one fluid sample, the apparatus including:
a manipulation surface for location of the fluid sample;
a layer of surface acoustic wave (SAW) generation material; and
a transducer electrode structure arranged at the SAW generation material layer to provide surface acoustic waves (SAWs) at the manipulation surface for interaction with the fluid sample,
wherein the manipulation surface has at least one SAW scattering element for affecting the transmission, distribution and/or behaviour of SAWs at the manipulation surface, and
wherein the SAW generation material is selected from the group consisting of: polycrystalline material, textured polycrystalline material, biaxially textured polycrystalline material, microcrystalline material, nanocrystalline material, amorphous material and composite material.

In a second preferred aspect, the present invention provides a fluidics apparatus for manipulation of at least one fluid sample, the apparatus including:
a manipulation surface for location of the fluid sample;
a layer of surface acoustic wave (SAW) generation material; and
a transducer electrode structure arranged at the SAW generation material layer to provide surface acoustic waves (SAWs) at the manipulation surface for interaction with the fluid sample,
wherein the manipulation surface has at least one surface acoustic wave (SAW) scattering element for affecting the transmission, distribution and/or behaviour of SAWs at the manipulation surface,
and wherein the SAW generation material layer is not in the form of a single crystal layer.

In a third preferred aspect, the present invention provides a fluidics apparatus for manipulation of at least one fluid sample, the apparatus including:
a manipulation surface for location of the fluid sample;
a surface acoustic wave (SAW) generation material layer, wherein either:
    the material of the SAW generation material layer is selected from the group consisting of: polycrystalline material, textured polycrystalline material, biaxially textured polycrystalline material, microcrystalline material, nanocrystalline material, amorphous material and composite material, or
    the SAW generation material layer is not in the form of a single crystal layer,
a transducer electrode structure arranged at the SAW generation material layer to provide SAWs at the manipulation surface for interaction with the fluid sample,
wherein the manipulation surface has at least one surface acoustic wave (SAW) scattering element for affecting the transmission, distribution and/or behaviour of SAWs at the manipulation surface.

In a fourth preferred aspect, the present invention provides a fluidics apparatus for manipulation of at least one fluid sample, the apparatus including:
a surface acoustic wave (SAW) generation material layer having a manipulation surface for location of the fluid sample;
a transducer electrode structure arranged at the SAW generation material layer to provide SAWs at the manipulation surface for interaction with the fluid sample,
wherein the manipulation surface has at least one SAW scattering element extending at least partially into the SAW generation material layer for affecting the transmission, distribution and/or behaviour of SAWs at the manipulation surface.

In a fifth preferred aspect, the present invention provides a use of a fluidics apparatus to manipulate at least one fluid sample, the apparatus including:
a manipulation surface at which the fluid sample is located;
a surface acoustic wave (SAW) generation material layer, wherein either:
    the material of the SAW generation material layer is selected from the group consisting of: polycrystalline material, textured polycrystalline material, biaxially textured polycrystalline material, microcrystalline material, nanocrystalline material, amorphous material and composite material, or
    the SAW generation material layer is not in the form of a single crystal layer,
a transducer electrode structure arranged at the SAW generation material layer,
wherein the apparatus is operated to provide SAWs at the manipulation surface for interaction with the fluid sample, and wherein the manipulation surface has at least one SAW scattering element for affecting the transmission, distribution and/or behaviour of SAWs at the manipulation surface.

In a sixth preferred aspect, the present invention provides a use of a fluidics apparatus to manipulate at least one fluid sample, the apparatus including:
a surface acoustic wave (SAW) generation material layer having a manipulation surface for location of the fluid sample;
a transducer electrode structure arranged at the SAW generation material layer,
wherein the apparatus is operated to provide SAWs at the manipulation surface for interaction with the fluid sample, and wherein the manipulation surface has at least one SAW scattering element extending at least partially into the SAW generation material layer for affecting the transmission, distribution and/or behaviour of SAWs at the manipulation surface.

In a seventh preferred aspect, the present invention provides a process for manufacturing a fluidics apparatus for manipulation of at least one fluid sample, the apparatus including:
a manipulation surface for location of the fluid sample;
a surface acoustic wave (SAW) generation material layer; and
a transducer electrode structure arranged at the SAW generation material layer to provide surface acoustic waves (SAWs) at the manipulation surface for interaction with the fluid sample,
wherein the manipulation surface has at least one surface acoustic wave (SAW) scattering element for affecting the transmission, distribution and/or behaviour of SAWs at the manipulation surface
the process including forming the SAW generation material layer in situ on a support in a SAW generation material layer deposition step.

In an eighth preferred aspect, the present invention provides a process for manufacturing a fluidics apparatus for manipulation of at least one fluid sample, the apparatus including:
a surface acoustic wave (SAW) generation material layer having a manipulation surface for location of the fluid sample; and
a transducer electrode structure arranged at the SAW generation material layer to provide surface acoustic waves (SAWs) at the manipulation surface for interaction with the fluid sample,
wherein the manipulation surface has at least one surface acoustic wave (SAW) scattering element for affecting the transmission, distribution and/or behaviour of SAWs at the manipulation surface
the process including forming the SAW generation material layer so that the at least one SAW scattering element extends at least partially into the SAW generation material layer.

Preferred or optional features of the invention will now be set out. These may be applied singly or in any combination with any aspect of the invention, unless the context demands otherwise.

It is considered by the inventors (without wishing to be limited by theory) that SAWs tend to at least partially refract into the fluid sample. This refraction is due to the fluid sample having, in general, a different speed of propagation for the SAWs compared with the substrate. This produces streaming in the fluid sample. Accordingly, this is considered to be the origin of sample movement under the influence of SAWs.

It is possible that the fluid sample is in the form of a drop, e.g. a droplet such as a microfluidic droplet. However, other arrangements are possible for the fluid sample, e.g. a channel of fluid, or a fluid held in a chamber. In the following discussion, the term "droplet" is used, but as discussed above, it is intended that the invention is not necessarily limited to the manipulation of droplets.

The fluid may comprise a liquid. Furthermore, the fluid may comprise one or more particles. For example, the fluid may be a liquid containing solid (or substantially solid) particles. Of particular interest are fluids comprising a suspension of solid particles in a carrier liquid.

The volume of the fluid sample depends on the application of the apparatus. For example, the volume of the fluid sample may be at least 1 picoliter. More preferably, the volume of the fluid sample is at least 10 picoliter, at least 100 picoliter or at least 500 picoliter. Larger volumes are contemplated, e.g. at least 1 nanoliter, at least 10 nanoliter, at least 100 nanoliter or at least 500 nanoliter. Still larger volumes are possible in some applications, e.g. at least 1 microliter or at least 10 microliter. The preferred upper limit for the volume of the fluid sample is about 5 milliliter, more preferably about 1 milliliter, still more preferably about 0.1 milliliter.

The manipulation surface may be treated in order to provide it with hydrophobicity. For example, a contact angle between a water droplet and a flat region of the manipulation surface may be not less than 65 degrees.

The SAW generation material layer may be formed from any suitable material for generating surface acoustic waves. SAWs may be generated, for example, by a piezoelectric process, by a magnetostrictive process, by an electrostrictive process, by a ferroelectric process, by a pyroelectric process, or by an electromagnetic process. It is most preferred that the SAW generation material layer is formed from a piezoelectric layer. In the disclosure set out below, the term "piezoelectric layer" is used but is it understood here that similar considerations would apply to SAW generation material layers formed, for example, of magnetostrictive materials. Therefore, unless the context demands otherwise, the optional features set out in relation to the "piezoelectric layer" are to be understood as applying more generally to the SAW generation material layer, when formed of any suitable material.

The present inventors further consider that the present invention is not necessarily limited to the generation and manipulation of SAWs. It is considered that the generation of other acoustic waves, such as bulk acoustic waves, is possible using the principles of the present invention. Such acoustic waves are susceptible of manipulation in a similar manner to SAWs. Such manipulation (e.g. affecting the transmission, distribution and/or behaviour of the acoustic waves) is possible using at least one acoustic wave scattering element (more preferably an arrangement of such scattering elements). Bulk acoustic waves, for example, give rise to corresponding acoustic waves or displacements at a free surface, such as the sample manipulation surface. Therefore, in the present disclosure, it is to be understood that SAWs are only one example of a suitable acoustic wave which can be manipulation to, in turn, provide suitable manipulation of a sample. Thus, although in this disclosure the terms "SAW", "surface acoustic wave", "SAWs" and "surface acoustic waves" are used, it is to be understood that these may be substituted or supplemented by the terms "bulk acoustic wave" and "bulk acoustic waves" or the terms "acoustic wave" and "acoustic waves", unless the context demands otherwise.

The present inventors also consider that the invention is not necessarily limited to the manipulation of a fluid sample. Samples which may be regarded as solid, or substantially solid (e.g. feces) may be manipulated using the apparatus, in the manner set out in more detail below.

Preferably, the piezoelectric layer is formed on a support. The support may simply provide mechanical support for the piezoelectric layer. The support may be formed from plastics material. In the process of manufacturing the apparatus, the support may be removed if the remainder of the apparatus is self-supporting.

The transducer electrode structure may be formed on or under the piezoelectric layer. However, preferably the transducer electrode structure is at least partially embedded in the piezoelectric layer. This is preferred so that it is possible for the surface of the transducer electrode structure to be continuous with the surface of the piezoelectric layer. This allows the construction of the apparatus to be simplified, and may allow for improved flow characteristics of the fluid sample in the apparatus. Preferably, the transducer electrode structure has an arrangement of interdigitated electrodes. In some embodiments, it is preferred that the transducer is tunable, such that the lateral position of the SAWs emission train is movable. For example, the slanted interdigitated arrangement of electrodes suggested by Wu and Chang [Wu, T. & Chang, I., 2005. Actuating and detecting of microdroplet using slanted finger interdigital transducers. Journal of Applied Physics, 98(2), 024903-7] can be used for the transducer. Slanted interdigitated arrangements of electrodes suitable for use in the present invention are described in more detail below.

The manipulation surface may be a surface of a superstrate coupled to the piezoelectric layer. In that case, preferably the superstrate is permanently coupled to the piezoelectric layer, in the sense that it is not removable from the piezoelectric layer without damage to the apparatus. Preferably, the superstrate is formed in register with the piezoelectric layer, this register being determined at the time of manufacture of the device. The superstrate may be formed over or under the piezoelectric layer. The superstrate may be a film formed on the piezoelectric layer. The film may have a thickness of 5 μm or less, more preferably a thickness of 1 μm or less. The superstrate here may also function as a support for the piezoelectric layer. For example, the superstrate may be the support layer on which the piezoelectric layer is deposited during the deposition step. Note that the support may, in use, be located above or below the piezoelectric layer.

However, preferably the manipulation surface is a surface of the piezoelectric layer. This is preferred because it avoids the need for the formation of a superstrate in register with the piezoelectric layer. In some circumstances, the surface of the piezoelectric layer may be treated in order to make it compatible with the fluid sample of interest. In these circumstances, the piezoelectric layer includes surface-treated and surface-passivated piezoelectric layers. Previously, with the use of single crystal piezoelectric transducers, it has been considered uneconomical to allow contamination of the piezoelectric surface with the sample, since this may mean that the piezoelectric transducer cannot be re-used. However, the present inventors have realised that it is possible instead to manufacture suitable devices using non-single-crystal piezoelectric layers, using piezoelectric layer deposition processes that are suitable for economical mass processing manufacture.

In some embodiments, it is possible for the manipulation surface to be separated from the piezoelectric layer, in the direction of travel of the SAWs. In this case, the manipulation surface may not overlie the piezoelectric layer. Instead, the manipulation surface may be in SAW communication with the piezoelectric layer via a SAW transmission material layer. In this way, the SAWs can be generated by the combination of the transducer electrode structure and the piezoelectric layer, transmitted into the SAW transmission material layer, and carried to the sample manipulation surface. As will be clear, the sample manipulation surface may therefore be a surface of the SAW transmission material layer. An advantage of this is that the amount of piezoelectric material required in the apparatus may be reduced.

The manipulation surface may extend, for example, the full length and/or the full width and/or the full height of the apparatus. In this case, a length end and/or a width end and/or a height end of the apparatus may additionally scatter the surface acoustic waves. However, preferably the at least one SAW scattering element is formed interiorly of an exterior envelope of the manipulation surface defined by the full length and/or the full width and/or the full height of the apparatus.

In some embodiments, the at least one SAW scattering element includes a step change in the height of the manipulation surface. The SAW scattering element may include a ridge formed in the manipulation surface. The SAW scattering element may include a groove formed in the manipulation surface. More generally, the at least one SAW scattering element may include a linearly extending change in the profile of the manipulation surface.

Preferably, a plurality of SAW scattering elements are provided. These preferably cooperate to provide the required effect on the transmission, distribution and/or behaviour of SAWs at the manipulation surface.

Preferably, the SAW scattering elements have an arrangement based on a periodic arrangement. The periodic arrangement may be a one dimensional arrangement or a two dimensional arrangement. A two dimensional arrangement is preferred. The periodic nature may be, for example, translational symmetry and/or rotational symmetry. The term "based on" is used here because it is considered that the arrangement need not be precisely periodic. Furthermore, the arrangement may be deliberately displaced from a true periodic arrangement in order to provide a specific effect on the surface acoustic waves. For example, the arrangement may be progressively displaced from a true periodic arrangement with distance from a certain starting point in the arrangement. Furthermore, the arrangement may include one or more areas or lines of defective periodicity in the periodic arrangement. In some cases, the periodicity can be varied amid a single crystal by use of gradients, over which the pitch and or the size of the elements is varied. This variation in periodicity can have applications in waveguiding or lenses (focusing the acoustic power).

Typically, the periodic arrangement is a two-dimensional pattern, in that the periodicity extends in two dimensions. Suitable periodic patterns include translationally symmetrical lattice patterns such as tetragonal, square, trigonal, hexagonal, etc. Other suitable periodic patterns include rotationally symmetrical patterns, e.g. having a rotational symmetry of less than 360 degrees.

It is preferred that the SAW scattering elements are formed at least partially within the piezoelectric layer. Accordingly, in the following discussion of SAW scattering elements, they are described with reference to the piezoelectric layer. However, it is noted here that the SAW scattering elements may instead be formed in a superstrate coupled to the piezoelectric layer, in which case the skilled person will understand that references to the piezoelectric layer can be replaced with references to the superstrate.

The SAW scattering elements may be elements that provide an interface capable of significant scattering of SAWs. Preferably, at the interface, there is a sharp change in elastic modulus (e.g. Young's modulus) "seen" by the SAWs. This can be achieved by forming each scattering element from a different material compared with the material of the piezoelectric layer, the different material typically having a different density compared with the material of the piezoelectric layer. For example, one or more of the scattering elements may be formed by a void at the piezoelectric layer surface. The void may be gas-filled, e.g. air-filled. Alternatively, the void may be filled with a different solid or liquid material compared with the material of the remainder of the piezoelectric layer. Filling the void with a contrasting (e.g. mechanically, structurally or functionally contrasting) solid material is desirable, because it allows the piezoelectric layer to be formed with a smooth surface, therefore allowing the droplet to move across the arrangement of scattering elements if required. The contrast in mechanical properties between the piezoelectric layer and the scattering elements may be changed in use, e.g. by the application of an external stimulus such as heat.

The scattering elements preferably intersect the surface of the piezoelectric layer. This is preferred since they are for scattering surface acoustic waves, which are predominantly surface phenomena. However, the scattering elements may extend to a non-zero depth in the piezoelectric layer. For example, they may extend at least 5% into the thickness of the piezoelectric layer. They may extend further than this, e.g. at least 10%, at least 20% or more into the thickness of the piezoelectric layer. In some circumstances, the scattering elements may extend through the entire thickness of the piezoelectric layer, although a depth of about half of the thickness of the piezoelectric layer is advantageous. The scattering elements may be pits in the piezoelectric layer. Alternatively, the scattering elements may be pillars upstanding from the piezoelectric layer surface.

Typically, the scattering elements are cylindrical (e.g. circular or oval cylindrical) in shape, or they may be prismatic or polygonal in shape. Alternatively, the scattering elements may be ridges or grooves in the piezoelectric layer. Such shapes may have a straight form, but may alternatively have a curved or angled form. As discussed above, a scattering element may take the form of a step in the piezoelectric layer surface.

Preferably, the manipulation surface includes at least one scattering zone and at least one sample manipulation zone. The SAW scattering elements may be arranged in the scattering zone, the scattering zone providing in use a different transmission, distribution and/or behaviour of surface acoustic waves compared with the sample manipulation zone.

The arrangement of the SAW scattering elements preferably provides, in effect, a phononic crystal structure that interacts with or affects the acoustic field at the manipulation surface. The scattering elements may provide various effects on the SAWs. In addition to the concentration effect mentioned above, the scattering elements may reflect (or partially reflect) the SAWs, and/or may diffract (or partially diffract) the SAWs, and/or may refract (or partially refract) the SAWs. Additionally or alternatively, there may be set up standing interference patterns of SAWs at the substrate surface. For example, the scattering element arrangement preferably effectively concentrates the SAWs in one region of the manipulation surface.

The scattering elements may have an element-to-element nearest neighbour spacing of at least 10 µm. This is suitable for SAWs in the MHz region (e.g. of frequency of around 100

MHz). More preferably, this spacing is at least 20 µm, at least 40 µm, at least 60 µm, at least 80 µm, or at least 100 µm. This spacing may be at most 5 mm (corresponding to relatively low frequency SAWs), more preferably at most 4 mm, more preferably at most 3 mm, more preferably at most 2 mm, more preferably at most 1 mm, more preferably at most 0.9 mm, at most 0.8 mm, at most 0.7 mm, at most 0.6 mm. For example, an element-to-element nearest neighbour spacing in the range 200-500 µm has been shown to be suitable. For higher frequencies, e.g. in the GHz range, smaller spacings are contemplated, e.g. in the range down to at least 1 µm.

Preferably, the manipulation of the fluid sample includes one or more of: movement of the sample along the sample manipulation zone; splitting of the sample; combining two or more samples; atomisation of the sample from the sample manipulation zone; heating of the sample; concentration of species in the sample; mixing of the sample; sorting fluid samples; sorting particles or cells within fluid samples.

Preferably, the manipulation of the droplet includes movement of the droplet along the sample manipulation zone. The sample manipulation zone may define a track for droplet movement. Additionally or alternatively, the manipulation of the droplet includes atomisation of the droplet from the sample manipulation zone.

When two or more droplets are manipulated using the apparatus, it is possible for the droplets to have different characteristics, e.g. different composition, different temperature, different viscosity, different entrained species (e.g. biological material, particles, solute, etc.). In this case, the manipulation of the droplets may include mixing of the droplets. Mixing may be achieved by moving the droplets along corresponding tracks to a mixing zone, where the droplets meet and are mixed to form one or more mixed droplets. The mixed droplet may then be moved onwardly from the mixing zone along a further track.

The operation of the apparatus may allow splitting of a droplet into two or more daughter droplets. Each daughter droplet may be conveyed onwardly along respective tracks or along the same track.

The track here defines the intended path for the droplet. The track may be straight, curved, bent, angled, forked, split or joined with another track. The track may be provided with a hydrophilic surface, typically bordered by one or more hydrophobic areas. In the case of an aqueous sample, this can assist with confining the droplet to the track.

The operation of the apparatus may furthermore allow concentration of a species in one or more droplets. This can be achieved, for example, by allowing the SAWs to interact with the droplet to heat the droplet, thereby accelerating the evaporation of solvent. Alternatively, the acoustic field may be controlled by an appropriate arrangement of scattering elements and suitable control of the driving signal to the transducers to drive the species preferentially towards one part of the droplet. For example, an acoustic cavity can be set up in order to provide a standing wave arrangement, which has been shown to provide particle concentration [Shi, J. et al., 2008. Focusing microparticles in a microfluidic channel with standing surface acoustic waves (SSAW). Lab on a Chip, 8(2), 221-223]. Heating without deliberately promoting evaporation is of interest in its own right, e.g. for PCR (polymerase chain reaction) applications for DNA or RNA.

The operation of the apparatus may also allow concentration of a species in one or more droplets by inducing streaming within the droplet, which streaming concentrates species at a location within the droplet. In the context of the present invention, this type of concentration may be referred to as "centrifugation" (even though it may not represent true centrifugation) since it produces a "pellet"-like deposit of species within the "supernatant" of the liquid droplet, and can separate particles in the fluid sample from the fluid phase. This concentration can be achieved by providing SAWs to the droplet to induce rotational streaming in the droplet, for example by providing SAWs to the droplet asymmetrically (i.e. such that the distribution of SAWs is asymmetric with respect to the centre of the droplet footprint). Preferably, the manipulation surface includes an arrangement of SAW scattering elements arranged to scatter SAWs provided at the manipulation surface into a configuration for inducing rotational streaming in the droplet. The droplet may be positioned on the manipulation surface at a position relative to the SAW scattering elements such that SAWs are partially scattered by the scattering elements and the droplet receives SAWs distributed asymmetrically with respect to the centre of the droplet footprint.

The sample manipulation zone may include at least one droplet sensor. The droplet sensor may be operable to detect the presence of a droplet. One or more droplet sensors may be arranged sequentially in order to detect the presence of a droplet along a track. In this way, the apparatus may be operable to detect the movement of a droplet along a track. Droplet sensing can be carried out, for example, using echo location as discussed by Renaudin et al [Renaudin, A. et al., 2009. Monitoring SAW-actuated microdroplets in view of biological applications. Sensors and Actuators B: Chemical, 138(1), 374-382]. Alternatively, droplet sensing can be carried out using imaging means such as a camera.

The substrate may have more than one sample manipulation zone. A series of sample manipulation zones may be provided, in communication with each other, the droplet being transferred from one sample manipulation zone to the next. As an example, a first sample manipulation zone may provide droplet movement from a first location to a second location. A second sample manipulation zone may provide a mixing stage where the droplet, received from the first sample manipulation zone, is mixed (e.g. with another droplet or simply mixed to mix its own contents), and may provide onwards movement of the mixed droplet. A third sample manipulation zone may provide an atomisation stage where the mixed droplet, received from the second sample manipulation zone, is atomised. This atomisation stage may be for analysis of the droplet, e.g. using a mass spectrometer. In this case, suitable arrangements of scattering elements are provided for each zone, to affect the acoustic field in each zone in a suitable way to promote the required functionality of each zone. Thus, more generally, the apparatus may have a series of sample manipulation zones, in communication with each other, the fluid sample being transferrable from one sample manipulation zone to the next. It is preferred that corresponding scattering zones are provided in order to achieve transfer of the fluid sample.

The layer of piezoelectric material may be a sheet (e.g. a self-supporting sheet) of piezoelectric material. A suitable material is $LiNbO_3$. Other ferroelectric materials may be used, e.g. PZT, $BaTiO_3$, $SbTiO_3$ or ZnO. Still further, materials such as $SiO_2$ (quartz), AlN, $LiTaO_3$, $Al_2O_3$ GaAs, SiC or polyvinylidene fluoride (PVDF) may be used.

In some applications, it is strongly preferred that the fluid sample is shielded from external contamination. Furthermore, in the same or in other applications, it is preferred that the fluid sample is shielded from the user in order to protect the user. Accordingly, preferably the apparatus includes at least one enclosed channel for the fluid sample, the channel being bounded on at least one side by the manipulation surface.

In some embodiments, the opposing side of the channel may be bounded by a passive encapsulation surface. A suitable surface may be provided by an encapsulation layer.

In other embodiments, two or more sides of the channel may be bounded by a manipulation surface, each manipulation surface being adapted to be provided with SAWs for interaction with the fluid sample in the channel. Each manipulation surface may have at least one SAW scattering element for affecting the transmission, distribution and/or behaviour of SAWs at the manipulation surface, as set out above.

For example, the apparatus may have:
a first piezoelectric layer and associated transducer electrode structure;
a first manipulation surface at which SAWs are provided from the first piezoelectric layer;
a second piezoelectric layer and associated transducer electrode structure; and
a second manipulation surface at which SAWs are provided from the second piezoelectric layer,
wherein the first and second manipulation surfaces define between them a channel for the fluid sample.

The channel may be bounded at its lateral sides in order to enclose the flow path of the fluid sample.

In this way, the apparatus can be provided in the form of a laminated structured device. This laminated structure allows the apparatus to be manufactured via mass processing techniques.

Providing the channel with manipulation surfaces on opposing sides increases the control over the manipulation of the fluid in the channel. One or both of the manipulation surfaces may include SAW scattering elements as set out above. The manipulation surfaces may have substantially the same arrangement of SAW scattering elements. These SAW scattering elements may be arranged substantially in register with each other, or they may be offset from each other. Alternatively, the manipulation surfaces may have different arrangements of SAW scattering elements, such as SAW scattering elements of different periodicity, different shape, etc. The different arrangements of SAW scattering elements may be offset from each other, or they may be located so as to oppose each other. The transducer electrode structures of the first and second piezoelectric layer can be driven by a common signal. However, it may be preferred to drive these electrodes via separate signals, in order to be able to provide careful control of the SAW distribution in the apparatus. Independent control of the electrodes may allow different manipulation processes to be applied to the sample. For example, locating sets of electrodes so that SAWs are provided along different directions in the apparatus allows vector control of the movement of the sample.

The apparatus may further include at least one sensor. The sensor may be located at the fluid manipulation surface. The sensor may be operable to sense, for example, temperature, conductivity and/or the presence or absence of a fluid sample.

The apparatus may include at least one heater. The heater may be operable to generate SAWs which, in turn, generate heat due to absorption by at least part of the apparatus. Additionally or alternatively, the heater may include a resistive heating element. This may be provided at the sample manipulation surface. Incorporating a heater into the apparatus allows the apparatus reliably to be used for PCR.

The apparatus may further include at least one reservoir. The at least one reservoir may be provided in the piezoelectric layer. Additionally or alternatively the at least one reservoir may be provided in an encapsulation layer (if present) of the device. Preferably, the reservoir is provided with an opening providing fluid communication with the manipulation surface. In this way, useful reagents can be stored in the reservoir and provided to the manipulation surface (and hence to the sample) during operation of the apparatus.

The apparatus may further include at least one aperture. For example, an aperture may be provided over the SAW scattering elements. This may allow the sample to escape from the apparatus. This is of particular utility where the SAW scattering elements cooperate to nebulise the sample, in which case the nebulised sample can escape from the apparatus via the aperture. The apparatus may then be used as a sample delivery apparatus for an analytical device such as a mass spectrometer.

Preferably, the piezoelectric layer is formed using a deposition process selected from the group consisting of: sputtering, screen printing, casting, doctor blading, dipcoating, solution deposition and electrophoresis.

In the case of solution deposition, the precursor may be heated (e.g. by microwave heating) in order to promote crystallization. This is explained, for example, in Yang et at (2009) [C. Yang et al., "Solution-processed flexible ZnO transparent thin-film transistors with a polymer gate dielectric fabricated by microwave heating," Nanotechnology, vol. 20, no. 46, p. 465201, 2009].

RF sputtering of piezoelectric material is disclosed in Pál et al (2009) [E. Pál, T. Seemann, V. Zöllmer, M. Busse, and I. Dékány, "Hybrid ZnO/polymer thin films prepared by RF magnetron sputtering," Colloid and Polymer Science, vol. 287, no. 4, pp. 481-485, 2009], e.g. onto a polymeric substrate. Sputtering onto other substrates is disclosed in Du et al (2007) [X. Y. Du et al., "ZnO film for application in surface acoustic wave device," Journal of Physics: Conference Series, vol. 76, p. 012035, 2007].

The piezoelectric layer may be in the form of a composite material. In that case, preferably particles of a piezoelectric material may be hold in a matrix material. Preferably, the matrix material is a polymer material. Conveniently, the matrix material can be a material that is photosensitive, e.g. a photoresist. This allows the composite material to be patterned very precisely to a desired shape. Complex patterns (e.g. arrays of SAW scattering elements in the form of a phononic structure) can then be formed in the composite material.

Preferably, the piezoelectric layer has a thickness of at least 1 µm. More preferably, the piezoelectric layer has a thickness of at least 2 µm, or at least 5 µm or at least 10 µm. The piezoelectric layer preferably has a thickness of not more than 500 µm, more preferably not more than 400 µm, more preferably not more than 300 µm, more preferably not more than 200 µm, more preferably not more than 100 µm.

It is considered by the inventors (without wishing to be limited by theory) that surface acoustic waves tend to at least partially refract into the fluid sample. This refraction is due to the fluid sample having, in general, a different speed of propagation for the SAWs compared with the substrate. This produces streaming in the fluid sample. It is considered that applying SAWs to a manipulation surface contacting a fluid sample can create a specific structure of pressure waves and shear stresses in the sample. These pressure waves and shear stresses can mechanically disrupt cells contained in the sample to effect cell lysis. It is considered that, in the preferred embodiments of the present invention, SAW-mediated cell lysis can achieve efficiencies above 95%, which is very favourable compared with known chemical and mechanical methods of cell lysis.

It is preferred that the fluid sample is a liquid sample containing cells (or at least one cell). Furthermore, it is preferred that the fluid sample is an aqueous liquid sample containing cells. In a preferred embodiment, the fluid sample consists of or comprises blood, and therefore contains blood cells. However, as mentioned above, it is possible for the sample to be solid or substantially solid. For example, the sample may contain only a small volume proportion of liquid. Suitable substantially solid samples include feces.

It is preferred that the fluid sample is in the form of a drop, e.g. a droplet such as a microfluidic droplet. However, other arrangements are possible for the fluid sample, e.g. a channel of fluid, or a fluid held in a chamber, in the form set out above. In the following discussion, the term "droplet" is used, but as discussed above, it is intended that the invention is not necessarily limited to the lysis of cells in droplets.

The volume of the droplet may be at least 1 picoliter. For example the volume of the droplet may be at least 10 picoliter, at least 100 picoliter or at least 500 picoliter. The volume of the droplet may be higher, e.g. at least 1 nanoliter, at least 10 nanoliter, at least 100 nanoliter or at least 500 nanoliter. Preferably the droplet is larger, e.g. at least 1 microliter, at least 2 microliter, at 5 microliter, at least 10 microliter, at least 15 microliter, at least 20 microliter, at least 25 microliter or at least 50 microliter. The preferred upper limit for the volume of the droplet is about 5 milliliter, more preferably about 1 milliliter, still more preferably about 0.1 milliliter.

Preferably, suitable droplets for cell lysis using the present invention have a volume in the range 0.1-100 microliter, or 1-50 microliter. More preferably, suitable droplets of volume 5-25 microliter are used.

The volume of the droplet may be adjusted according to the area of contact between the droplet and the manipulation surface. For example, the volume of the droplet may be adjusted to vary the contact angle (e.g. in the case where the droplet is confined to a particular fluid sample area—see below). Preferably, the contact angle (i.e. the included angle between the manipulation surface and the tangent to the droplet surface at the manipulation, measured in a plane containing the normal to the substrate surface) is not less than 65 degrees, not less than 75 degrees, not less than 85 degrees, or not less than 95 degrees. Preferably the contact angle is 65-115 degrees, or more preferably 95-115 degrees.

The manipulation surface may be provided with a fluid sample area in the form of a fluid sample pinning zone. Preferably the fluid sample pinning zone is provided in the form of a spot, for pinning a fluid sample droplet to the manipulation surface. Thus, the perimeter of the fluid sample pinning zone may delineate a fluid sample pinning line. Preferably, the fluid sample pinning zone is a hydrophilic area, for pinning an aqueous fluid sample to the manipulation surface. More preferably, the fluid sample pinning zone is a hydrophilic area in the form of a spot, for pinning an aqueous droplet to the manipulation surface. The hydrophilic area may be formed from e.g. lithium niobate ($LiNbO_3$), silicon (Si wafer), zinc oxide (ZnO), silicon oxide ($SiO_2$), glass, or plastics (polymers or copolymers, e.g. with a polyethylene glycol moiety, PEG). These may be further modified using a specific chemical process such as a silanisation (e.g. with aminopropyltriethoxysilane), poly-L-lysine, or PEG or a combination of processes. The hydrophilic area may be surrounded by a hydrophobic zone, which may be formed from e.g. silane such as 1H,1H,2H,2H-Perfluorooctyltriethoxysilane, octadecyltricholrosilane, or a Teflon-like coating (C4F8 deposition). The fluid sample pinning zone can also be formed by physical structures, for example the pinning zone may be formed as a well in the manipulation surface. The pinning zone may be formed by a wall or walls that define the perimeter of the pinning zone, which wall or walls may be formed from pillars, or from scattering elements (i.e. elements that contribute to a phononic property of the substrate surface) for example pillars that act as scattering elements. The fluid sample pinning zone is not essential for cell lysis, but it may prevent the droplet from moving when surface acoustic waves hit it at high powers and may facilitate adjustment of the area of contact between the fluid sample and the manipulation surface in order to vary the contact angle.

The fluid sample pinning zone preferably has a width or diameter of (or has a width or diameter in the range of up to) about 1 millimeter, about 2 millimeters, about 3 millimeters, about 4 millimeters, or about 5 millimeters.

The size (e.g. width, maximum allowed width, or diameter) and/or shape of the fluid sample pinning zone may be varied in order to vary the contact angle and surface tension properties at the fluid sample pinning line for a particular fluid sample volume, and thereby influence the propagation of the pressure wave from the incident SAW through the sample, such that a cell in the fluid sample is lysed.

The concentration of cells in the fluid sample may be adjusted in order to optimise cell lysis. Preferably the concentration is about 5 million cells/milliliter or less, about 3 million cells/milliliter or less, about 1 million cells/milliliter or less, about 500,000 cells/milliliter or less, or about 100,000 cells/milliliter or less.

The fluid sample may consist of or comprise a biological sample such as blood, saliva or urine. For example, the fluid sample may be whole blood. Preferably, the fluid sample is diluted blood, for example whole blood diluted in PBS. The dilution of the sample expressed as sample:diluent may be about 1:10 or greater (dilution factor 0.1 or lower), about 1:25 or greater (dilution factor 0.05 or lower), 1:50 or greater (dilution factor 0.02 or lower), or 1:100 or greater (dilution factor 0.01 or lower).

The present inventors have shown that the necessary conditions for cell lysis can be achieved using a variety of different SAW platforms and configurations. The present invention thus provides multiple routes to integrate preparation of biological samples in a complete assay on a microchip.

Without wishing to be bound by theory, the present inventors believe that, e.g. by focussing the acoustic power of SAWs at a position within a fluid sample containing cells, it is possible to create acoustic pressure fields and streaming within the sample that lyse the cells.

Preferably, surface acoustic waves are provided to the substrate surface contacting a droplet such that rotational streaming is induced in the fluid sample droplet. Without wishing to be bound by theory, the present inventors believe that rotational streaming results in the creation of one or more vortexes in the sample, and, under appropriate conditions, the pressures and shear stresses near the centre of a vortex are sufficient to lyse cells.

Rotational streaming may be induced in the droplet by providing the SAWs to the droplet in an asymmetrical manner in relation to the droplet, that is, providing the SAWs such that they hit the droplet asymmetrically. By causing an asymmetry in the SAWs with respect to the droplet, angular momentum and hence rotation is induced in the droplet. The term "asymmetrical" here refers to the distribution of the SAWs with respect to the droplet. One example of a suitable asymmetric distribution is provided where the SAW path incompletely overlaps with the footprint of the droplet on the manipulation surface, as described below.

The term SAW "beam" is used herein to define the emission train, or path, of surface acoustic waves provided at a substrate surface. The terms SAW beam, SAW emission train and SAW path are used herein interchangeably. The width of the SAW beam is notionally defined by the aperture of the transducer that emits the SAW beam. The aperture of a transducer is the part of the transducer that resonates to emit a SAW beam. In the context of the present invention, the lateral width of an aperture of a transducer is taken to define the lateral width of the SAW beam. For a parallel electrode interdigitated transducer, the aperture is typically the lateral expanse of the region of overlap between the electrode fingers (see w, FIG. 6). In this context, the edge of the SAW beam is laterally aligned with the edge of the IDT aperture along the direction of propagation of the SAWs. Whilst it is understood that in reality the edge of a SAW beam is not necessarily sharp, as explained below, for the purposes of the present invention, an edge of a SAW beam is defined as a notional longitudinal edge in lateral alignment with an edge of a transducer aperture. It is understood that the amplitude of the SAWs decreases with lateral distance from the edge of the SAW beam.

For a droplet contacting a manipulation surface to form a droplet footprint on the manipulation surface, rotational streaming may be induced in the droplet by providing SAWs at the substrate surface such that the SAW path only partially overlaps with the droplet footprint (at least in terms of the position of the notional edge of the SAW path with respect to the droplet). A droplet may have an approximately circular footprint, for example, and the SAW path may overlap with a segment of the footprint. A SAW path may overlap with about 10-90% of the droplet footprint. A SAW may be provided at the substrate surface such that the SAW path overlaps with about 50% of the droplet footprint, wherein the edge of the SAW path passes near the centre of the droplet.

Preferably, SAWs are provided at the manipulation surface by a transducer arrangement (e.g. a parallel electrode interdigital transducer) and the droplet is positioned on the manipulation surface at a position relative to the transducer arrangement such that the droplet receives SAWS distributed asymmetrically with respect to the centre of the droplet. For example, the droplet may be longitudinally displaced from but laterally aligned with respect to an edge of an aperture of an interdigital transducer (IDT) arrangement, wherein said edge of the aperture defines an edge of a SAWs emission train, such that the droplet is only partly located on the SAWs emission train provided by the IDT arrangement.

Additionally or alternatively, SAWs are provided at the manipulation surface by a transducer arrangement for which it is possible to control the lateral position of the SAWs emission train with respect to the transducer arrangement, for example by tuning the input frequency. In this embodiment, the droplet is placed on the manipulation surface and the lateral position of the SAWs emission train is tuned to a position on the manipulation surface such that the droplet receives SAWs distributed asymmetrically with respect to the centre of the droplet. The transducer arrangement may be a slanted IDT (also known as a slanted finger IDT) for which the lateral position of the SAWs emission train can be adjusted by varying the input frequency. An advantage of this embodiment is that it does not require precise positioning of the droplet on the substrate surface, since the lateral position of the SAWs emission train on the manipulation surface can be adjusted relative to that of the droplet. In the case of a slanted IDT, it is more difficult to define a notional edge of the SAWs emission train, since the amplitude of the SAWs across the emission train may decrease relatively gradually laterally from a central maximum of the emission train. In this case, the notional edge of the SAWs emission train can be considered to be the lateral position at full width half maximum of the SAWs amplitude distribution in the lateral direction.

It is not necessarily essential that the SAWs induce rotational streaming in order for cell lysis to be achieved. The pressure fields necessary for cell lysis may be induced using a wide range of SAW geometries, encompassing standing waves as well. The inventors believe that it is possible to use SAWs to lyse cells within a droplet, without necessarily creating rotational streaming or a vortex within the droplet, by focusing acoustic power at a position within the droplet.

Furthermore, it is not necessarily essential that the SAWs are provided to the droplet asymmetrically in order for rotational streaming to be achieved. Cell lysis can be achieved when multiple vortexes are formed in configurations where the SAW hits the droplet in a more symmetrical manner. For example, it is possible to design a fluidics apparatus to achieve reproducible multiple vortexes in fluid sample droplets, for example by including arrangements of scattering elements or phononic structures (also known as phononic lattices or phononic crystals) on the manipulation surface.

Disposable apparatus are especially useful for the analysis of biological samples. Disposable apparatus may reduce sample cross contamination in point-of-care diagnostic applications, and may reduce contamination of samples with species that may compromise the molecule of interest (e.g. RNAse, where messenger RNA is the molecule of interest).

For the purposes of the present invention, the input power of the surface acoustic wave may be between −19 dBm and 0 dBM, between around −14 dBm and around −6 dBm, around −14 dBm or higher, around −12 dBm or higher, around −10 dBm or higher, around −9 dBm or higher, around −8 dBm, around −7 dBm, or around −6 dBm or higher.

For the devices described herein in relation to embodiments of the present invention, the related power arriving at the IDT can be obtained using the table below. The power arriving at the IDT is calculated by converting the input power value, expressed in dBm, to a value expressed in W and multiplying the W value by 5000 (the amplification by the amplifier).

| dBm | W |
| --- | --- |
| 0 | 5 |
| −1 | 3.971641 |
| −2 | 3.154787 |
| −3 | 2.505936 |
| −4 | 1.990536 |
| −5 | 1.581139 |
| −6 | 1.255943 |
| −7 | 0.997631 |
| −8 | 0.792447 |
| −9 | 0.629463 |
| −10 | 0.5 |
| −11 | 0.397164 |
| −12 | 0.315479 |
| −13 | 0.250594 |
| −14 | 0.199054 |
| −15 | 0.158114 |
| −16 | 0.125594 |
| −17 | 0.099763 |
| −18 | 0.079245 |
| −19 | 0.062946 |

The present inventors found that for a particular cell type at a particular concentration, if a relatively low power is used then cells are concentrated in the centre of the droplet without lysing, and if a relatively high power is used then cell lysis is achieved. Without wishing to be bound by theory, the present inventors believe that such an increase in power increases the pressures and shear stresses in the droplet such that cells in the droplet are crushed and lyse. Accordingly, it is preferred to provide SAWs to a droplet containing cells, and to progressively increase the input power, thereby progressively increasing the power of the SAWs, until cell lysis is achieved. This way, for a given set of conditions, cells can be lysed using the minimum power necessary to achieve cell lysis under those conditions. For example, cells of a particular type can be lysed using the minimum power necessary to achieve cell lysis for that cell type.

The frequency of the surface acoustic wave may be in the range of about 10 kHz to about 1 GHz, preferably about 1 MHz to about 100 MHz, more preferably about 5 MHz to about 50 MHz, more preferably about 5 MHz to about 20 MHz, more preferably about 15 MHz to about 5 MHz, more preferably between about 13 MHz and about 9 MHz. The frequency of the surface acoustic wave may be about 12 MHz, about 11 MHz, about 10 MHz, or about 9 MHz.

For the purposes of the present invention, the SAW may be provided at the substrate surface for about 0.1 seconds or longer. The SAW may be provided for about 0.1-60 seconds. Preferably, the SAW is provided for about 1 second or less, about 2 seconds or less, or about 3, 4, 5, 6, 7, 8, 9, 10, 15, 20, 25, 30, or 35 seconds or less.

The present inventors found that cell lysis efficiency is affected by several factors, including the surface tension of the droplet, the contact angle of the droplet on the substrate surface, the concentration of cells in the droplet, power of the SAW and the amount of time for which the SAW is provided to the droplet. The optimum combination of values for each factor may depend on cell type. The skilled person, by adjusting these variables in combination or in isolation, based on the teaching provided herein, is able to provide conditions in which cell lysis can be achieved.

The term cell is used herein to refer to any type of cell, including eukaryotic and prokaryotic cells. In the context of the present invention, a cell is preferably a eukaryotic cell. A cell may be an animal cell, for example a mammalian cell (e.g. a blood cell, such as an erythrocyte). A cell may be that of a unicellular organism, (e.g. a trypanosome), which may be a protozoan or a protist. In some embodiments, the cell is a cell of a pathogen, for example a pathogenic protozoan, protist, or bacterium. A cell may have a cell wall, or may be wall-less (i.e. without a cell wall).

A fluid sample may contain a mixture of cells or cell types. The present inventors have found that the minimum power sufficient to lyse cells may vary depending on cell type. For example, under particular conditions (e.g. cell concentration, droplet contact angle) a specific power may sufficient to lyse cells of a first type, but insufficient to lyse cells of a second type. Under such conditions, if a SAW of that specific power is applied to a droplet containing a mixture of cells of the first and second type, cell lysis will be achieved for the cells of the first type but not cells of the second type. Accordingly, SAWs may be applied to a fluid sample containing a mixture of cell types in order to differentially lyse cells of different types. Different cell "type" may mean different taxonomic groups, for example different domains (eukaryotic cell type is different to prokaryotic cell type), kingdoms (e.g. animal cell type is different from fungal cell type), different physical or physiological types (e.g. a leukocyte is a different cell type from an erythrocyte). In particular, different cell types are cells that are differentially lysable (e.g. a first cell type is more easily lysed than a second cell type, that is, under a given set of experimental conditions, the lowest power necessary to achieve cell lysis for the first cell type is lower than the lowest power necessary to achieve cell lysis for the second cell type).

The term cell lysis is used herein to refer to any type of cell disruption. In particular, cell lysis is used to refer to cell disruption that results in release of intracellular molecules to the extracellular milieu, for example by rupture of the plasma membrane. Cell lysis encompasses rupture of the plasma membrane, and may encompass rupture of intracellular compartment (e.g. organelle) membranes such as the nuclear envelope and mitochondrial outer and inner membranes. Cell lysis is typically a complete and irreversible rupture of the plasma membrane, resulting in cell death. In the context of the present invention, however, cell lysis may encompass cell membrane poration, where the plasma membrane is incompletely ruptured (i.e. the plasma membrane temporarily and reversibly ruptures). Such poration may improve certain assays such as ELISA, in a similar way to that described in Borthwick et al [Kathryn A. J. Borthwick, Tracey E. Love, Martin B. McDonnell and W. Terence Coakley, Improvement of Immunodetection of Bacterial Spore Antigen by Ultrasonic Cavitation, Anal. Chem. 2005, 77, 7242-7245].

The term intracellular molecule, or intracellular molecule of interest includes macromolecules (protein, DNA, lipid, polysaccharide) small molecules (e.g. ATP, ADP. cAMP, glutathione, amino acids, oligosaccharides, monosaccharides) including metabolites and signalling molecules. The term intracellular molecule encompasses any molecule having an intracellular moiety of interest (e.g. a transmembrane protein). A molecule of interest is compromised if the structure of the molecule becomes significantly different from its native structure or intracellular structure, for example such that the molecule less amenable to analysis (e.g. an epitope required for immunological analysis is no longer present or has become immunologically inaccessible). The term "compromised" as used herein encompasses denaturation (e.g of a protein of interest) and degradation (e.g. hydrolysis of a polynucleotide, polypeptide or polysaccharide of interest).

Further optional features of the invention are set out below.

BRIEF DESCRIPTION OF THE DRAWINGS

FIG. 4 shows a droplet on a plain silicon surface without SAW scattering elements. FIG. 5 shows a droplet on a superstrate having an arrangement of SAW scattering elements.

FIGS. 8-11 show a series of consecutive frames from micrographic video footage of the operation of a fluid manipulation apparatus. These images clearly show that acoustic energy is being focused and reflected.

FIGS. 18-25 illustrate preferred embodiments of fluidics apparatus according to the present invention.

FIGS. 38 and 39 illustrate the effect of different operation frequencies on SAW distribution at a sample manipulation surface.

FIG. 40 shows a plot of temperature of a sample against applied power.

FIG. 41 shows the effect of temperature cycling by controlling the applied power.

FIGS. 42-50 illustrate the different formats for the sample manipulation surface in order to control temperature by controlled absorption of SAWs.

FIG. 51 shows a schematic plan view of a SU-8 layer formed on a glass substrate, with an opening located in order to allow a transducer (not shown) to couple to the glass substrate, a phononic reflector being formed in the SU-8 layer as a square lattice array of holes in the SU-8 layer.

FIG. 52 shows a plot of surface displacement (measured by a vibrometeter) along line 1-2 in FIG. 51.

FIG. 53 shows a microscopic image of a droplet containing particles, being subjected to standing SAWs, causing the particles to aggregate in concentric rings.

FIGS. 54-56 show sequential microscopic images of the centrifugation of particles in a droplet, due to the application of SAWs (from the right in the images) and the shadowing effect of a phononic structure (square array of SU-8 pillars on a glass substrate).

DETAILED DESCRIPTION OF THE PREFERRED EMBODIMENTS, FURTHER OPTIONAL FEATURES

Further Background and General Technical Considerations

It is known that microfluidic technologies can enable the precise control of the delivery of reagents, drugs and metabolites to single cells or to groups of cells. Such methods can be used for new medicines discovery, or to deliver reagents and samples in diagnostic technologies.

Despite such rapid advances in microfluidic, or so-called "Lab-on-a-Chip" technologies over the last decade, there have, however, been few new methods that have been developed to generate fluid flow within micro-scale channels. Most existing methods to create such flow rely on generating a pressure difference to drive the flow (in particular by the use of various forms of mechanical pumps). These methods all rely upon external interconnects from the chip to the pump, often making the process of connection one of the most challenging.

Other alternative methods currently in use involve the use of a phenomenon known as electrokinetic pumping (including electro-osmosis or dielectrophoresis) to drive the fluid under electrical control. In all cases, however, these techniques require the implementation of metallic planar transducers within the microchannels. Whilst these electrical connections to the chip result in fluid flow, the whole chip, including the transducers, is disposed of at the end of each assay. Thus, neither pressure driven mechanical pumping, nor electrokinetics, afford the user with the ability to interrogate and move the fluid in a "non-contact" manner, at low cost.

The present inventors have developed new techniques for droplet manipulation in the microfluidic regime. These techniques are based upon the use of surface acoustic waves (SAWS) generated on a piezoelectric device, such as a device based on lithium niobate, $LiNbO_3$.

A Raleigh wave is a coupled compressional-shear system where the longitudinal and the transverse motion are out of phase by 90°. The present inventors have demonstrated that it is possible to propagate such longitudinal Raleigh waves (an example of SAWs) from the piezoelectric device, through a coupling medium (which can, for example, be water or an oil) into a thin disposable microfluidic chip substrate formed of plastic, glass or other suitable material. Surprisingly, the waves carry sufficient energy to subsequently drive the fluids on the disposable substrate. Although the $LiNbO_3$ piezoelectric device is, itself, relatively expensive, in this format it is a re-usable platform, and it is only the substrate that is disposed of after a (typically single) use. The only physical contact for actuation of the droplet is through the medium between the $LiNbO_3$ and the disposable chip. The inventors have further found that it is possible to use the surface of the piezoelectric device itself as the sample manipulation surface, and to arrange suitable SAW scattering elements at the sample manipulation surface. The advantage of this approach is that the coupling between the transducer and the sample manipulation surface is assured and the alignment between the transducer and the sample manipulation surface is fixed during manufacture of the apparatus.

When Raleigh waves are propagated from a piezoelectric device to a substrate (e.g. a thin chip) coupled to the surface of the piezoelectric device, the resultant acoustic waves in the substrate may be described as Lamb waves. Raleigh waves and Lamb waves are types of surface acoustic waves. The term surface acoustic wave (SAW) is used herein to describe both Raleigh waves and Lamb waves unless indicated otherwise.

The functionality of the platform can, be readily extended beyond simple pumping of fluids or droplets. For example, by microfabricating multiple SAW transducers on the piezoelectric device, and through the subsequent differential actuation of these transducers, it is possible to manipulate droplets in a variety of different directions (linear, orthogonal or at any angle between). If necessary, by combining different relative components of wave generation from orthogonal actuators, it is possible to enable splitting and recombination of droplets.

By suitable control of the distribution of SAWs with respect to the sample, it is possible to lyse cells on-chip, or to atomise samples such that they can be transported off-chip. One particular application is the creation of plumes of atomised samples, which can be captured in ion-funnels to provide an innovative interface between low volume (e.g. single cell) biology and mass spectrometry. Other examples of the applications of the device involve the selective concentration of particles with respect to their size or mass (i.e. their fractionation). This can underpin diagnostic applications in separating vesicles, cells and micro-organisms.

Phononic Structures

Figure 1:
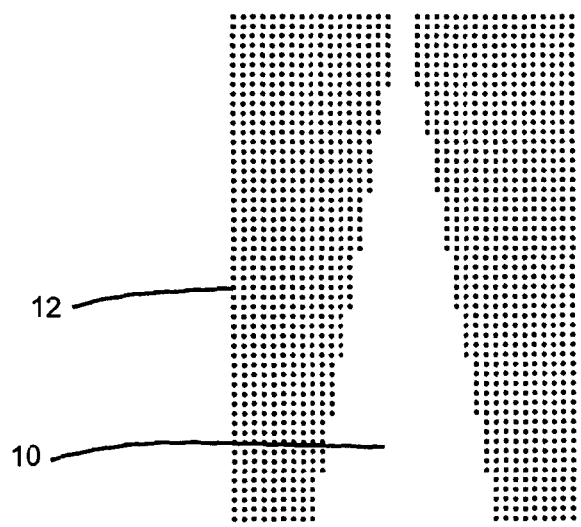
FIG. 1 shows a schematic plan view of a typical manipulation surface format suitable for use with the present invention, showing a "funnel" type sample manipulation zone.

FIG. 1 shows a schematic example of a sample manipulation surface in plan view. The surface typically has a length of 20 mm and a width of 14 mm. The example of FIG. 1 is a funnel design, in which the sample manipulation zone 10 is bounded by a boundary zone 12. The boundary zone includes a phononic bandgap structure of holes formed in the surface. The holes are arranged in a two dimensional square lattice pattern. In this example, each hole has a radius of 176 μm. In this example, the spacing between the centres of adjacent holes is 374 μm.

Figure 2:
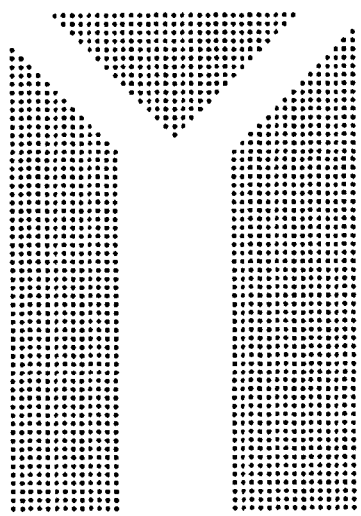
FIG. 2 shows a schematic plan view of another typical manipulation surface format suitable for use with the present invention, showing a "waveguide" type sample manipulation zone.

FIG. 2 is similar to FIG. 1, except that the design is a waveguide design.

Figure 3:
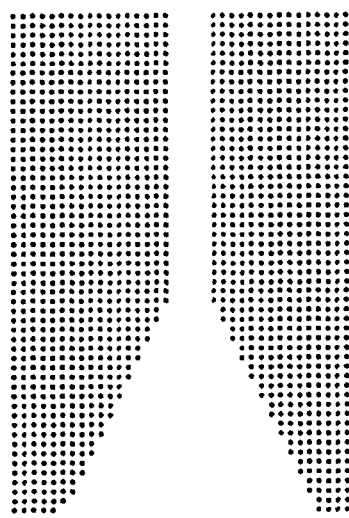
FIG. 3 shows a schematic plan view of another typical manipulation surface format suitable for use with the present invention, showing a "combination" type sample manipulation zone.

FIG. 3 is similar to FIG. 1, except that the design is a combination design.

In preferred embodiments of the invention, the sample manipulation surface shown in FIGS. 1-3 is a surface of a piezoelectric layer. After manufacture of the layer, the SAW scattering elements can be formed by coating the surface with a suitable photoresist and a pattern transferred into the resist using photolithography. The pattern may consist of a square array of circular holes arranged to provide a funnel, a waveguide with split or combination of funnel and waveguide, as shown in FIGS. 1-3, respectively.

The photoresist pattern can be used as a dry etched mask where the holes are etched to a depth of approximately 230 μm or, more generally, a depth equivalent to about half the thickness of the piezoelectric layer. The piezoelectric layer may then be cleaned (e.g. in acetone). The piezoelectric layer may then be cleaned again using an oxygen plasma treatment and then immersed in a solution of heptane and a tri-chloro-tri-deca-fluoro-octylsilane in order to give a hydrophobic surface, contact angle >65°.

A transducer electrode structure is arranged at the piezoelectric layer, e.g. on the same side of the piezoelectric layer as the SAW scattering elements (but other configurations are possible—see later). The combination the electrode structure and the piezoelectric layer is referred to as an interdigitated transducer (IDT). In some test experiments upon which the present work was founded, a suitable IDT was resonant at a frequency of 6.18 MHz and SAWs at this frequency were used for the tests. A programmable signal generator was used to provide an input of 6.18 MHz with amplitude of −10 dBm (1 W) pulsed at 50 Hz to an amplifier with 40 dB gain to present approximately 10 dBm (1 W) to the IDT.

In order to test mobility and atomisation, the droplet size was about 2 μL.

During testing, each of the structures shown in FIGS. 1-3 influenced the movement of the water droplets on the sample manipulation surface. The structure that appears to function most efficiently is the funnel (FIG. 1) and this is primarily thought to be due to the relative size of the structure, although the inventors do not wish to be bound by theory in this regard. The funnel efficiently moves and focuses the drops to the focal point of the funnel irrespective of the initial starting point of the droplet in the sample manipulation zone.

Although the test structures can be used multiple times their efficacy decreased with usage, as it can be difficult to adequately clean dried droplet stains from the exposed sample manipulation surface. This suggests that the apparatus should, where possible, should be used only once and then disposed of. Thus, it is strongly preferred that the apparatus can be manufactured in a manner than is efficient enough to allow disposal of the apparatus in this manner.

The waveguide structure (FIG. 2) provides guiding of the water droplets and reduces or eliminates wander of the droplet trajectory on the sample manipulation surface that would be observed without the border zone. No splitting of droplets is typically observed although movement into either waveguide split may be observed.

The combination structure (FIG. 3) provides focusing of droplets to the waveguide structure and transit along the structure may also be observed.

Atomisation of water droplets can be achieved on all the structures shown in FIGS. 1-3. This is discussed in more detail below.

Figure 4:
FIGS. 4 and 5 show micrographic images from a video sequence captured on a droplet, viewed from the side, on superstrates coupled to a piezoelectric transducer.
Figure 5:

FIGS. 4 and 5 show micrographic images from a video sequence captured on a droplet, viewed from the side, on superstrates removably coupled to a piezoelectric device. FIG. 4 shows a droplet on a plain silicon surface without a border zone. FIG. 5 shows a droplet on a substrate having a border zone with a phononic band gap structure similar to that described above. The image in each case is taken approximately 250 microsecs after the surface acoustic wave meets the droplet. As can be seen, more energy is transferred to the droplet in FIG. 5 than in FIG. 4. Each droplet has a volume of 1 μL. The power used in these experiments was 0 dBm input which supplied 5 W at the IDT. The excitation frequency was 9.56 MHz. The dimensions of the substrates were 2 cm by 1.5 cm. The amount of coupling fluid between the piezoelectric device and the superstrate was reduced to 4 μL—this provided a layer of approximately 13 μm thick. The superstrates were placed in the same position and were of the same thickness (450 μm).

Further details are set out below.

Figure 6:
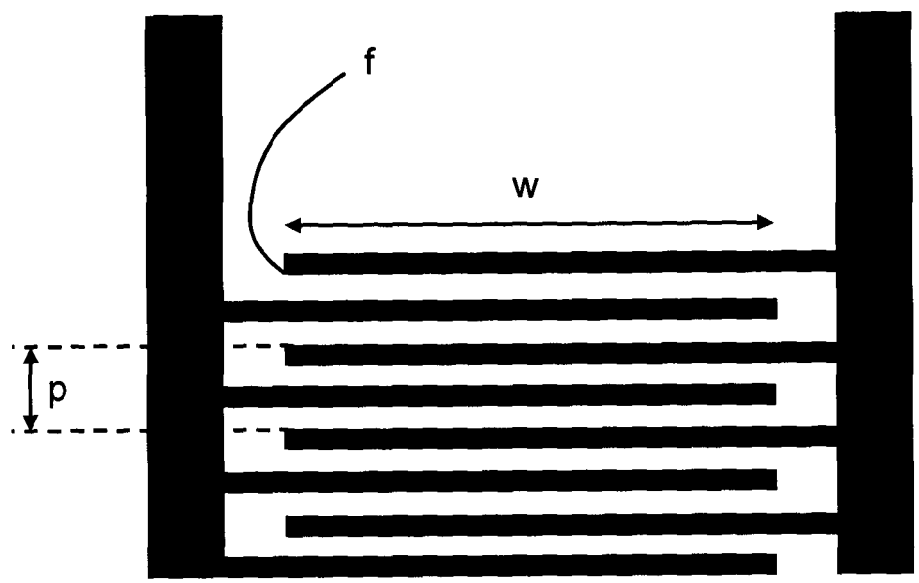
FIG. 6 shows a plan view of a transducer electrode structure for use with an embodiment of the invention. The electrode overlap w is 15 mm, the finger width for each electrode is 170 μm and the finger pitch p is 330 μm.

Transducer electrode structures may be formed on the piezoelectric layer, each having 20 pairs of electrode "fingers" to form interdigitated transducers (IDT). The electrode "fingers" were located with approximately 330 μm pitch p, 180 μm finger width f, with 15 mm aperture w (overlap), see FIG. 6. The direction of overlap of the fingers can be considered to be a transverse direction of the IDT. The electrodes may be patterned using a lift off process where after photolithography, using acetate masks, a 20 nm adhesion layer of titanium is deposited prior to 100 nm of gold onto the wafer, lift off is then carried out in a beaker with acetone to produce the IDT electrodes for the apparatus.

An Agilent MXG Analog Signal Generator N5181A 250 KHz 1 GHz, in conjunction with a Mini Circuits ZHL-5W-1, 5-500 MHz amplifier, can be used to power the SAW device. The amplifier may be powered by a TTi EX354D Dual Power Supply 280 W which is capable of supplying 3A and ±24V DC. Approximately 1 W of power may be applied to the IDT. The driving signal for the SAW device can be pulsed for 20 ms every 100 ms, to avoid excess heating (unless excess heating is wanted, e.g. to carry out PCR—see below). Droplets can be imaged at 62 frames per second using a high speed camera (Red Lake M3), allowing the capture of atomisation from single pulses to be visualized, when the surface acoustic waves travel through the droplet.

Figure 7:
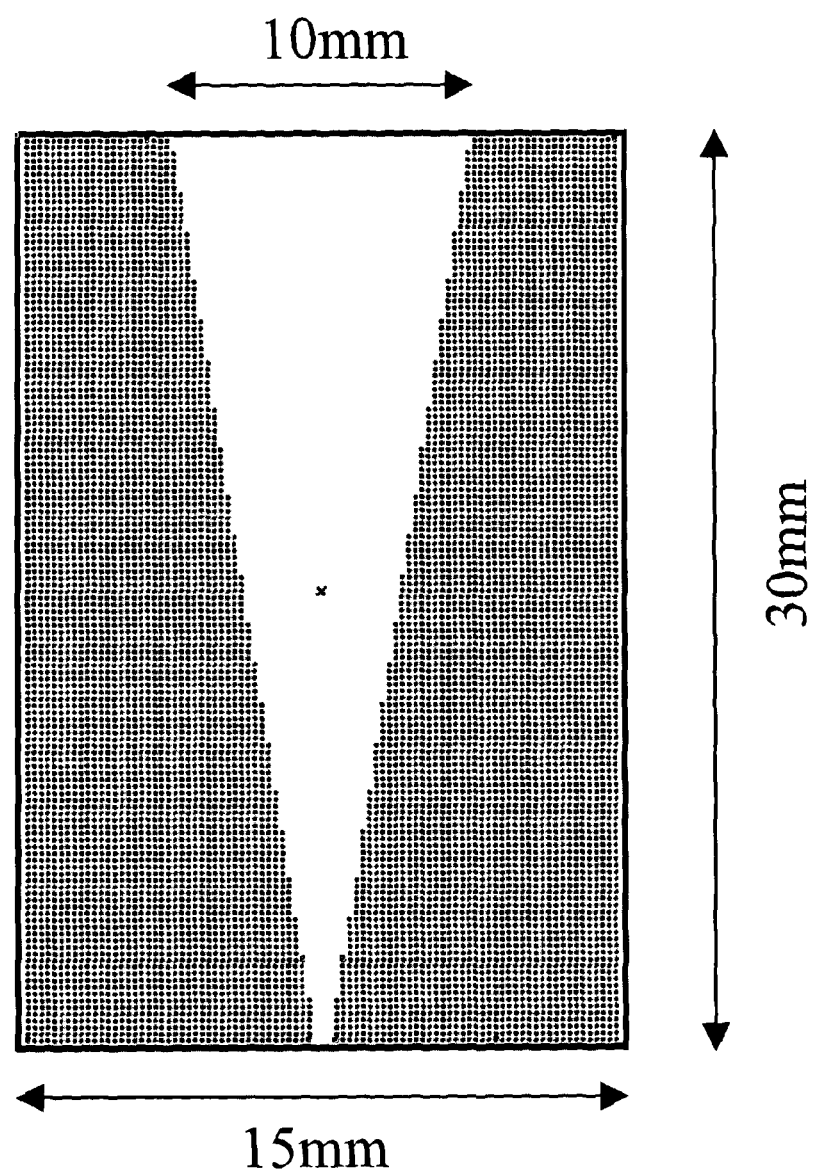
FIG. 7 shows a schematic plan view of a manipulation surface suitable for use in an embodiment of the invention, including typical (but non-limiting) dimensions.

FIG. 7 shows a schematic plan view of the configuration of a manipulation surface for use with an embodiment of the invention. The dimension of the cone patterned surface is approximately 15 mm by 30 mm. The aperture for the cone is 10 mm and the apex is approximately 0.57 mm (corresponding to two holes missing).

In order to illustrate atomisation, two 1 µL drops of deionised water can be used, one at the apex of the cone, the other approximately 10 mm away from the apex.

The phononic structure in the border zone consists of a square array of holes etched into the surface, to a depth about half way through the piezoelectric layer. This regular perturbation in the Young's modulus of the material provides the material with a frequency dependent acoustic transmission or reflection property.

Surface plots of the acoustic field intensity of a phononic cone structure illustrating the intensity at a frequency of 11.36 MHz and at a frequency of 11.56 MHz are shown in FIGS. 8 and 9 of WO2011/023949. These plots together show the effectiveness of the phononic structure to confine the acoustic field depending on the frequency used: a change of 200 KHz from 11.36 MHz to 11.56 MHz can provide a 3 dB change in intensity.

The present inventors aimed to find the resonant frequency of the IDT to obtain the most efficient frequency to atomise the drops from the manipulation surface. In this case 12.85 MHz is found to be the resonant frequency for the IDT and droplet atomisation from the manipulation surface. However, this frequency of operation may not provide suitable operation of the phononic structures in the border zone. It is observed that by reducing the excitation frequency for the IDT down to 12.64 MHz a dramatic increase in atomisation is observed on the surfaces with phononic structures. The increase in substrate activity is more than enough to compensate for any decrease in IDT acoustic conductance (the amount of electrical power that can be transformed into mechanical power).

The wavelength of the SAW depends on the pitch of an IDT. However, the observed change in acoustic response of the phononic structure would indicate a change in the wavelength of the SAW and hence variation in the pitch of the intedigitated electrodes. This variation can be a consequence of using acetate masks for prototyping. Such masks may posses a variation in the electrode thickness that might normally be thought to be insignificant, but it seems that they may indeed be significant. So in effect the inventors use an IDT with a range of pitches allowing a number of possible wavelengths to be radiated.

In an alternative embodiment, the transducer uses a slanted interdigitated electrode structure. This is then used as a tunable source of SAWs. By slanting the electrodes the inter-electrode distance changes with lateral position across the electrode structure. This arrangement can be modelled by an array of IDT's with differing inter electrode spacing. The position of the SAW depends on the excitation frequency used.

It is possible to design a device for use at a certain operating wavelength (frequency) but typically there are always some deviations from the design parameters due to manufacturing tolerances during fabrication. As shown in WO2011/023949, the phononic structures are highly frequency/wavelength dependent. Therefore, by varying the excitation frequency slightly away from the predicted operating frequency, it is possible to tune in to a useful operating regime where the SAW wavelength is shifted enough to allow the device to function substantially as designed.

Discussion of Apparatus with Piezoelectric Transducer and Separable Superstrate

It is preferred in the embodiments of the present invention that the sample manipulation surface is, for example, a surface of the piezoelectric layer on which the SAWs are generated and are propagated. However, the inventors have carried out detailed preliminary work relating to the use of a superstrate removably coupled to a single crystal piezoelectric transducer. This work is relevant to the preferred embodiments of the invention, because it shows the technical considerations necessary for the design and operation of the apparatus.

FIGS. 8-11 show a series of consecutive frames from video footage captured under a microscope of a fluid manipulation apparatus operating. These images clearly show that acoustic energy is being focused and reflected.

In FIGS. 8-11, two 1 μL droplets have been placed onto the manipulation surface. The first droplet is directly in the path of the second droplet, about 10 mm behind the first droplet. The second droplet should in effect "steal" some of the acoustic energy before the acoustic energy can reach the other first droplet. Despite this, atomisation was observed only for the first droplet, at the apex of the phononic cone. The length of the substrate in this case was 30 mm. The power used in this case was five times lower than in the experiments reported above.

Atomisation for 0.5 μL drops has been observed at 790 mW applied power.

FIG. 8 shows the first of a series of frames taken from a movie captured at 62 frames per second. This first image is just prior to an ultrasonic SAW pulse arriving at the droplets at about 4000 m/s. Approximately 1 W of power was applied to the IDT.

FIG. 9 shows the droplets irradiated by the SAWs with the second droplet clearly agitated but not atomising, whereas the first drop near the apex of the cone is atomising (or more correctly nebulising).

FIG. 10 shows a frame in which the 20 ms pulse has stopped but some free oscillation in the drops can be observed. It is interesting to note that the drop that was atomising was in the shadow of the second drop and would normally experience much less acoustic radiation as the second drop would absorb a significant amount of the Rayleigh wave energy.

In FIG. 11 the oscillations have stopped and only the plume expelled from the first drop can be seen. This illustrates the efficacy of the device.

The design, construction and investigation of the device shown in FIGS. 8-11 will now be described in more detail. Note that the device used in FIGS. 8-11 was a removable superstrate coupled to a piezoelectric transducer via a coupling medium.

The surface acoustic waves were generated on the piezoelectric $LiNbO_3$ wafer by an interdigitated transducer (IDT) and propagated as Rayleigh waves, in a non dispersive manner with a single velocity. The resonant frequency, $f_0$, is directly related to the Rayleigh wave velocity in the material, $c_R$, (3996 m/s), the SAW wavelength λ and the pitch of the interdigitated electrodes, D, as per equation (1):

$$\lambda = \frac{c_R}{f_0} = 2D \tag{1}$$

The Rayleigh waves were coupled into a substrate in the form of a sheet, or plate (which substrate sheet or plate may be referred to as a chip), via an intermediate thin film of water. As a free plate, the substrate supports a number of propagation modes, termed Lamb waves (named after Lamb, the first to carry out the analysis). There are two distinct classes of Lamb wave propagation modes, symmetric and antisymmetric, that can be resolved using the Rayleigh-Lamb frequency equations (2) and (3).

$$\frac{\tan\left(\frac{qd}{2}\right)}{\tan\left(\frac{pd}{2}\right)} = -\frac{4k^2pq}{(q^2-k^2)^2}, \text{ symmetric modes} \quad (2)$$

$$\frac{\tan\left(\frac{qd}{2}\right)}{\tan\left(\frac{qd}{2}\right)} = -\frac{(q^2-k^2)^2}{4k^2pq}, \text{ antisymmetric modes} \quad (3)$$

where $$p^2 = \left(\frac{\varpi}{c_L}\right)^2 - k^2,$$

$$q^2 = \left(\frac{\varpi}{c_T}\right)^2 - k^2,$$

and $$k = 2\pi/\lambda = \varpi/c_{phase}$$

with d the plate thickness, and $c_L$ (8433 m/s) and $c_T$ (4563 m/s) the longitudinal and transversal velocities, respectively.

These transcendental equations, with many real solutions, reveal that Lamb waves are dispersive, as the phase velocity, $c_{phase}$, is a function of the frequency thickness product fxd. Thus for a fixed frequency, the wavelength and the mode propagated in the substrate sheet can be controlled via its thickness.

Figure 12:
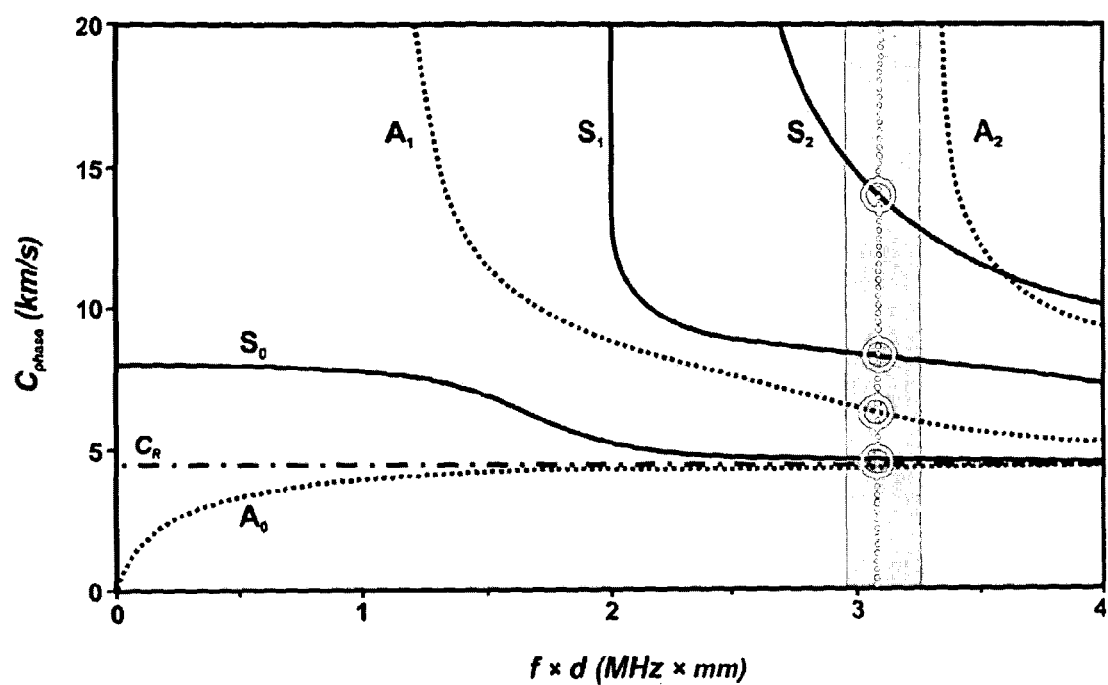
FIG. 12 shows the dispersion curve for a free plate, with phase velocity as a function of excitation frequency.

FIG. 12 shows the dispersion curve for a free plate, with phase velocity as a function of excitation frequency. At 12.6 MHz, two asymmetric and three symmetric modes can be excited. The phase velocities of the lowest order modes $A_0$ and $S_0$ are the closest to that of the propagating Rayleigh wave in the substrate sheet ($C_{phase}$, 3996 m/s), which the inventors worked with, and thus these modes are excited in preference to higher order ones. The inventors used these data, together with previously published criteria for phononic plate structures [Djafari-Rouhani B et al. (2008) Absolute band gaps and waveguiding in free standing and supported phononic crystal slabs. Photonics and Nanostructures—Fundamentals and Applications 6:32-37] to design phononic structures to manipulate fluid.

These phononic structures were then modelled as simple 2-D diffraction problems, where the acoustic waves were described using a time harmonic Helmholtz wave equation (4), in which a pressure wave, P, was launched into the structure (density ρ), over a range of wavelengths calculated from the Lamb wave number, k, at a particular (fd) product.

$$-\nabla\cdot\left(\frac{1}{\rho}\nabla P\right) - \frac{k^2P}{\rho} = 0 \quad (4)$$

The inventors developed simple phononic structures, where the lattice comprises an array of holes, and where all cases were treated with Neumann boundary conditions. Using these design criteria the inventors produced a series of square lattice 2D phononic crystals, which amplified or shaped the acoustic field, within the substrate sheet. The phononic crystal was used to create acoustic cavities, which were excited at different wavelengths, resulting either in scattering or reflection of the energy. This can focus the energy into specific regions of the chip. As a consequence, the interaction between the Lamb wave and the phononic lattice generates spatial variations of the acoustic field intensity, associated with the different propagation regimes within the chip.

Importantly, energy losses that occur during the coupling of the acoustic wave from the lithium niobate wafer into the substrate sheet are mitigated against by the phononic structure, which can focus the power into specific regions of the chip.

The Lamb waves propagated in the chip interact with the droplet of liquid placed on its surface in a similar fashion as Rayleigh waves in a piezoelectric material would. In the case of Rayleigh waves, the interaction with the liquid dampens the surface-propagating wave, which decays as it propagates along the surface. It is then termed a leaky Rayleigh wave and radiates a compressional wave into the liquid, which cannot support shear waves. Similarly, a droplet of liquid placed on the substrate renders the Lamb waves evanescent, with the acoustic energy being refracted into the liquid at an angle termed the Ralyeigh angle $\theta_R$, determined by Snell's law (equation 5) relating the speed of the waves in solid and liquid:

$$\sin\theta_R = \frac{c_{liquid}}{c_{solid}} \quad (5)$$

Depending on the power applied, different fluidic regimes can be induced in the droplet, from (acoustic) streaming where volumetric flow is created throughout the drop by recirculation, to the destabilisation of the contact line resulting in droplet movement, as well as nebulisation and jetting by disrupting the drop's free surface into smaller droplets. Examples of the spatial control of the acoustic energy upon the different regimes on the phononic superstrates are described in more detail below.

The SAW device was fabricated on a 128° Y-cut X-propagating 3 inch $LiNbO_3$ wafer, each device consisted of 20 pairs of electrodes to form an inter-digitated transducer (IDT) with pitch of 160 μm, 80 μm width, and a 10 mm aperture. The SAW IDTs were patterned using a lift off process where, after pattern transfer into an S1818 resist, a 20 nm titanium adhesion layer was evaporated prior to deposition of 100 nm of gold. Lift-off was then performed in acetone, in order to realise the pattern.

An Agilent Technologies MXG Analog Signal Generator N5181A was used in conjunction with a Mini Circuits ZHL-5W-1, 5-500 MHz amplifier and a 3A, ±24V DC power supply to power the SAW device. For nebulisation experiments, the driving signal for the SAW device was pulsed for 20 ms every 100 ms, to avoid heating. Droplets were imaged at 62 fps using a Red Lake M3 high-speed camera mounted on a Leica upright microscope, which allowed the capture of nebulisation from the droplets to be visualized, when the surface acoustic waves travelled through the droplet. The IDTs were characterised using an Agilent Technologies E5071C ENA series network analyser.

The superstrate was fabricated using silicon wafer with an approximate thickness of 470 micrometer. The 4 inch Si wafer was coated in AZ4562 photoresist and patterned using standard photolithography. The pattern comprised a square array (pitch 203 micrometer) of circular holes (radius 82 micrometer) and was transferred into resist layer. The photoresist pattern was then transferred into the silicon using dry etch (STS ICP) where the holes were etched. The wafer was cleaned in acetone and cleaved to provide the superstrates. The dimension of the patterned superstrate was approximately 20 mm by 30 mm. In the case of the acoustic horn, the aperture for the cone was made to be 10 mm to coincide with the IDT aperture and the apex of the cone was approximately 1.22 mm wide. (In the case of the centrifugal filter, described further below, the same square array of circular holes was used and actuation of the fluid was observed with 10 micrometer polystyrene beads (Duke Scientific G1000).) A 5 microliter volume of de-ionised water was placed between the substrate and the transducer surface to provide a coupling layer approximately 50 micrometer thick to promote SAW coupling.

Figure 13:
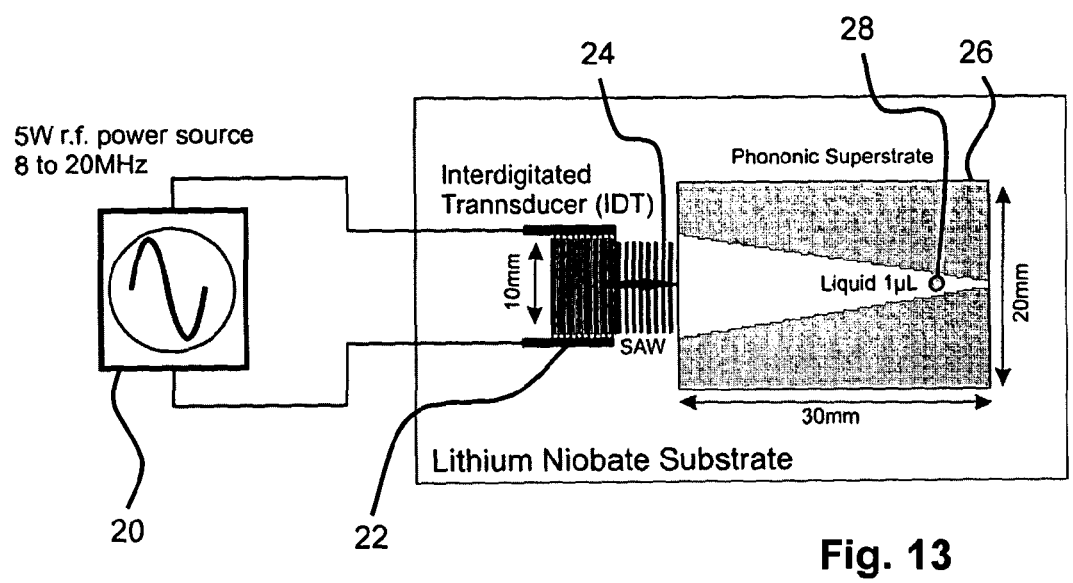
FIG. 13 shows a schematic view of a fluidics apparatus. A separable phononic superstrate in the form of a phononic cone is shown coupled to a lithium niobate substrate which comprises an IDT. The power source is 5 W (8 to 20 MHz).

A schematic of the device is shown in FIG. 13, which depicts the application of sinusoidal wave from a 5 W rf power source 20 (operable in the range 8 to 20 MHz) to the interdigitated transducer (IDT) 22 having an aperture of 10 mm to generate a Rayleigh Wave (SAW) 24. The SAW on the $LiNbO_3$ wafer surface induces Lamb waves in the superstrate 26 coupled to the $LiNbO_3$ wafer surface, where the intensity was focused at the 1 μl drop 28. The IDT electrodes had a pitch of 160 micrometer, electrode widths of 80 micrometer and an aperture of approximately 10 mm. The phononic crystal comprised holes of 82 micrometer radius with a pitch of 203 micrometer, to provide a fill factor of 0.8, etched into [100] silicon (where structure was aligned to the [011] direction of the silicon wafer, the propagation direction of the Lamb waves was parallel to the [011] direction).

The phononic superstrate was designed in the form of a phononic cone in order to focus the acoustic energy, as a series of steps (or cavities), with each feature being resonant at a particular frequency, and acting as a Fabry Perot cavity [Qiu C, Liu Z, Mei J, Shi J (2005) Mode-selecting acoustic filter by using resonant tunneling of two-dimensional double phononic crystals. Appl. Phys. Lett. 87:104101-104103; Wu T T, Hsu C H, Sun J H (2006) Design of a highly magnified directional acoustic source based on the resonant cavity of two-dimensional phononic crystals. Appl. Phys. Lett. 89:171912-171913].

Six steps, or cavities, of the phononic cone were identified. The inventors reviewed micrographic stills (not shown here) from a movie captured at 62 fps before and during nebulisation, with the device being excited at 12.6 MHz with an applied power of 1.25 W. Before nebulisation, with a droplet in the fourth cavity, the droplet was quiescent and its position could only be seen from light reflections. Next, the droplet in the fourth cavity is nebulised, whilst that in a different cavity was agitated, and thus became visible, but was not nebulised. The images referred to here are shown as FIGS. 17b, c and d in WO2011/023949.

Acoustic waves on the surface of the superstrate, within the phononic structure were observed using white light interferometry, and the wavelengths measured on both the $LiNbO_3$ wafer and on the superstrate within the phononic structure. The inventors chose an excitation frequency of the IDT, driving the SAW, in order to excite particular cavity modes within the phononic superstrate (i.e. cavities 1 to 6 referred to above). For example, the fourth cavity readily accommodated the contact area of the drop and was excited at 12.6 MHz.

Simulations were carried out of the phononic cone structure when excited at 12.6 MHz and 13.2 MHz respectively. Standing waves develop as a consequence of the sidewalls acting as a series of Fabry Perot etalons. The standing waves in the cavities are of up to an order of magnitude larger than the acoustic field on an unmodified superstrate (a superstrate with no phononic lattice), depending on the frequency. Each cavity could be excited at different frequencies, where there was about 300 KHz spacing between each cavity (i.e. between cavities 1 and 2; between cavities 2 and 3, etc). For example the second cavity showed the highest enhancement factor of about 10 at 13.2 MHz whereas the fourth cavity showed an enhancement of about 6 at 12.60 MHz excitation. The phononic cone was modelled as a simple 2-D diffraction problem using COMSOL Multiphysics v3.5a.

The simulations showed that different cavities of the device can be excited at different frequencies. The device has been designed so that the phononic structure acts as an efficient reflector and little energy is dissipated into the lattice. The simulations also show that the spatial variation in acoustic intensities, as well as the generation of standing waves, were perpendicular to the direction of propagation of the Lamb waves. Changes in frequency of 0.6 MHz can provide significant variations in acoustic field intensity, a fact corroborated experimentally.

Figure 14:
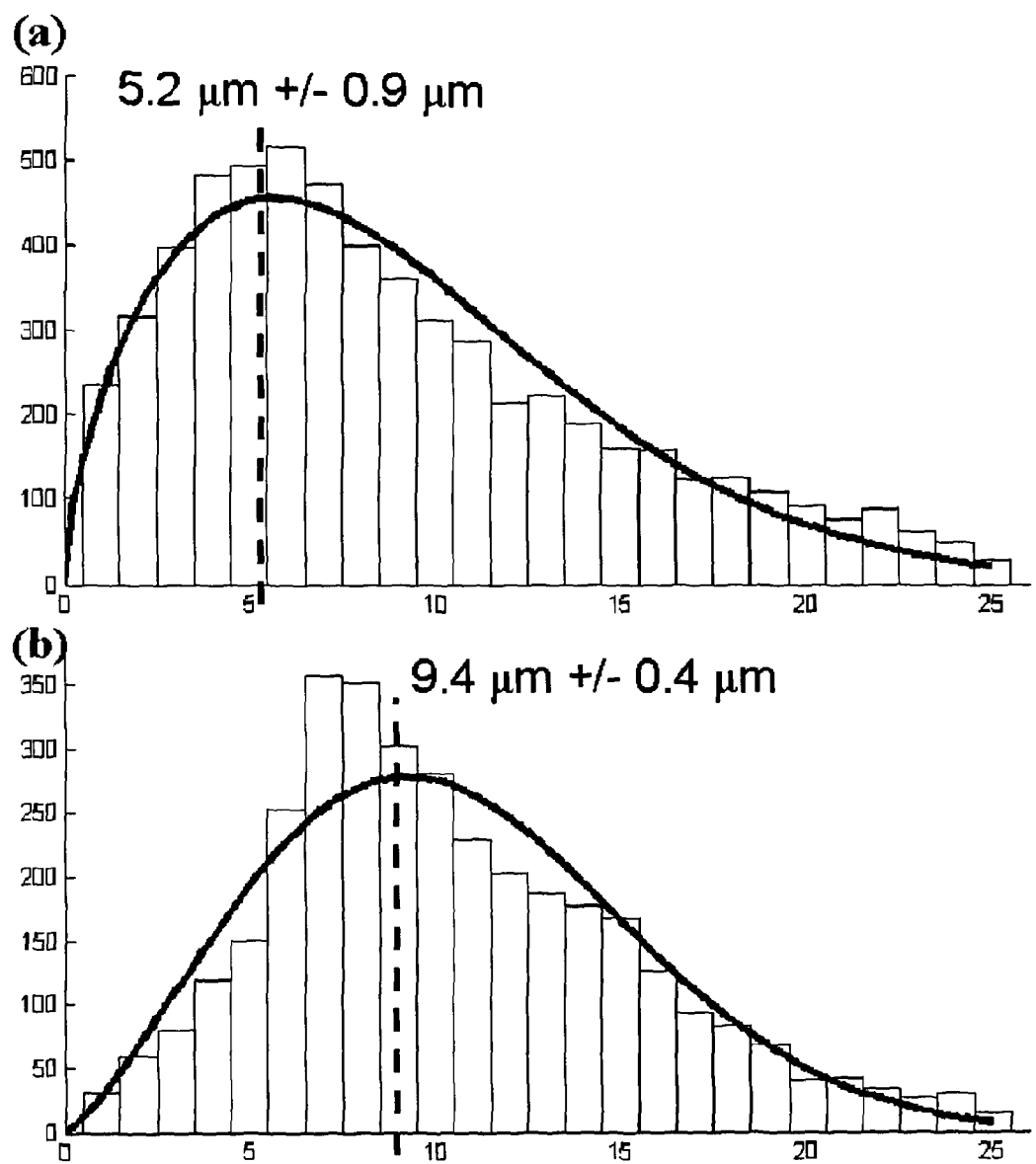
FIG. 14 shows the size of droplets ejected during nebulisation performed (a) on a phononic substrate coupled to a piezoelectric transducer arrangement, and (b) directly on the surface of the piezoelectric transducer arrangement.

The nebulisation phenomenon has been studied further. When relatively high powers are applied, the acoustic energy overcomes the surface tension pinning the drop to the surface so that it spreads out in a liquid film and gives rise to capillary resonance waves in the liquid which are determined by internal viscous damping and inertial forcing of the drop. These capillary waves have a wavelength on the order of the diameter of the nebulised drops with volumes in the sub-picoliter range. The nebulisation of a 1 microliter droplet proceeding on the phononic superstrate has been monitored. The droplet was placed in a cavity of the cone phononic superstrate and nebulised using SAWs excited with a frequency of 12.6 MHz and a power of 4 W. FIG. 14 shows the size of droplets ejected during nebulisation. Nebulisation of water droplets (1-2 microliters) was performed on the cone phononic superstrate coupled to the piezoelectric transducer arrangement (FIG. 14a) or directly on the surface of the piezoelectric transducer arrangement (FIG. 14b) with excitation frequencies around 12 MHz (+/−1.2 MHz). The size of the droplets ejected was measured with a Phase Doppler Particle Analyser. The data set from each experimental run (with multiple runs per condition) was fitted with a Weibull distribution and the modes extracted using Matlab (R2010a, The Mathworks, Inc.). An example of the fitted distribution, superimposed on the histogram, is shown for one run for each condition. Values presented are the average of the modes obtained for each condition with the standard deviation. Interestingly this data also shows that droplets nebulised on a phononic superstrate are smaller than on the IDT. However, the droplet size distribution was sharper when the nebulisation was carried out directly from the piezoelectric layer surface. Two other modes not associated with nebulisation were observed, with droplets sizes centered around 50 μm and 150 μm, resulting from jetting phenomena. The diameter of the droplets nebulised from the surface of the phononic cone superstrate was measured at 5.2 micrometer (+/−0.9 micrometer), and was not significantly different from a nebulisation happening on an unstructured superstrate.

However, a major difference with using an unstructured superstrate lies in the large variation in the extent of nebulisation on the phononic superstrate, which is dependent upon where the droplet was placed within the cone. This precise spatial control of the acoustic field has also been seen experimentally. Excitation of the droplet in the fourth cavity at 12.6 MHz resulted in nebulisation, whilst there is no excitation 10 mm away, in cavities within the trumpet of the cone. The spatial control of the acoustic energy also enabled the reproducible placement of the drop on the phononic superstrate as it aligned itself to the excited cavity when deposited around it, as described further below.

Droplet movement and splitting was also observed, as described below.

When the acoustic radiation applied or coupled in the superstrate overcomes or is equal to the sliding force $F_s$ given by equation (6), droplet movement can be achieved.

$$F_s = 2R\gamma_{LG}\sin\left(\frac{\theta_a + \theta_r}{2}\right)(\cos\theta_r - \cos\theta_a) \quad (6)$$

In equation (6) R is the radius of the drop, γ is the surface tension and $\theta_a$ and $\theta_r$ are the advancing and receding contact angles of the drop when no acoustic wave is applied.

Figure 15:
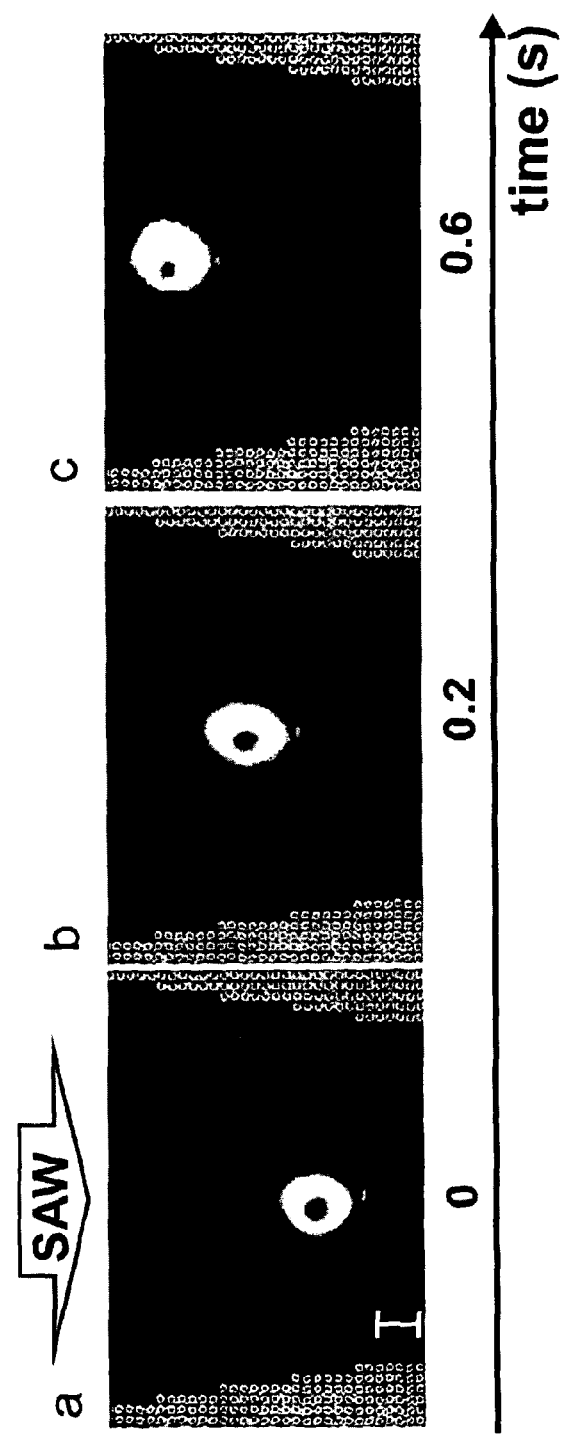
FIGS. 15(*a*), (*b*) and (*c*) show sequential microscopic images of movement of a droplet between cavities of a phononic cone.

By placing a droplet between two cavities, one of which is resonant, the spatial variation of the acoustic energy densities, results in acoustic forces on the droplet which splits and/or moves of the droplet as it moves towards the cavity with the higher energy. By tuning the strength and frequency of the field in the cavities, relative to each other, droplets will either divide symmetrically or asymmetrically. The process of droplet movement or division is driven by refracted waves (one directed) and reflected waves in the opposite direction (back from the phononic cone). The mobility of the drop can be improved by reducing the contact angle hysteresis, by making the surface hydrophobic. For example, a 5 microliter water droplet was observed to move back and forth between 3 cavities of a phononic cone treated with a hydrophobic silane. FIG. 15 shows the movement of a 5 microliter water droplet between three cavities of a phononic cone, at different times (a. 0 seconds; b. 0.2 seconds; c. 0.6 seconds), when the exiting frequency is changed from 12.23 MHz (a) to 12.43 MHz (c) with increments of 0.1 MHz The propagation of the SAW directly on the piezoelectric wafer or an unstructured superstrate coupled to the piezoelectric wafer resulted in droplet movements in the same direction as the SAW, whereas on the phononic superstrate, the droplet was moved in the opposite direction to the SAW, by increasing the frequency from 12.23 MHz to 12.43 MHz (−3 dBm). It was brought back to the same position by decreasing the frequency from 12.43 MHz to 12.23 MHz.

Sample Manipulation—"Centrifugation"

The same transducer arrangement as described above, used for droplet nebulisation, splitting or movement, can be used to create an on-chip "centrifuge" (more correctly "separator", as discussed above, but others in the art use the term "centrifuge"), by using a different superstrate, coupled to the transducer arrangement, as described below. It is further considered that an on-chip "centrifuge" can be created on the sample manipulation surface of the apparatus of the present invention, when taking into account the differences identified between the use of a separable phononic superstrate and the use of the surface of the SAW generating material layer as the sample manipulation surface. In the discussion below, the disclosure concentrates mainly on the use of a separable superstrate, but the disclosure is correspondingly applicable to the preferred embodiments of the present invention.

The device used for centrifugation of particles within fluid droplets is shown schematically in FIG. 20a of WO2011/023949. The transducer arrangement and superstrate were made as described above, except the phononic lattice was formed as a square, rather than as a cone.

Simulation (Comsol multiphysics 3.5a) investigated where a pressure wave was propagated in the superstrate at 12.6 MHz and has its symmetry broken by the phononic lattice. These results show that the phononic structure generates a difference in speeds of the induced Lamb wave in the superstrate, breaking the symmetry of the acoustic wave and inducing angular momentum within the sample. The resulting flow patterns concentrate particles within the liquid, due to fluid motions which have similarities to those described by Batchelor [Batchelor G K (1951) Note on a class of solutions of the Navier-Stokes equations representing steady rotationally-symmetric flow. Q. J. Mech. Appl. Math. 4:29-41; Raghaven R V, Friend J R, Yeo L Y (2010) Particle concentration via acoustically driven microcentrifugation: microPIV flow visualization and numerical modelling studies. Microfluid. Nanofluid. 8:73-84].

Figure 16:
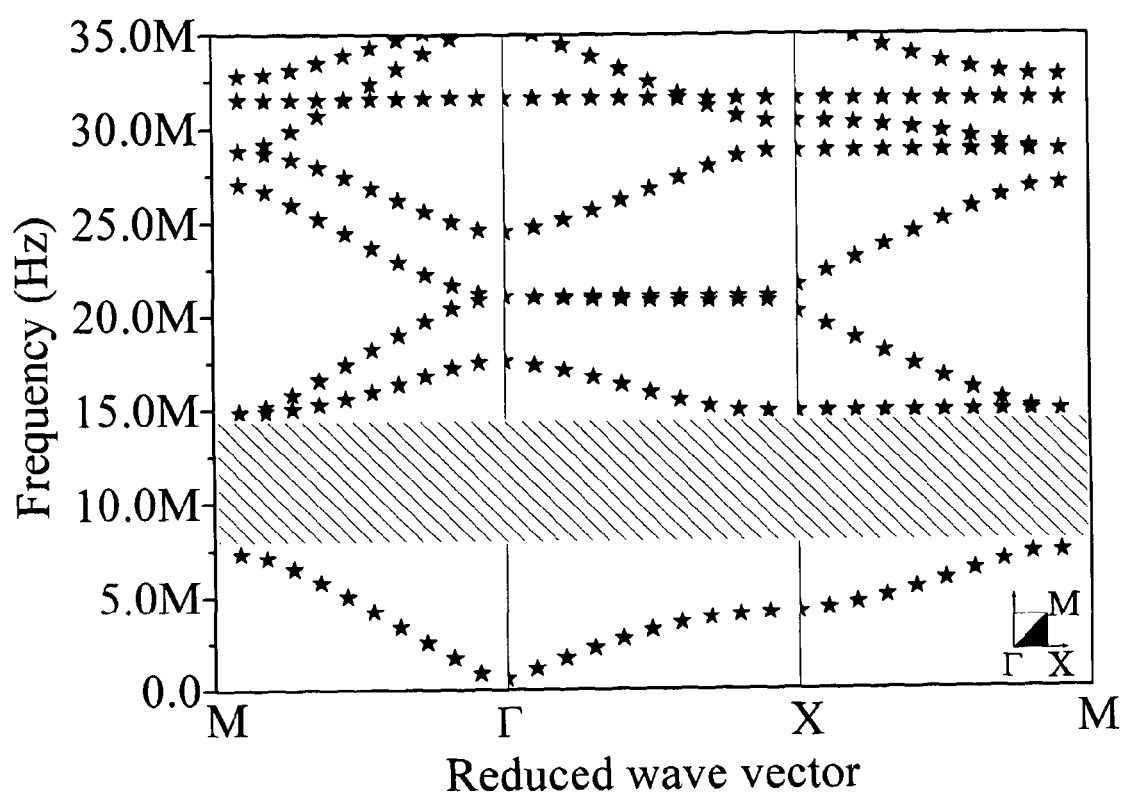
FIG. 16 shows the band structure of a phononic lattice for use with embodiments of the invention. The forbidden band is in the frequency range 7.5 MHz to about 15 MHz.

FIG. 16 shows the band gap of the square phononic array. The wave propagation was investigated using the two-dimensional plane wave expansion method [Hsu J and Wu T, (2006) Efficient formulation for band-structure calculations of two-dimensional phononic-crystal plates. Phys Rev. B, 74, 144303]. As will be understood by the skilled person, this type of reduced wave vector diagram is a convenient way to describe band gaps in symmetrical structures. Thus, in this example, where a phononic crystal has a particular symmetry, it is not necessary to consider all the possible propagation directions of a wave in the crystal. But by taking the symmetry of the structure into account it is only necessary to consider propagation in a reduced number of directions; for a square lattice (as in this example) we only need to take directions from 0 to pi/4 radians (0 to 45 degrees) with respect to one of the reciprocal lattice vectors of the crystal. The reciprocal lattice is the Fourier map of the crystal (or its diffraction pattern), where the wave vector of a wave is the direction of propagation with respect to the reciprocal lattice. For isotropic materials, it is only necessary to consider one direction of propagation, or one wave vector. The forbidden area corresponds to the absolute band gap from 7.67 MHz to 14.48 MHz. These data complement the simulation, which showed the wave filtered by the phononic structure when propagated at 12.6 MHz.

In order to better understand the flow patterns generated by this type of phononic structure, the inventors explored the behaviour of beads within these flows. The results are shown in FIGS. 20c and 20d of WO2011/023949 and the associated text of that document describing those drawings.

Figure 22:
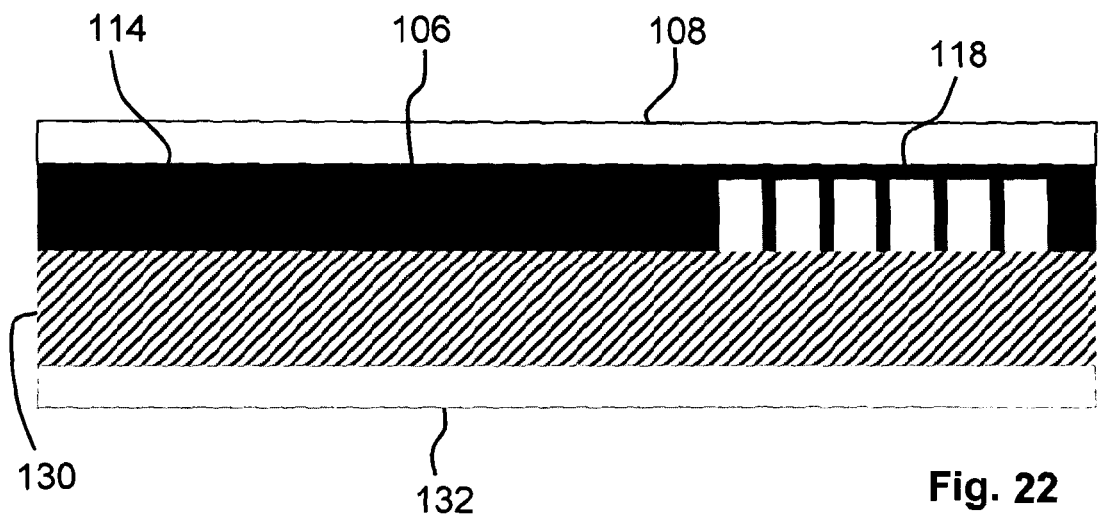

As a relevant example of a biological application, the concentration of blood cells from diluted blood samples was demonstrated, as shown in FIG. 22 of WO2011/023949 and is associated description in WO2011/023949.

The inventors have demonstrated a new concept in microfluidics showing that complex microfluidic manipulations, including for example the centrifugation of blood, can be performed on a disposable phononic chip. The SAW excitation frequency was chosen to couple across the transducer-superstrate interface, where droplet manipulation was achieved. The phononic structures interact with the acoustic field, providing excellent reflectivity or scattering to the incoming acoustic waves. The experiments described herein show how droplet actuation is dependent upon the geometric design and elastic contrast within the phononic crystal, as well as the frequency of the acoustic wave, and how a variety of different fluid motions on a disposable chip can be produced on-chip, including droplet movement, splitting, nebulisation and centrifugation (without the need for electrodes, channels or pumps, for example). This flexible and powerful method does not require complex interconnect technologies, nor high voltages (as is the case in many electrokinetic techniques). In the future, by combing different phononic structures, it will become possible to create a "tool-box" of different fluidic functions (each being modulated by the geometric structure and the frequency of the acoustic wave). Just as in electronics, where different components are combined to create a circuit, so, combinations of phononic lattices will produce complex microanalytical systems, on chip. It is acknowledged that the transducer arrangement described here (i.e. a single crystal LiNbO$_3$ piezoelectric wafer) is relatively expensive. One way to mitigate this is to use a low cost disposable superstrate for coupling with the transducer arrangement. However, a more preferred approach is to manufacture a disposable piezoelectric transducer, with the sample manipulation surface formed in the piezoelectric layer, the manufacture of the transducer being much cheaper due to the avoidance of the use of a single crystal piezoelectric material.

In conclusion of this section relating to phononic structures, the phononic structures can be highly frequency and/or wavelength selective. The phononic structures do interact with the acoustic field if working in the correct operating regime providing good reflectivity to the incoming acoustic waves. It has been shown that such structures can be used to engineer the acoustic field to provide enhanced manipulation (such as atomisation) of liquid droplets from the substrate surface. Manipulation processes applied to the fluid sample can be one or more of:

movement
mixing (e.g. within a single fluid sample)
splitting of the fluid sample
combining two or more fluid samples
sorting fluid samples or particles (or cells) within fluid samples atomization
concentration, including centrifugation In addition, embodiments of the present invention allow sensing of fluid samples (e.g. sensing the location of one or more fluid samples) by considering attenuation of mechanical waves picked up by one or more transducers at the piezoelectric layer.

Transducer Electrode Structure

As stated above, in some preferred embodiments of the present invention the transducer includes a slanted interdigitated arrangement of electrodes, known as a slanted IDT or slanted finger IDT.

Slanted finger IDTs are used in data terminals as mid-band and wide-band filters. The theory of using slanted electrodes in microfluidics has been described Mu, T. & Chang, I., 2005. Actuating and detecting of microdroplet using slanted finger interdigital transducers. Journal of Applied Physics, 98(2), 024903-71. However, practical realization of such devices has not been demonstrated, either with droplets directly on piezoelectric or on separate (e.g. disposable) superstrate. The inventors investigated the use of slanted IDTs in microfluidics, in particular the use of a slanted IDT in combination with a separable superstrate.

The SAW amplitude excited by a slanted IDT is not uniform and different profiles can be obtained by tuning the input frequency. The resonant frequency, f, is dependent upon the pitch of the fingers D, and the sound velocity on the piezoelectric wafer, c (Equation 1, above, reproduced in slightly different form as Equation 1* below). Consequently, for a given input frequency, the SAW output is only generated when the gap (D/2) between the IDT satisfies the ability of the electrodes to support the resonance.

$$2D = \lambda = \frac{c}{f} \qquad \text{Equation 1*}$$

The inventors fabricated divergent IDT electrodes where both the electrode separation (D/2) and their width (D/2) varied linearly from 62.5 micrometer to 125 micrometer along the aperture. This corresponds to wavelengths of 250 micrometer to 500 micrometer and a range of frequencies from 16 MHz to 8 MHz on 128 degree Y-cut X-propagating 3 inch LiNbO$_3$ wafer, where c=3990 m/s. Ten pairs of fingers of 15 mm in length were used. The IDTs were patterned using a lift-off process. After pattern transfer into an AZ4562 resist, a 20 nm titanium adhesion layer was evaporated prior to deposition of 100 nm of gold. Liftoff was then performed in acetone, realizing the IDT. The S-parameter was measured to characterize the IDT and showed a stable response for frequencies between 8 MHz and 14 MHz (FIG. 17b insert).

Figure 17:
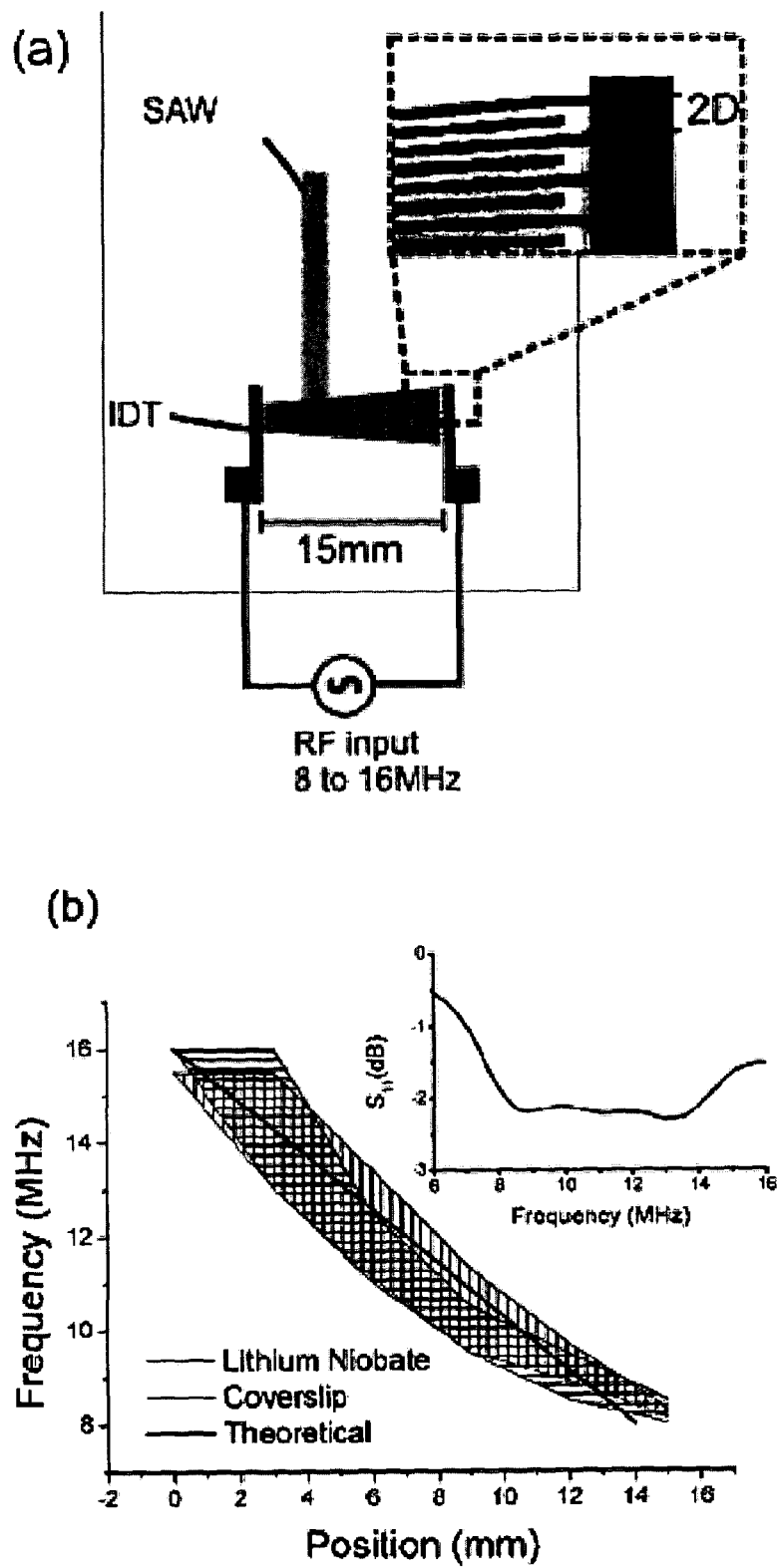
FIG. 17 shows (a) a schematic representation of a device including a slanted IDT, for which the lateral position of the SAW emission train is dependent upon the input frequency; and (b) a graph showing the relationship between input frequency and SAW position as calculated theoretically (line) and as determined experimentally on a lithium niobate transducer (horizontally hatched area) and on a separable substrate coverslip (vertically hatched area). The inset in FIG. 23(*b*) shows the magnitude of the $S_{11}$ parameter.

FIG. 17a shows a schematic representation of the slanted IDT with the propagation of the SAW on a lithium niobate wafer for a selected input frequency of 13 MHz. Only that part of the IDT that supports the resonance condition is excited, resulting in the propagation of a SAW with a smaller aperture, when compared with a parallel electrode IDT. Thus, by tuning the frequency, it was possible to control the lateral position of the excitation wave, as shown theoretically and experimentally in FIG. 17b.

FIG. 17b shows the experimental input frequency needed to actuate a droplet on the surface of the LiNbO$_3$ wafer, as well as on a coverslip coupled to the LiNbO$_3$ wafer, as a function of the position, and the theoretical calculation of the centre of the SAW pathway. Results for the lithium niobate wafer are shown using horizontal hatching and results for the coverslip are shown using vertical hatching. The theoretical response is shown using a line. The inset in FIG. 17b shows the magnitude of the S-parameter obtained with an Agilent Technologies E5071C ENA series network analyzer. An Agilent Technologies MXG Analog Signal Generator N5181A was used in conjunction with a Mini Circuits ZHL-5W-1, 5-500 MHz amplifier and a 3A, 24V DC power supply to power the SAW device. The wafer was fixed with thermal paste on a heat sink to avoid overheating. The aperture was characterized for each input frequency at a power of −12 dBm, by observing the agitation of an array of 1 microliter droplets arranged in front of the IDT. The inventors then showed that the same spatial control of the SAW, using the excitation frequency, can be extended to applications involving the use of a separable superstrate coupled to the LiNbO$_3$ wafer. In this case, an unmodified glass coverslip was used as the separable superstrate, and the position of the SAW on the cover slip at given frequencies was directly compared with the SAW position on the native lithium niobate wafer (FIG. 23b). It was found that the lateral width of the SAW beam at a given frequency on the substrate (coverslip) was larger (16% on average) than that directly on the piezoelectric wafer, due to diffraction of the wave in the process of the coupling.

Figure 24:
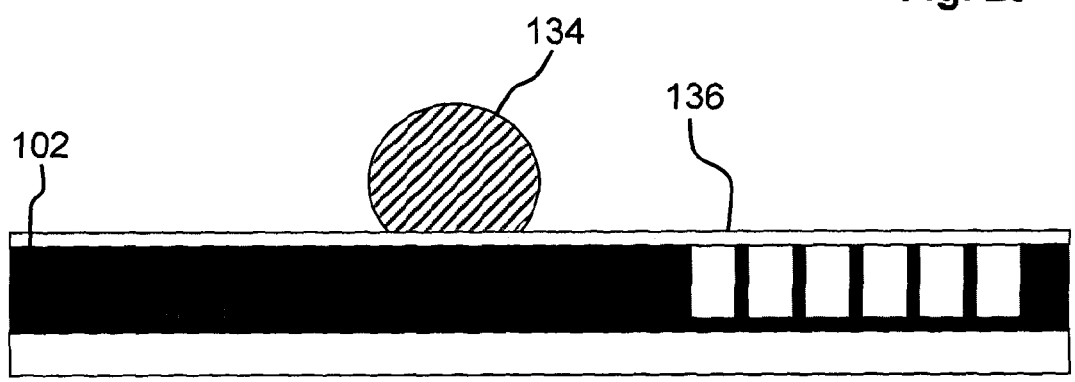

The movable lateral position of the SAW beam using the slanted IDT was then used to actuate a microfluidic droplet. The inventors demonstrated that a tunable IDT can provide SAWs to a droplet to induce rotational streaming in the droplet, and thereby centrifuge particles in the droplet to concentrate them in the centre of the droplet. The results are shown in FIG. 24 of WO2011/023949 and the associated description in WO2011/023949.

Figure 25:
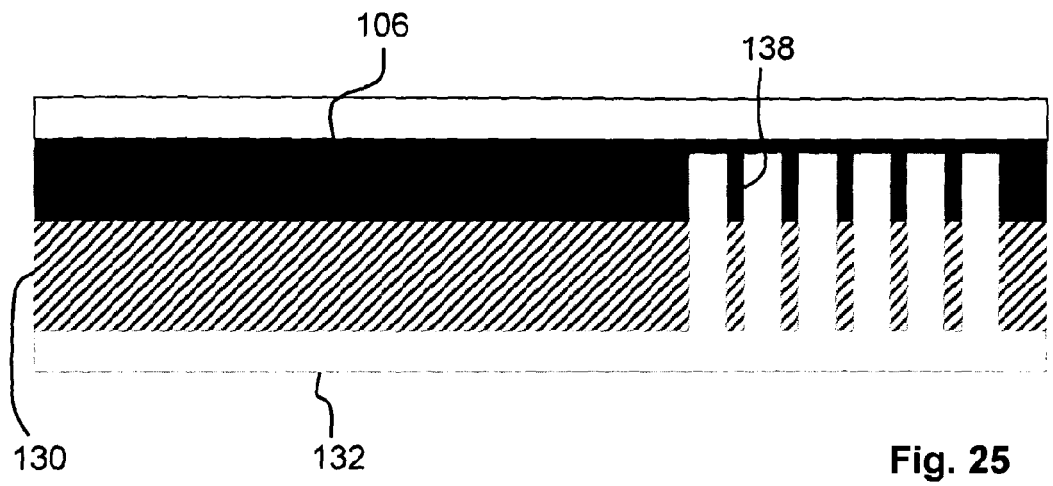

Far from being limited to particle concentration, slanted IDTs give the opportunity to programme multiple functions with a single electrode. The inventors demonstrated that it is possible to move, merge, mix and centrifuge a droplet on a glass superstrate by tuning the frequency of the input signal. The results are shown in FIG. 25 of WO2011/023949 and the associated description of WO2011/023949.

It is possible to integrate the on-chip formation of colloids with both surface enhanced Raman scattering (SERS) and surface enhanced resonance Raman scattering (SERRS) for sensitive bioanalyte detection. The inventors have shown that a slanted IDT, in which the lateral position of the SAW emission train is dependent upon the input frequency, can be used to design complex fluidic functions directly into a chip. The inventors have demonstrated the potential of this powerful tool to manipulate droplets and particles within droplets. In contrast to known techniques, a clear advantage of this flexible method lies in the ability to induce streaming in a droplet in a chosen direction and at any position. Whilst known techniques are also restricted to varying the input power to control the concentration of particles, the inventors have demonstrated that it is possible to control the concentration of particles in a droplet by shifting the position of the SAW (i.e. moving the lateral position of the SAW emission train), and hence its region of interaction with the droplet. The inventors also demonstrated that complex tasks can be programmed sequentially into a single IDT device, by demonstration that two droplets cab be moved, merged, mixed and centrifuged on a superstrate (in this case a disposable glass superstrate). This latter example shows the flexibility of the platform for basic fluidic operations needed in lab-on-a-chip technologies.

In the field of SAW microfluidics it has been reported that the SAW Rayleigh wave, which normally propagates in the piezoelectric wafer, can be coupled into a disposable superstrate as a Lamb wave, providing a clear route by which 'lab-on-chip' technology can be applied to low cost, point of care diagnostics. In this known configuration, the surface acoustic excitation in the piezoelectric wafer is usually coupled into the superstrate through a thin liquid film interface. The inventors have now demonstrated a new concept in SAW microfluidics, which combines the use of a separable superstrate that is coupled to a transducer arrangement that includes, for example, a slanted finger IDT. In the devices described above, a disposable glass coverslip was used as the separable superstrate. The inventors have provided a powerful method by which it is possible to handle droplets and particles in a programmable fashion, and have demonstrated, for example, droplet movement, merging and centrifugation, on the same superstrate, with only the need to change the SAW excitation frequency to achieve a high degree of functional integration.

Sample Manipulation—Cell Lysis

The present inventors have demonstrated the use of surface acoustic waves (SAW) to lyse cells and blood in microliter-sized droplets. Sample preparation is a key component of "lab-on-chip" systems (LOC). More particularly, cell lysis and blood handling are usually required for a wide range of biological assays in diagnostic applications. Recently, chemical-free mechanical methodologies overcame the limitations of translating traditional procedures, involving lytic agents and subsequent washes, on microfluidic platforms, that arose from the detrimental effects of the chemicals on the molecules to be analysed. However, these new techniques often require external pressure-driven systems that constrain their integration into standalone LOC systems, or the use of high energies (heat, electricity or ultrasonication) that may compromise the molecules. The present invention makes use of the acoustic pressure-fields and liquid streaming induced in a droplet by SAW. Methods according to the present invention carried out on biological samples resulted in the lysis of above 99.8% of all cells in the samples. The availability of intracellular material in the resulting suspension was studied with optical absorbance measurements and was comparable to a lab-based chemical procedure. The present inventors also demonstrated that the necessary conditions for lysis can be achieved using different SAW platforms, providing multiple routes to integrate sample preparation in a complete assay on a microchip.

The inventors' relevant work on cell lysis is shown in WO2011/023949, specifically in relation to FIGS. 26-30 of WO2011/023949 and the associated description of WO2011/023949.

PREFERRED EMBODIMENTS OF THE INVENTION

Various preferred embodiments of the invention require that the fluid sample to be manipulated in the apparatus should be contained within the apparatus. This is particularly to avoid potential contamination of the user. It is also preferred that the apparatus is robust. Furthermore, it is particularly preferred that the apparatus should be disposable (i.e. cost-effectively operable as a single use apparatus). In such an apparatus, it is important that features of the manipulation surface should be aligned correctly and reproducibly with respect to the SAWs and this with respect to the transducer electrode structure.

The configuration disclosed in PCT/GB2010/001600 (filed 24 Aug. 2010 by the same applicant as the present application and published as WO2011/023949) uses a superstrate, removably coupled to a transducer substrate. An assay can be run on the superstrate, the SAWs being transmitted to and propagate across the surface of the superstrate. The superstrate can be a single use superstrate. However, for demanding applications such as diagnostics, such an apparatus may face challenges. In particular, the coupling between the superstrate and the transducer substrate is crucial for transmitting the power. A less efficient coupling reduces the performance. A less reproducible coupling further reduces the performance of the device in terms of predictability of operation. The alignment of the phononic structures on the superstrate with the exciting SAW aperture propagating on the transducer substrate also has a significant influence on the performance of the phononic lattice. Capping the superstrate would involve further alignment issues.

In the preferred embodiments of the present invention, the phononic structures (in the form of the arrangement of the SAW scattering elements), the SAW actuator (usually an interdigitated transducer, IDT) and the fluidics (either as channels or droplets) are layered in a single apparatus. The form of such an apparatus allows the alignment of the sample manipulation surface and the transducer electrode structure to be controlled during the manufacture of the apparatus. Similarly, the coupling between the transducer and the manipulation surface can be made to be reliable and efficient. Furthermore, the apparatus structure lends itself well to being manufactured via a layered manufacture type process, which in turn helps to allow mass production of the apparatus. Suitable production techniques rely on deposition of the SAW generating material layer (e.g. the piezoelectric layer) by screenprinting, sputtering, casting, solution deposition, doctor blading, electrophoresis deposition, or laminating, for example. These processes can take place in a reel-to-reel format, for example. One or more layers of the apparatus can be formed of a relatively cheap material such as plastics or paper. Other layers may be formed by layer deposition (e.g. screenprinting, sputtering, casting, laminating, etc., as mentioned above).

FIG. 18 shows a schematic cross sectional view through a fluidics apparatus according to an embodiment of the invention. First piezoelectric layer 102 is formed on a substrate 104. Substrate 104 may be formed, for example of plastics (e.g. PET, PC, etc.), and serves to support the piezoelectric layer 102 during its formation and also serves to support the apparatus as a whole in use. In some embodiments, substrate 104 need not be present, e.g. where the apparatus is otherwise self-supporting. Second piezoelectric layer 106 is located on the underside of second substrate 108.

The piezoelectric layers may be formed as a composite material, e.g. with a layer of ZnO on a substrate of SU-8 or ceramics. The composite may be a dispersion of piezoelectric particles in a polymer matrix, described in more detail below. Alternatively, the piezoelectric layers are each formed as a bulk layer, e.g. from $LiNbO_3$.

The surfaces of the first and second piezoelectric layers are sample manipulation surfaces. These surfaces between then define a channel 110 for a fluid sample.

First transducer electrode structure 112 is embedded in the underside of the first piezoelectric layer 102. The transducer electrode structure is in the form of an interdigitated electrode, as described in more detail above. Similarly, second transducer electrode structure 114 is embedded in the upper side of the second piezoelectric layer 106.

A first arrangement of SAW scattering elements 116 is formed in the first piezoelectric layer 102, longitudinally offset from the first transducer electrode structure 112. Each SAW scattering element takes the form of a cavity formed in the piezoelectric layer. The SAW scattering elements can be formed by etching or embossing, for example. In alternative embodiments, each SAW scattering element can instead be formed of a mechanically contrasting material, e.g. by filling a suitable cavity with a fill material. A suitable mechanically contrasting material may be a capillary media (e.g. liquid, gel, polymer, paper, etc.) or other material (metal, polymer, composite, etc.). A second arrangement of SAW scattering elements 118 is formed in a similar manner in the second piezoelectric layer 106. Each SAW scattering element intersects the sample manipulation surface.

FIG. 19 shows the view along second A-A' in FIG. 18, showing the regular lattice geometry of the arrangement of SAW scattering elements.

The transducer electrode structures 112, 114 can be fabricated by, for example, embossing/lithography, sputtering, electrodeposition, etc. The material of the electrode structures may be any suitable material such as gold, platinum, etc.

The structure of the apparatus shown in FIGS. 18 and 19 can be modified as shown in FIGS. 20 and 21. In FIG. 20 (upper drawing), a modified transducer electrode structure 120 can be used, in which the electrode is embedded in the underside of the second piezoelectric layer 106. In this way, the electrode is formed in the same surface as the sample manipulation surface.

In FIG. 20 (lower drawing), a further modified transducer electrode structure 122 can be used, in which the electrode is embedded in the second piezoelectric layer 106 so that it extends through the thickness of the second piezoelectric layer 106.

In FIG. 21 (upper drawing), the SAW scattering elements 124 are modified in comparison with the SAW scattering elements 116 in FIGS. 18 and 19. In FIG. 21 (upper drawing), the SAW scattering elements 124 extend through the thickness of the first piezoelectric layer 102.

In FIG. 21 (lower drawing), the SAW scattering elements 126 are also modified in comparison with the SAW scattering elements 116 in FIGS. 18 and 19. In FIG. 21 (lower drawing), the SAW scattering elements 126 extend only through about half of the thickness of the first piezoelectric layer 102.

The apparatus of FIG. 18 can be operated by applying the same signal (or different signals) to the first and second transducer electrode structures 112, 114 in order to generate SAWs at the sample manipulation surfaces. A fluid sample located in channel 110 is therefore subjected to the SAWs in the manner described above. The SAW scattering elements 116, 118 interact with the SAWs in order to affect their transmission or distribution, for example, and this in turn affects the fluid sample. The way in which the SAWs affect the fluid sample due to their interaction with the SAW scattering elements has been discussed in detail already, and is described further below in the context of the preferred embodiments.

FIGS. 22-25 show modifications of the structure of the apparatus of FIG. 18. Similar reference numerals are used for similar features, and they are not described again here.

In the apparatus shown in FIG. 22, channel 130 is formed between the sample manipulation surface and an encapsulation layer 132. The function of the encapsulation layer 132 is simply to enclose the channel 130, so that fluid can move along the channel by capillary action, or through the action of the SAW as a pump.

Figure 23:
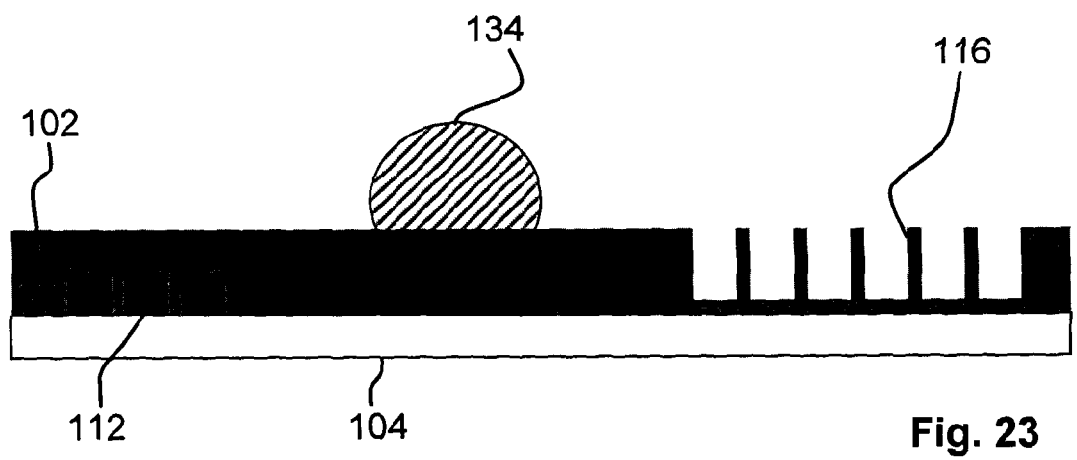

In the apparatus shown in FIG. 23, the sample manipulation surface is exposed. Droplet 134 is locatable on the sample manipulation surface, for interaction with the SAWs (as modified by the SAW scattering elements 116) as described above.

FIG. 24 shows a modification of the apparatus of FIG. 23, in which a passivation layer 136 is formed over the upper surface of the piezoelectric layer 102. The passivation layer allows the fluid of interest to be selected independently of any concerns about chemical interaction between the piezoelectric layer 102 and the fluid. The passivation layer essentially takes the role of the superstrate described above, but in this case the passivation layer is fixed in terms of position on the piezoelectric layer at the time of manufacture of the apparatus and is not removed in use and is not intended to be removed.

FIG. 25 shows a modification of the device of FIG. 22. In this modification, the SAW scattering elements 138 extend through the piezoelectric layer, across the channel and to the encapsulation layer 132. As will be apparent, similar modifications can be made to the apparatus shown in FIGS. 31-34, 36-37. The SAW scattering elements 138 here are formed of the same material as the encapsulation layer 132, but they could be formed of a different material. The SAW scattering elements therefore provide additional functionality, e.g. trapping or filtering (working as a membrane with a specific pore size), or may alter the hydrodynamic flow in a manner dependant upon their geometry. For example, beads of different sizes passing along the channel would be deflected in a size specific manner (Keith J. Morton et al. PNAS 2008 105 (21) 7434-7438; doi:10.1073/pnas.0712398105)).

The design of the transducer electrode structure may be selected in order to control the aperture of the acoustic waves. This is as discussed above, with reference to a slanted IDT (in which the finger spacing changes along the width of the transducer electrode structure) or a focussed IDT (in which the energy is focused in a particular point in the capillary channel—see below).

Other electrical transducers or electrodes can be introduced to be in communication with the sample manipulation surface to serve as additional manipulating means, such as to carry out dielectrophoresis, to perform lysis, and/or to detect particles or molecules or to quantify the flow. Additionally or alternatively, one or more sensors may be in communication with the sample manipulation surface. Suitable sensors include impedance sensors, electrochemical sensors, etc.

Figures 26, 27:
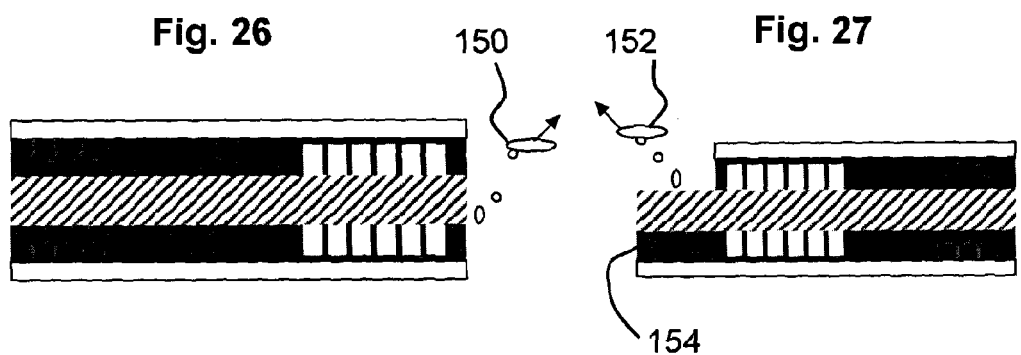
FIGS. 26-28 illustrate uses of the preferred embodiments of the invention (in different forms) for the preparation of nebulised samples for mass spectrometry.
Figure 28:
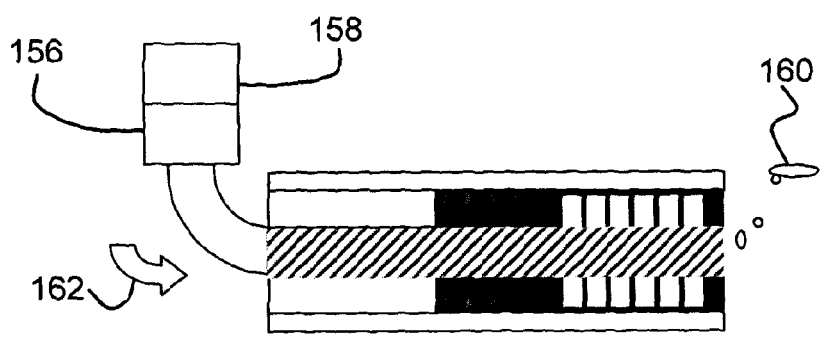

FIGS. 26-28 illustrate a use of the apparatus to carry out sample nebulisation. It is known to use SAW devices in order to prepare samples for analysis, e.g. for mass spectrometry. See, for example Heron et al (2010) [S. R. Heron et al "Surface Acoustic Wave Nebulization of Peptides As a Microfluidic Interface for Mass Spectrometry" Anal. Chem. 2010, 82, 3985-3989], the content of which is incorporated herein by reference in its entirety. The use of SAW devices to nebulise fluid samples for mass spectrometry has several advantages over the known approaches of matrix assisted laser desorption ionization (MALDI) and electrospray ionization (ESI).

In FIG. 26, the apparatus of FIG. 28 is used to carry out nebulisation. The apparatus is controlled so that the nebulised sample 150 is allowed to exit the apparatus from the end of the channel 110.

In FIG. 27, the apparatus of FIG. 18 is modified so as to provide an open section 154 of the apparatus, from which the nebulised sample 152 is allowed to exit the apparatus.

In both FIGS. 26 and 27, the nebulised sample is directed to a mass spectrometer (not shown), or other gas phase analytical device, for further analysis.

In FIG. 28, the apparatus of FIG. 18 is further modified in order to provide a reservoir to feed the nebulisation of the sample 156. The apparatus therefore operates as a pump. Sample 156 is held in reservoir 158. In the manner indicated in FIG. 26, the apparatus is operated to provide a nebulisation plume 160 from an exit of the apparatus. Further sample 156 is drawn along the flow channel in the apparatus in the direction shown by arrow 162, to replace the sample lost from the apparatus by nebulisation.

It will be understood that the apparatus shown in FIGS. 26-28 may also be used to provide evaporation of sample, in addition to or in place of nebulisation. In each of the apparatus, the channel 130 may be open, or may contain a capillary media such as paper.

The apparatus illustrated in FIGS. 18-28 have the advantage of cost effective fabrication and materials being available. As explained above, the phononic structures can be aligned with the transducer at the time of manufacture. Where an enclosed channel is provided, this can mitigate against contamination and/or evaporation. The phononics structures may be manufactured in order to additionally provide fluidic structures (e.g. as in FIG. 25). Additionally, and as explained further below, it is possible to locate reagents in the apparatus so that the reagents are pre-packaged in the apparatus.

FIGS. 29-37 illustrate further suitable configurations for apparatus according to embodiments of the invention. Similar features are given the same reference numerals in these drawings and description of similar features is not necessarily repeated.

Figure 29:
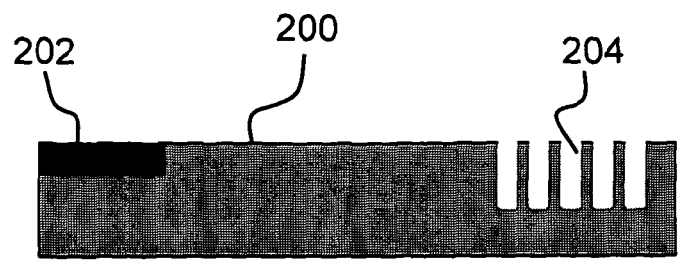
FIG. 29-37 illustrate further preferred embodiments of fluidics apparatus according to the present invention.

In FIG. 29, the piezoelectric layer 200 has the transducer electrode structure 202 formed embedded in the sample manipulation surface side of the piezoelectric layer. The SAW scattering elements, also formed in the sample manipulation surface side of the piezoelectric layer, are in the form of open cavities 204.

Figure 30:
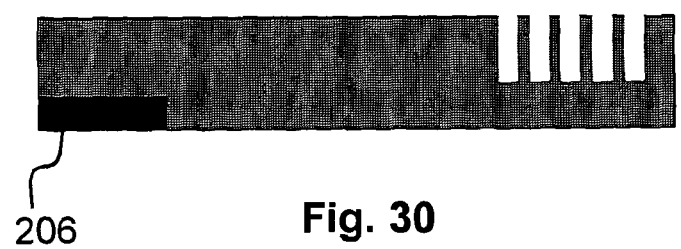

FIG. 30 is similar to FIG. 29 except that the transducer electrode structure 206 is formed embedded in the opposite side to the sample manipulation surface side of the piezoelectric layer 200.

Figure 31:
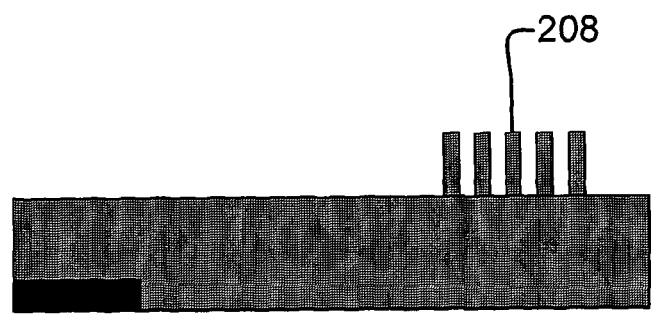

FIG. 31 is similar to FIG. 30 except that the SAW scattering elements, formed at the sample manipulation surface side of the piezoelectric layer, are in the form of upstanding columns or pillars 208. These may be formed of the same material as the piezoelectric layer.

Figure 32:
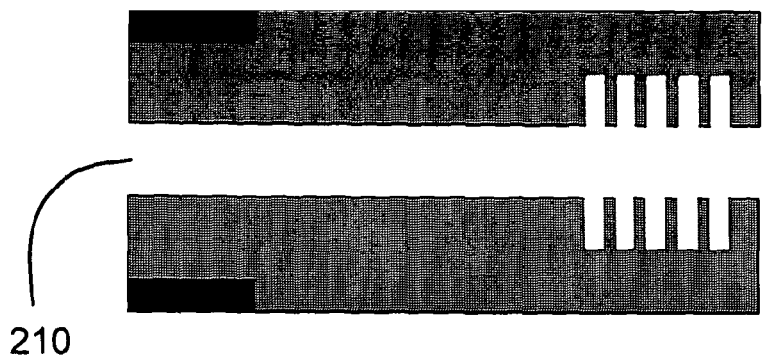

FIG. 32 corresponds to a structure formed by taking two apparatus according to FIG. 30 and inverting one to oppose the SAW scattering elements across channel 210. This apparatus is similar to that shown in FIG. 18.

Figure 33:
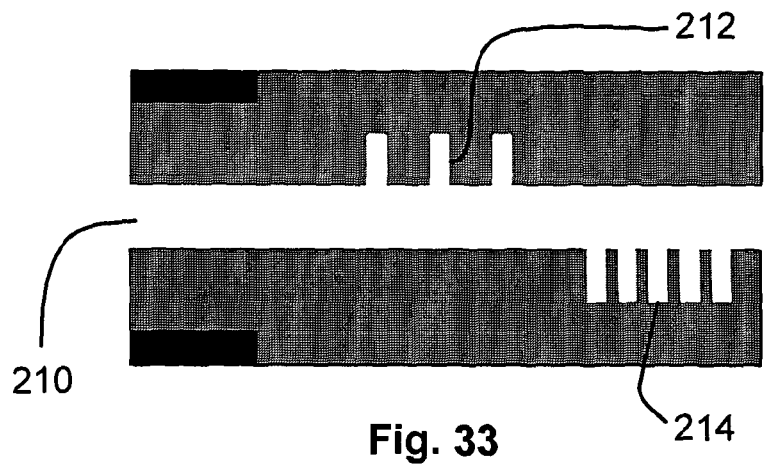

The apparatus shown in FIG. 33 differs from FIG. 32 in that the second piezoelectric layer has a different arrangement of SAW scattering elements 212. The SAW scattering elements in the second piezoelectric layer have a different periodicity to, and are offset from, the SAW scattering elements 214 in the first piezoelectric layer. The effect of this is to provide a more complex distribution of SAWs at the sample manipulation surfaces and corresponding control over the manipulation of the fluid sample in the channel 210. This structure has particular utility where the sample fluid is subject to phase separation such that one phase is in contact with the sample manipulation surface of the first piezoelectric layer and the other phase is in contact with the sample manipulation surface of the second piezoelectric layer. Since the two phases in general may have different mechanical properties, it is in general more convenient to use different arrangements of SAW scattering elements to control them.

Figure 34:
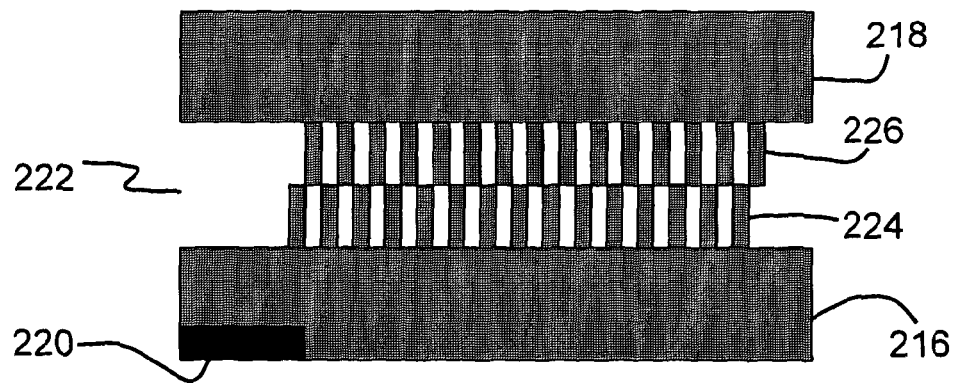

The apparatus shown in FIG. 34 has first 216 and second 218 piezoelectric layers. Both layers have associated transducer electrode structures, but in the drawing only first transducer electrode structure 220 is shown. Between the respective sample manipulation surfaces of the first and second piezoelectric layers is defined a sample flow channel 222. SAW scattering elements 224 and 226 are arranged to extend from the first and second piezoelectric layers, respectively. In FIG. 34, the SAW scattering elements 224 and 226 have similar periodicity but are offset from each other so that the two arrangements of SAW scattering elements are out of phase. In operation, the SAW scattering elements serve both to affect the propagation and distribution of SAWs at the sample manipulation surfaces and also to affect the flow of fluid along the channel. The SAW scattering elements provide a matrix of upstanding pillars. This can provide a separation function, for separating one component of the sample fluid from another component of the sample fluid. For example, the arrangement may allow separation of one phase from another in the fluid sample, the different phases being generated, for example, during operation of the apparatus.

Figure 35:
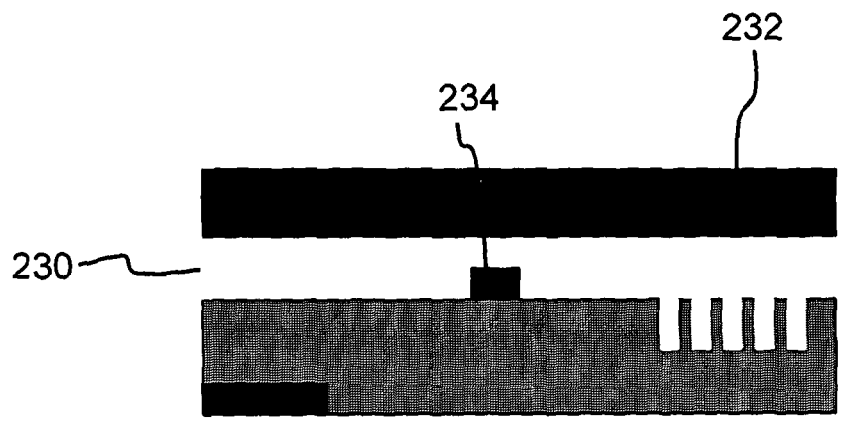

FIG. 35 illustrates a further embodiment in which channel 230 is defined between a sample manipulation surface of the piezoelectric layer and an encapsulation layer 232. Additionally, a sensor 234 is provided at the sample manipulation surface. The sensor may be, for example, a sensor sensitive to detect SAWs. Alternatively, the sensor may be a thermal sensor (e.g. to determine temperature). Alternatively, the sensor may be a conductivity (or impedance) sensor. In particular, a conductivity sensor may be of use to determine the presence or absence of a (conducting) fluid sample in the channel 230. Alternatively the sensor may be an electrochemical sensor, such as a sensor adapted to sense a predetermined electrochemical reaction, or a pH sensor.

In other embodiments, sensor 234 may be replaced by an actuator. Suitable actuators include heaters. In one embodiment, a heater may be formed by a transducer operating to generate SAWs which are subsequently dissipated in the apparatus as heat. In another embodiment, a heater may be provided as a resistive heating element. Further detail about the incorporation of heaters (in the context of PCR) is set out below.

Figure 36:
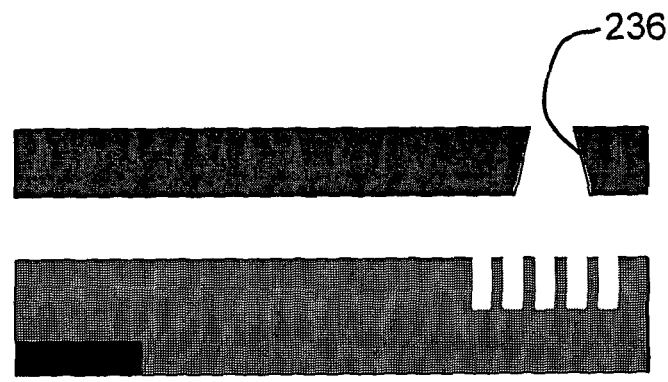

FIG. 36 illustrates an alternative nebulisation apparatus. Nozzle 236 is formed in encapsulation layer 232 and is located in register with the arrangement of SAW scattering elements. In operation, a fluid sample is nebulised by the apparatus and is allowed to leave the apparatus via nozzle 236.

Figure 37:
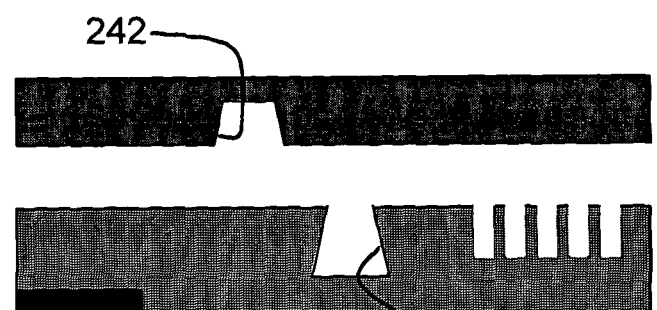

FIG. 37 illustrates a modification of the apparatus of FIG. 35, in which the piezoelectric layer has a chamber 240 formed in it and the encapsulation layer has a chamber 242 formed in it. Reagents can be stored in these chambers, for use during operation of the device, e.g. to carry out an assay.

In further embodiments, the sample manipulation surface may be modified in order to provide binding sites for biological molecules or species of interest (e.g. DNA, RNA, antibodies, etc.).

In each of the embodiments discussed above, the arrangement of SAW scattering elements comprises a periodic array of (substantially) point defects for scattering of the SAWs.

The present inventors consider that a similar effect can be obtained by using a ridge, channel (or more generally, linear step) in the sample manipulation surface in order to provide useful effects in terms of SAW distribution. For example, a superstrate may be provided with ridges forming a cone shape, in order to control a droplet, in place of the periodic array of cavity-based SAW scattering elements.

The material for the piezoelectric layer (or other SAW generating material layer) may be selected from the group consisting of $LiNbO_3$, PZT, $BaTiO_3$, $SbTiO_3$, ZnO, $SiO_2$, AlN, $LiTaO_3$, $Al_2O_3$ GaAs, SiC and polyvinylidene fluoride (PVDF). Of these, of $LiNbO_3$ or ZnO are particularly preferred.

In order to form the fluidics apparatus in a manner compatible with relatively low cost mass processing, it is necessary to consider the use of piezoelectric material layers that are not in the form of a single crystal. The growth of bulk single crystals is expensive and the formation of epitaxial thin films generally requires the use of a single crystal substrate (also expensive). Epitaxial growth is also typically relatively slow.

Therefore it is preferred to form the piezoelectric layer using a deposition process selected from the group consisting of: sputtering, screen printing, casting, doctor blading, dip-coating, solution deposition and electrophoresis. Additionally, it is possible to deposit by printing an ink comprising piezoelectric material particles held in a fluid suspension.

Other authors have produced a review of the formation of ZnO films for use in SAW-based biological sensors, in Fu et al (2010) [Y. Q. Fu et al "Recent developments on ZnO films for acoustic wave bio-sensing and microfluidics applications: a review" Sensors and Actuators B: Chemical 143 (2010) 606-619]. In that paper, the content of which is incorporated herein by reference in its entirety, there is a discussion of the deposition of polycrystalline films of ZnO using rf magnetron sputtering. Sputtering can be carried out at relatively low temperature (significantly less than 200° C.). Depending on the conditions, it is shown that the ZnO film can form a polycrystalline, amorphous, nanocrystalline or microcrystalline microstructure. Furthermore, textured polycrystalline films are shown to be possible. Based on this, the skilled person is able to manufacture suitable piezoelectric layers from different piezoelectric materials on suitable substrates according to the specific purpose to which the fluidics apparatus will be put.

It is not necessary to use only piezoelectric materials for the SAW generation material layer. There are a number of approaches for the generation of ultrasonics that will be known to the skilled person, for example using piezoelectric, electromagnetic or magnetostrictive transducers. Such transducers can operate into the GHz regime. For example, it is known to form a magnetostrictive SAW device, as discussed in G. Scheerschmidt et al (2010) [G. Scheerschmidt et al "Resonance modes of magnetically generated surface waves in acoustic wave guide systems" Journal of Magnetism and Magnetic Materials 322 (2010) 1628-1630], the content of which is incorporated herein by reference in its entirety.

Figure 38:
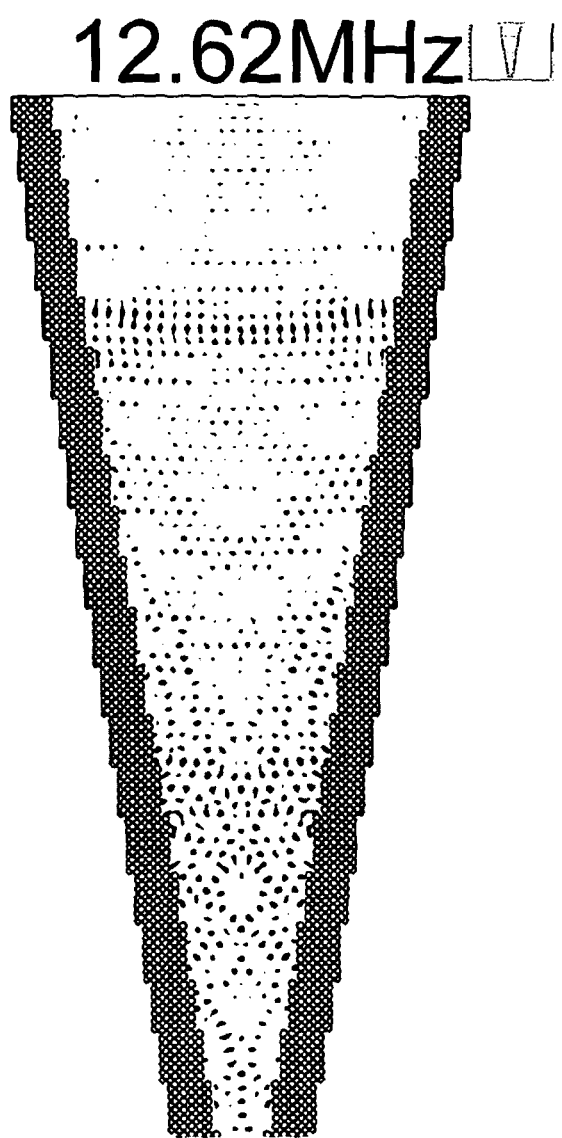
Figure 39:
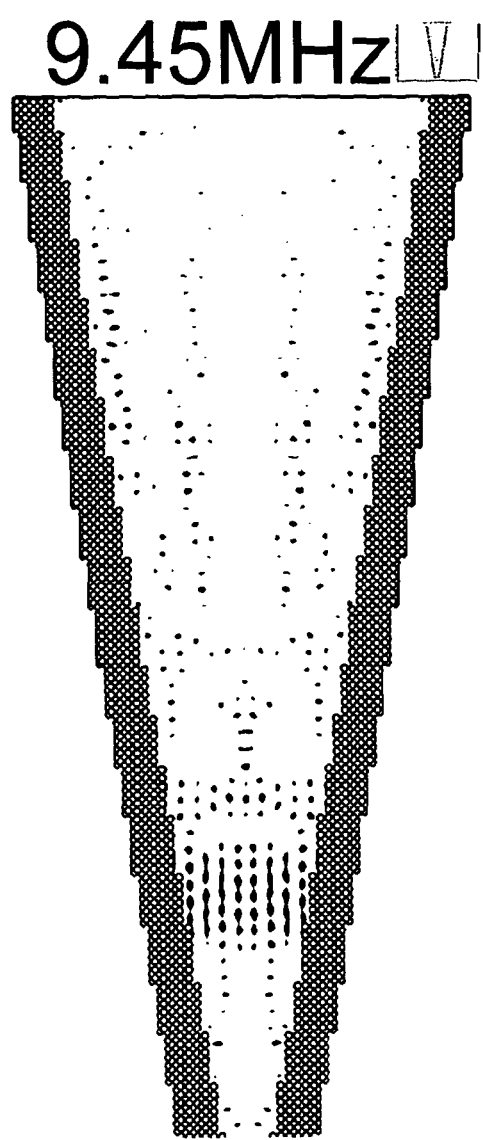

FIGS. 38 and 39 illustrate the effect of SAW frequency on the mode of operation of the apparatus. In FIG. 38, a phononic array is modelled at a SAW frequency of 12.62 MHz. The effect of this is to set up a particular distribution of SAWs at the sample manipulation surface. In FIG. 39, the same phononic array is modelled at a SAW frequency of 9.45 MHz. The effect of this is to set up a different distribution of SAWs at the sample manipulation surface.

Temperature Control

In a further embodiment, the present invention is of interest for carrying out assays or reactions that require changes in temperature, and in particular which require thermal cycling.

Point-of-care (POC) diagnosis often relies on analysing nucleic acids in biological samples, for the detection of specific diseases such as influenza or chlamydia. Despite the increase in sensitivity in newly developed sensors, there is still a need to amplify the molecules of interest before detection to achieve significant signal-to-noise ratios. The method of choice remains polymerase chain reaction (PCR) and its numerous variants, which rely on cycling temperatures to activate biological enzymes. To perform a PCR, the sample is mixed with enzymes that replicate DNA molecules (polymerase) based on a template, which is made of the sample and added primer short DNA sequences, using nucleotides added to the reaction mixture. Some variants, such as isothermal PCR (Loop-Mediated Isothermal PCR, LAMP for example) do not require cycling, but a constant temperature.

Other steps of a POC assay may require heating when specific biological reactions are taking place. For example cells from the patient, such as T lymphocytes, can be cultured in a heated reactor (37° C.) to express cytokines that are detected as a biomarker of Tuberculosis latent infection [Quantiferon kit, Cellestis, Australia].

Lab-on-chip (LOC) systems have been developed to perform temperature cycling or heating, usually based on metal heaters on the surface of a microchip [Neuzil P. et al, Mol. BioSyst., 2006, 2, 292-298]. In addition to bringing rigid design constraints, as their location is fixed, these heaters require a supplementary electrical connection and power supply, which is a challenging matter for battery-operated POC systems.

It is well known that piezoelectric transducers used to generate the SAWs, or any material that the waves travel through, heat up due to mechanical losses by the vibrations. Actually, a lot of effort in this field is devoted to reducing this heat to prevent early device failure. This phenomenon has been used to heat up water droplets [Kondoh J. et al., IEEE transactions on ultrasonics, ferroelectrics, and frequency control, 52, 2005 1881-1883] with the intent of performing PCR [Kondoh J. et al, Sensors and Actuators A 149 (2009) 292-297].

The present inventors find that heat can be controlled on a mass-fabricated structure (or indeed on a superstrate) using the power applied to the excitation of the SAW. The heat generated by the SAW is dissipated through a heat sink to cool down the sample and thus provides a means to cycle temperature. Phononic structures, with the capability to shape the acoustic energy, can be used to control the heating of a sample using the excitation frequency as a switch between different functions. The acoustic energy can be channelled toward a heating element for one frequency, but used for other microfluidic functions, with less heat, at other frequencies.

This capability constitutes yet another module into the microfluidic functions that can be performed using SAW, which facilitates the integration of an entire biological assay, from sample preparation, amplification and detection, on a single platform.

The inventors carried out tests based on superstrates and single crystal LiNbO$_3$, although the concept applies similarly to the use of piezoelectric layers in the form of polycrystalline films with the sample manipulation surface being the surface of the piezoelectric layer. The superstrate is coupled with gel to the IDT surface, which is positioned on a heat sink.

As the power is ramped up in the device, the temperature of the superstrate increases, as well as that of the samples. In one example, heating of two 10 μl mineral oil droplets on a silicon superstrate was investigated. The power used here was −4 dBm at 19.13 MHz. The emissivity value used by the FLIR (Fluke) camera was 0.95.

Figure 40:
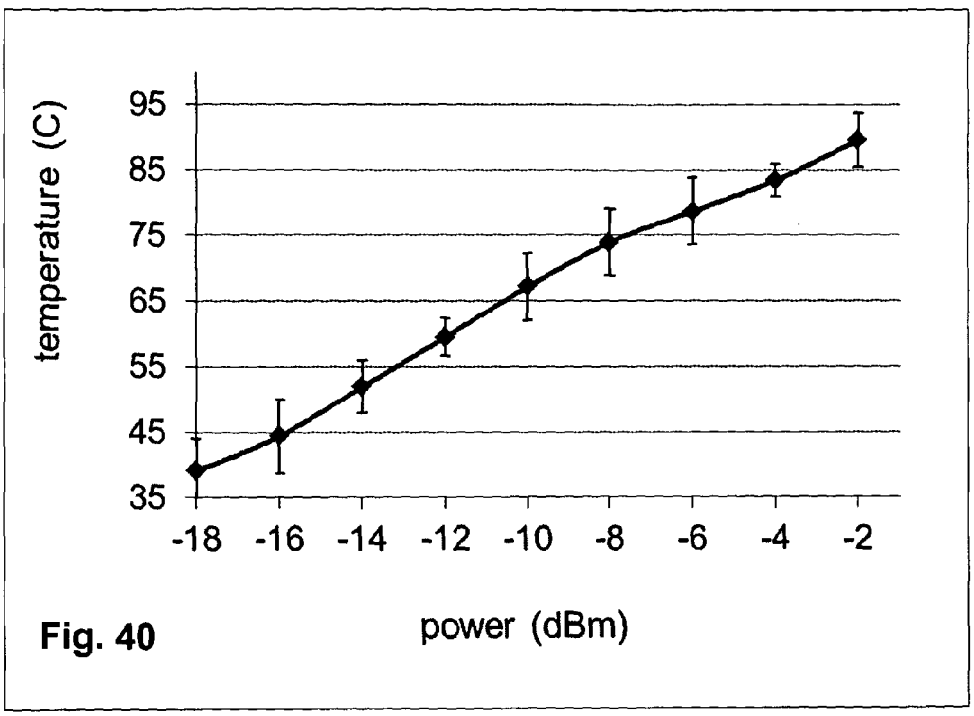

The temperature of the sample is linked to the power of the excitation signal, as shown by FIG. 40, The results plotted in FIG. 40 are for heating of a 10 μl water droplet on a silicon superstrate at 9.77 MHz. The temperature was observed with an IR camera.

Figure 41:
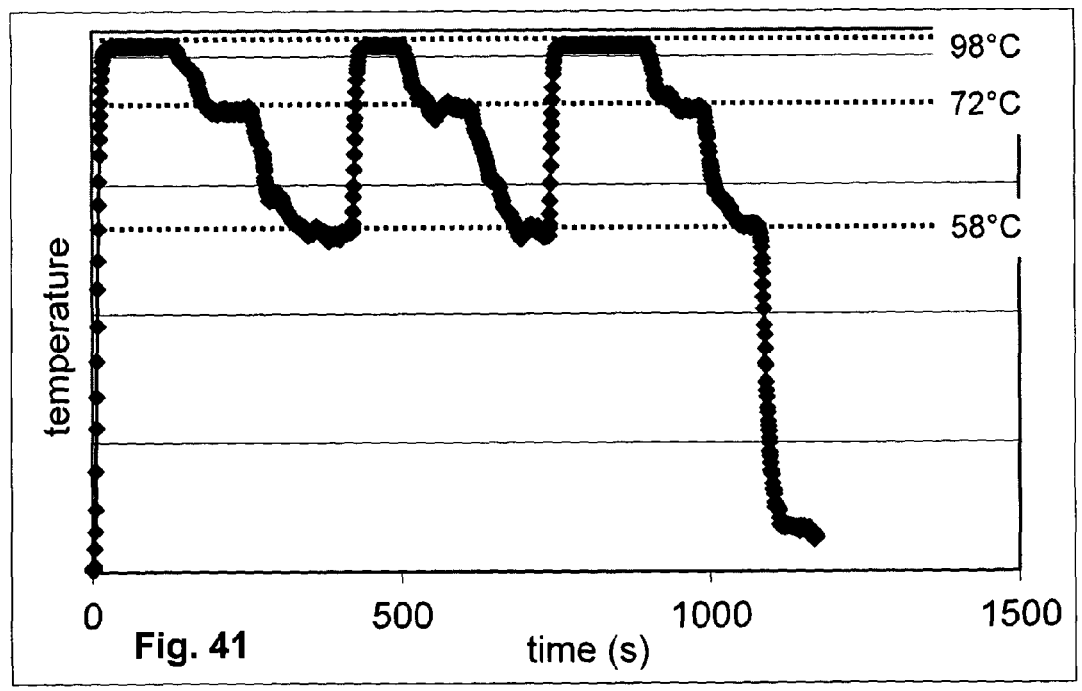

Using the power as a handle to control the temperature, temperature cycling can be achieved. FIG. 41 shows temperature cycling of a 1 μl water droplet encapsulated in 10 μl of oil on a silicon superstrate to avoid evaporation. The temperatures of the water drop in the cycles are 98, 72 and 58° C.

The heating of materials with acoustic waves depends on the way these absorb the energy from the deformations. Soft materials (low Young's modulus) should absorb more than harder ones, which translates into more heat. Relying on the heat conduction of the manipulation surface, this increased heat diffuses to a sample placed nearby.

Figure 42:
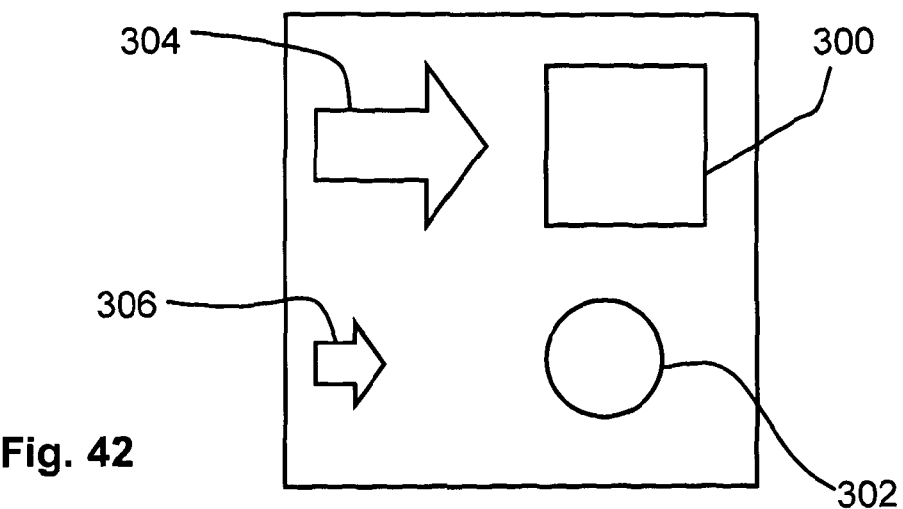
Figure 43:
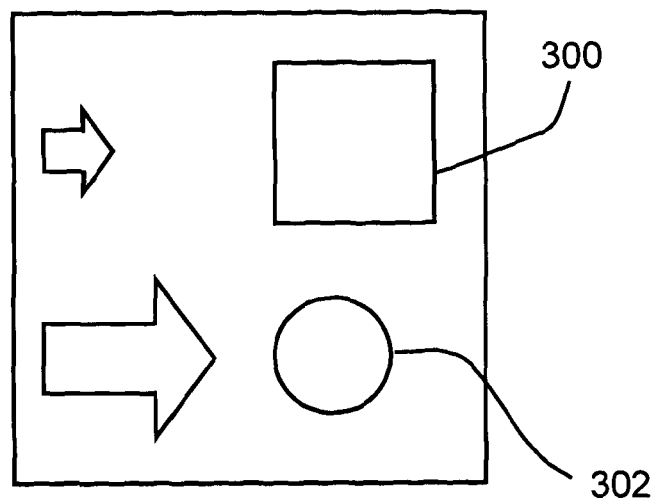

Using the phononic structures, it is then possible to shield the soft material area from the waves to reduce heat at some excitation frequencies, while the waves can be focussed on that area at other frequencies, increasing the temperature. This provides a switch between an improved heating function and other microfluidic functions, for which heat may not be desirable (movement, centrifugation). This principle is illustrated in FIGS. 42 and 43, which show frequency dependant heating via an absorbing area 300. At frequency f$_1$ (FIG. 42) the acoustic wave is propagated mainly towards the sample 302, while at frequency f$_2$ (FIG. 43), it is propagated towards the absorbing area, resulting in increased temperature. Suitable means for providing different SAW intensities (indicated by the size of arrows 304, 306 in FIG. 42) are explained below.

As will be understood, the apparatus preferably includes a temperature sensor to enable directed control of the generation of SAWs in order to control the temperature.

The spatial distribution of the acoustic energy can be easily controlled using either a slanted IDT or various phononic configurations as detailed in FIGS. 44-50, in order to provide frequency-dependant heating.

Figure 44:
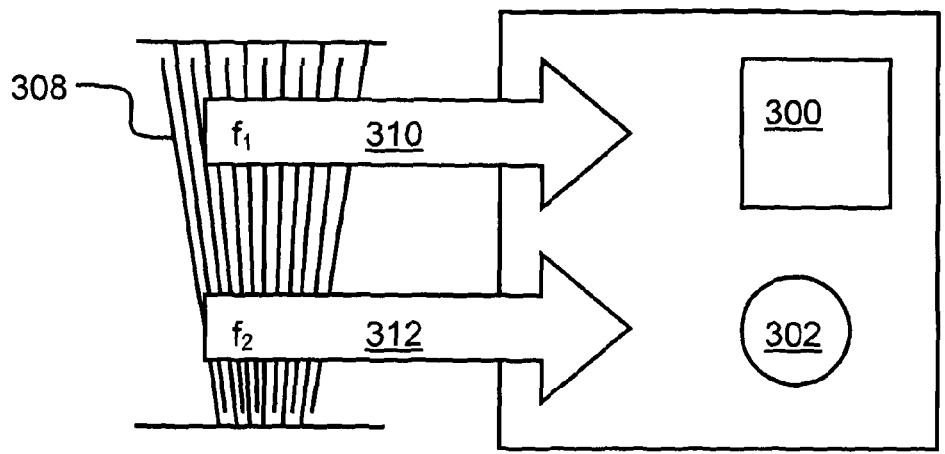

In FIG. 44, using a slanted IDT 308, the aperture of the SAW can be localised where the finger spacing supports the resonance at a particular frequency. Here frequency f$_1$ (SAW train 310) is used to heat the absorbing material 300, while frequency f$_2$ (SAW train 312) is used to activate the sample 302. Here, f$_1$<f$_2$.

Figure 45:
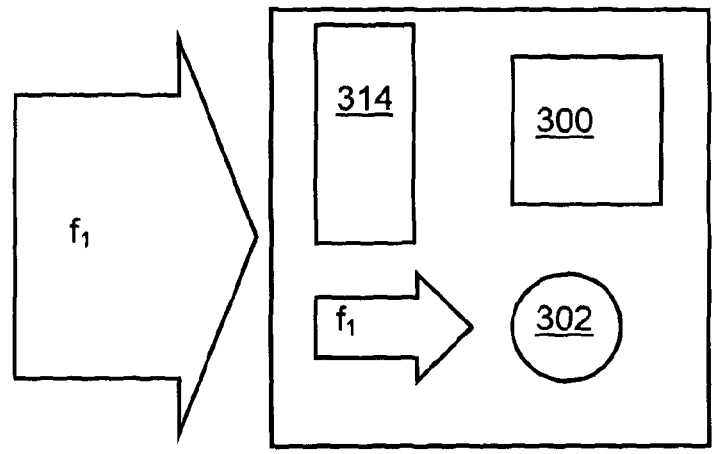
Figure 46:
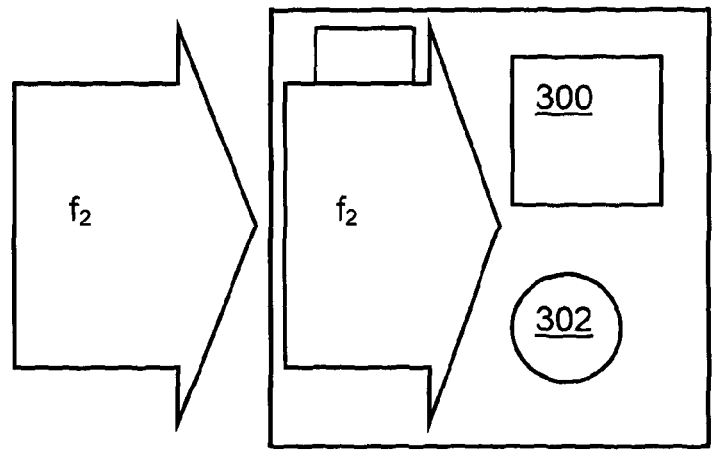

In FIG. 45, phononic filter 314 can filter out the waves propagating at frequency f$_1$, resulting in limited heating by reducing the amplitude of SAWs that can reach the heat absorbing material 300, but sample activation, while heating can be promoted for frequency f$_2$, outside of the filter bandgap as shown in FIG. 46. This configuration has the advantage of activating the sample in both configurations, which could promote mixing during heating.

Figure 47:
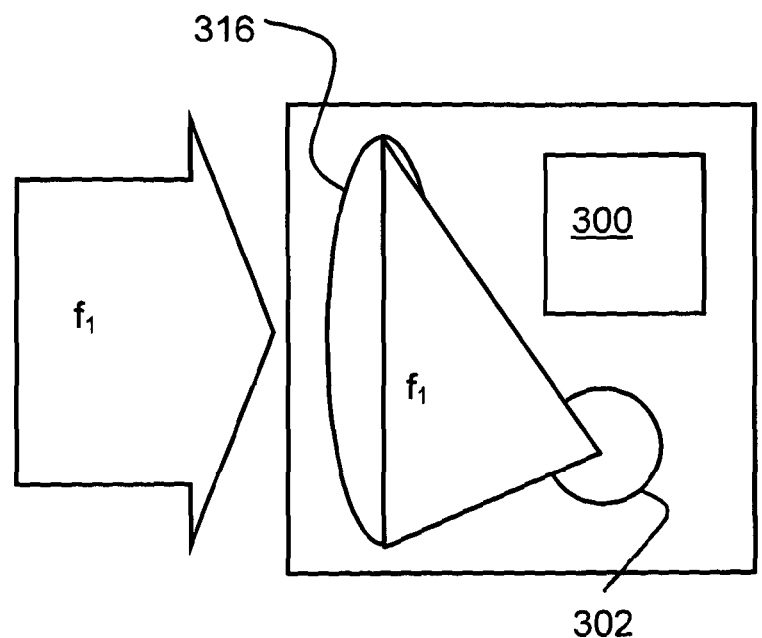
Figure 48:
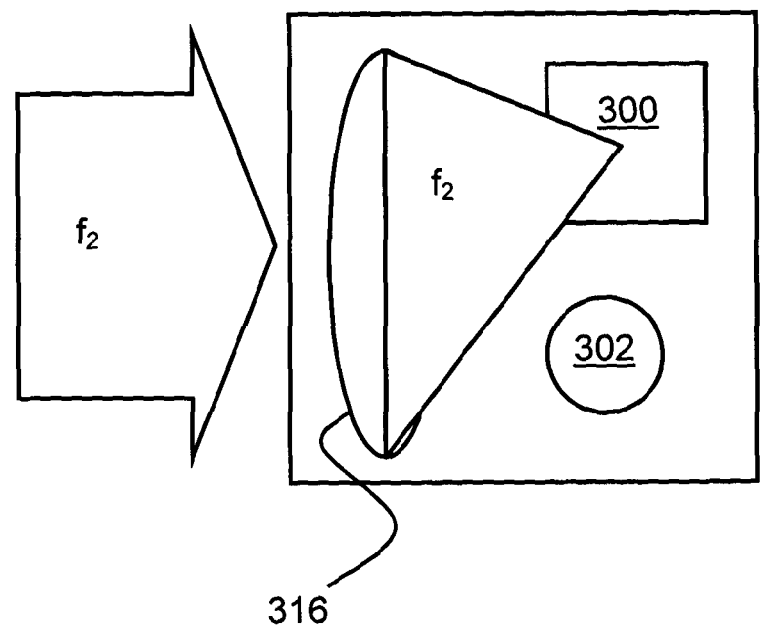

In FIGS. 47 and 48, a phononic lens 316 focuses the acoustic wave at different positions for different frequencies f$_1$ and f$_2$. The focussing effect increases heating further.

Figure 49:
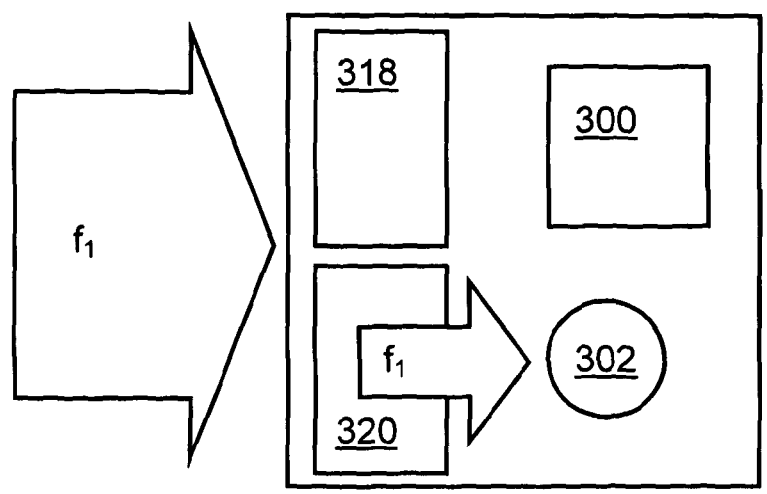
Figure 50:
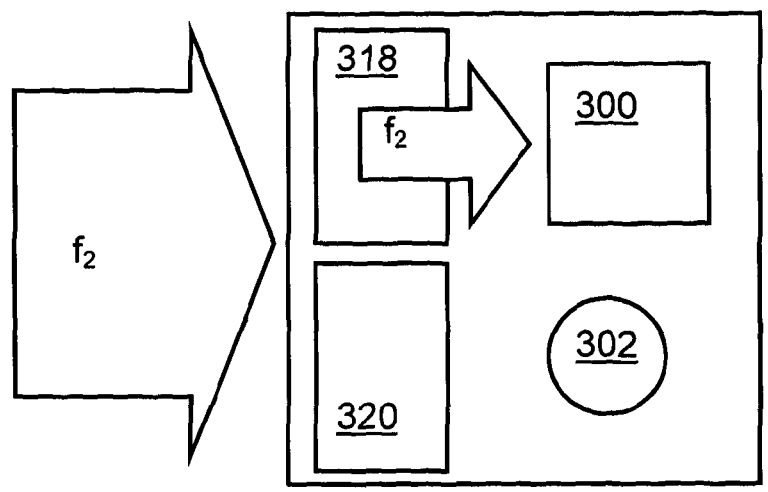

In FIGS. 49 and 50, to prevent the activation of the sample 302 during heating (for example for cell culture), a double filter configuration can be used, in which first filter 318 allows transmission of SAWs of frequency f$_2$ but blocks SAWs of frequency f$_1$ and second filter 320 allows transmission of SAWs of frequency f$_1$ but blocks SAWs of frequency f$_2$.

The phononic crystal structure itself can be used as a specific absorbing structure. When the excitation frequency is chosen in the band gap of the phononic structure, the waves can be scattered within it. When the phononic structure is made in an absorbent material (soft), then this scattering results in increased heating, as compared to the use of a frequency outside the bandgap. Such a phononic structure can be formed using plastics pillars (PDMS, polystyrene) or holes filled with soft material in a more rigid matrix (PDMS in silicon for example).

Solid Sample Processing

Although common diagnostic assays are performed on analytes in bodily fluids, such as blood or urine, due to their accessibility, there is also significant interest in detecting analytes in solid samples. These include biopsies of tumours in various cancers, or faeces, where the presence of blood can be a biomarker for bowel cancer for example. These solid samples are challenging to process, especially in point-of-care assays that often rely on microfluidics, since the solid samples need to be disrupted. Other methodologies relying on direct measurements are limited by the fact that these samples are highly heterogeneous, so that multiple sampling in different locations would be needed to avoid a high rate of false positive results.

The common means of disrupting solid samples often rely on mechanically crushing them in a liquid matrix, using shear forces from a liquid flow, adding beads, or applying very high pressure gradients. Another method uses acoustic energy in the ultrasonic range to disrupt the tissue and cells, by inducing cavitation [Timothy L. Hall et al., IEEE transactions on ultrasonics, ferroelectrics, and frequency control, 54, 2007, 569-575] or using acoustic streaming coupled with beads. However, most of these techniques have to be performed off-chip, limiting their application in POC setting.

In another embodiment of the invention, SAWs are used to combine streaming with mechanical vibrations to detect analytes in solid (or substantially solid) samples such as tissues. This has the advantage of rapidly homogenising the sample to increase the confidence in the results of the diagnostic test, and can be readily integrated with other microfluidic functions.

In addition to providing mechanical vibrations of the support and the tissue placed on its surface, resulting in shear and pressure stresses, SAW provides acoustic streaming in the liquid matrix of the sample, enhancing the release of the analyte in the liquid phase for detection. This method can be cavitation-free, and thus gentler for the biomolecules of interest that could be denatured by traditional ultrasonic techniques, and does not need additional supports such as beads that may need to be separated for further analysis.

Phononic structures can be used to focus the acoustic energy into specific areas of the device to enhance processing, as previously described. They can also be used as a solid support to increase shear stresses, in a similar fashion as a filter or beads. For example, phononic arrays of pillars in the centre of a channel or phononic arrays of holes in a surface can be used.

Composite SAW Generation Material Layer

It is possible for the material of the SAW generation material layer to be in the form of a composite. In one embodiment, piezoelectric particles are dispersed in a polymer matrix to form a composite material. The composite material is then subjected to poling (the application of a high electric field) in order to orient the piezoelectric particles. Subsequently, the application of an electric field results in deformation of the piezoelectric particles, leading to deformation of the composite material as a whole. Application of the electric field at a suitable frequency then leads to the deformation propagating as a wave (e.g. SAW).

A suitable protocol for manufacturing an example composite material is as follows.

Protocol for Manufacturing an Example Composite Material

Materials: PZT powder (PZ26 Ferroperm, particle size about 500 nm), SU-8-50 Photoresist, IGEPAL CA630 (dispersant, Aldrich), propylene glycol methyl ether acetate (PGMEA).

Target Compositions: Volume fraction of solids in dispersion 40% calculated as (PZT+SU8)/(PZT+SU8+PGMEA). Volume fraction of PZT in final film 40% calculated as PZT/(PZT+SU8)

Mixing Method:
1. Add PZT, IGEPAL (1% wt relative to PZT), and excess PGMEA.
2. Use Silverson mixer (8000 rpm for 7 mins) to break up agglomerates and aid dispersion.
3. Centrifuge 2500 rpm for 4 mins.
4. Remove excess PGMEA by controlled decant.
5. Add required SU8-50.
6. Manual shake and ultrasonicate sample (30 mins) to aid distribution of powder within viscous SU8-50.
7. Prior to casting allow dispersion to stand to allow any bubbles to escape.

Casting Method:
1. The flexible substrates are secured to a support glass slide using polyimide tape to help hold them level.
2. Two parallel strips of a low adhesion Nitto tape (80 micrometer thick) are then applied to the substrate to mark out the area for the casting and to provide an effective casting height for the "spreading edge".
3. This set-up is then $O_2$/Ar plasma etched for 3 mins at 20 W. (Note: even substrates supplied previously plasma etched required this additional treatment prior to casting otherwise the dispersion would not wet the substrate).
4. Two to three drops of the dispersion are applied to the substrate between the Nitto tape, and the edge of a clean glass slide is used as the spreading edge to cast the initial 80 micron wet film.
5. Partially dry film for 2 mins at 95° C. on hot plate, peel off Nitto tape, then dry in oven at 95° C. for 20 mins.

UV Cure:
1. Dried film is flood exposed for 7 mins (12 mW/cm$^2$) on UV mask aligner.
2. Post Bake sample 15 mins in oven at 95° C.

A typical dry cured film thickness achieved by this casting approach is about 14 micrometer.

Corona Poling Method:
Pin height from substrate: about 25 mm.
Applied voltage for audible/visual discharge: about 15 KV.
Field applied at about 105-110° C.
Field removed <65° C. (cooling time about 30 mins)

It should be noted that this manufacturing methodology can be easily handled via a reel-to-reel process, leading to a very cost-effective fabrication. This cost-effectiveness allows the whole device to be used as a disposable item.

Structure and Testing

Each sample reported here used an 8 μm layer of PZT loaded SU-8 (40% by volume) on an IDT with an interdigitated finger width and spacing of 60 μm, patterned using reel-to-reel processes. In a first device, the substrate was a thin sheet of PET. In a second device, the substrate was a 5 mm thick piece of PMMA. In these devices, the electrodes were sandwiched between the substrate and the SAW generation material layer.

Each device had a fundamental resonance at about 30 MHz when the $S_{11}$ parameter was measured using a vector network analyser (Figure below). The longitudinal speed of sound for SU-8 from is about 2880 m/s, although this will depends to some extent on the processing route, as the SU-8 can have a variable degree of cross-linking. This value can decrease with mineral loading at much higher frequencies. The longitudinal speed of sound for PZT is about 4300 m/s. Using a simple rule of mixtures, the longitudinal speed of sound for the composite is about 3400 m/s, which is in the range of the calculated value of about 3600 m/s from the $S_{11}$ measurement.

In the testing of these devices it was uncertain whether SAWs were being generated but transduction was clearly present. The PMMA sample showed the greater electrical drop at about 45 MHz and this is attributed to both the excitation of another mode (possibly a Sezawa mode) with an impedance closer to 50Ω and/or the greater mechanical rigidity of that substrate due to its thickness relative to the PET-based device, as the mechanical properties of PET and PMMA are very similar.

The PZT/SU-8 material was prone to dielectric heating, as were IDT's on PET with no piezoelectric material present. It was noted that the PZT/SU-8 samples would last longer, probably due to the layer acting as a heat sink. Using a Fluke IR camera, it was very apparent that heating can be easily induced into the material, and more surprisingly in a very localised manner. Applying a power of about 0.1 W at 30 MHz to the interdigitated electrodes reveals very localised heating above the interdigitated electrodes, giving rise to a temperature of about 77° C. in under 5 s. Over the electrode area, there was a variation in temperature of over 20° C.

The amount of heating was proportional to the amount of power applied to the devices. Some heating of the PZT/SU-8 was beneficial as the longer these samples were used, the greater the actuation was observed for a 5 μl droplet placed on the surface of the active material. SAWs and subsequent streaming were observed, based on an observed line of concentration of silver coated 1 micrometer glass beads suspended in solution. It is clear that PCR is an attractive application for such a disposable device platform.

Polymer Phononic Structure Layer

Devices have been fabricated and tested where the phononic crystal is a patterned layer of SU-8 on glass, with a square lattice array of either holes or pillars. A gap in the SU-8 layer is provided in order to couple (via an adhesive layer) to the glass substrate a $LiNbO_3$ single crystal transducer with a interdigitated electrode structure formed on its upper surface.

The glass substrate was of thickness about 1.5 mm, the $LiNbO_3$ single crystal transducer was of thickness about 500 micrometer and the SU-8 layer was of thickness about 100 micrometer.

Firstly, a device having a phononic structure in the form of holes through the SU-8 layer was characterised using a vibrometer (Polytec GmbH). A relatively large spacing was provided for the interdigitated electrodes, to allow the induced surface mechanical wave in the $LiNbO_3$ to extend down to the bottom face of the material. In this device, the amount of mechanical actuation on the opposite surface to where the excitation electrodes are placed is less than half, there is still enough mechanical vibration available to do some work. Optimisation of the coupling can be carried out to increase the efficiency of transference of the acoustic waves from the $LiNbO_3$ to the glass, as there appears to be a 50% insertion loss between the transducer and substrate, which shows itself as localised heating of the contact area. The vibrometer data suggests that, once coupled, the transfer of acoustic energy into the SU-8 layer is relatively efficient.

The vibrometer measures the surface displacement at various positions on the device. The measurements reveal that there is an increase in the surface displacement at the SU-8 surface close to the opening formed in the SU-8 in order to accommodate the transducer. This is attributed to bunching caused by the slower velocity of sound in SU-8 relative to glass. However, further away from the opening, this increase quickly dies down to the same level as that observed for the glass.

Figure 51:
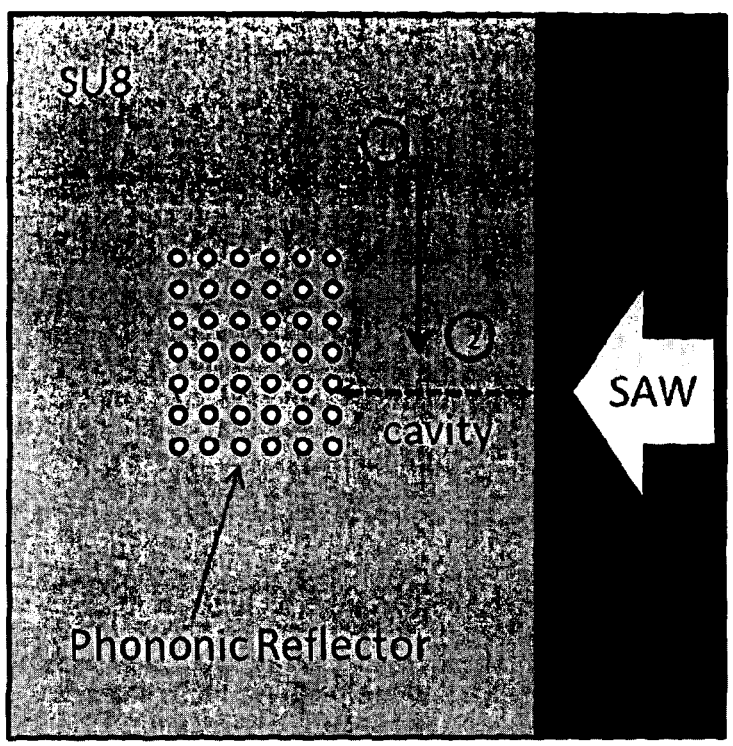
Figure 52:
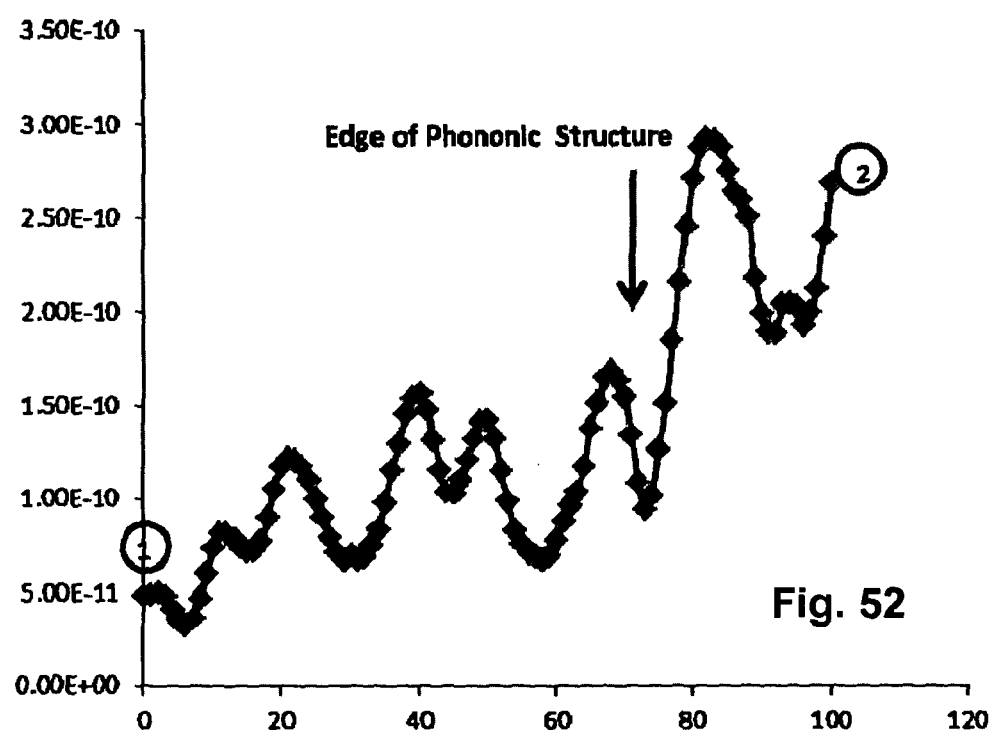

Scanning parallel to the edge of the opening, a marked increase in the amplitude of the displacement was observed between the phononic lattice and the SU-8/glass interface. The phononic lattice and the SU-8/glass interface act as reflectors, creating a cavity, where the surface displacement caused by the amplitude of the partial standing waves increase relative to the incoming coupled SAWs from the transducer. This is illustrated by FIG. 51, which shows a schematic plan view of the SU-8 layer and the edge of the opening in which the transducer (not shown) is located. FIG. 52 shows the results of a vibrometer scan along the line between positions 1 and 2 on the SU-8 surface. The plot shows the measured vertical displacements (y-axis—arbitrary units) with distance x-axis—arbitraty units). At position 1, the SAWs do not encounter the phononic reflector. However, at position 2, the SAWs encounter the phononic reflector and so a cavity is formed. Thus the phononic structure influences the propagation of the SAWs on the SU-8 layer, because a significant increase in the out of plane displacement is measured in the cavity (position 2) compared with outside the cavity (position 1).

Figure 53:
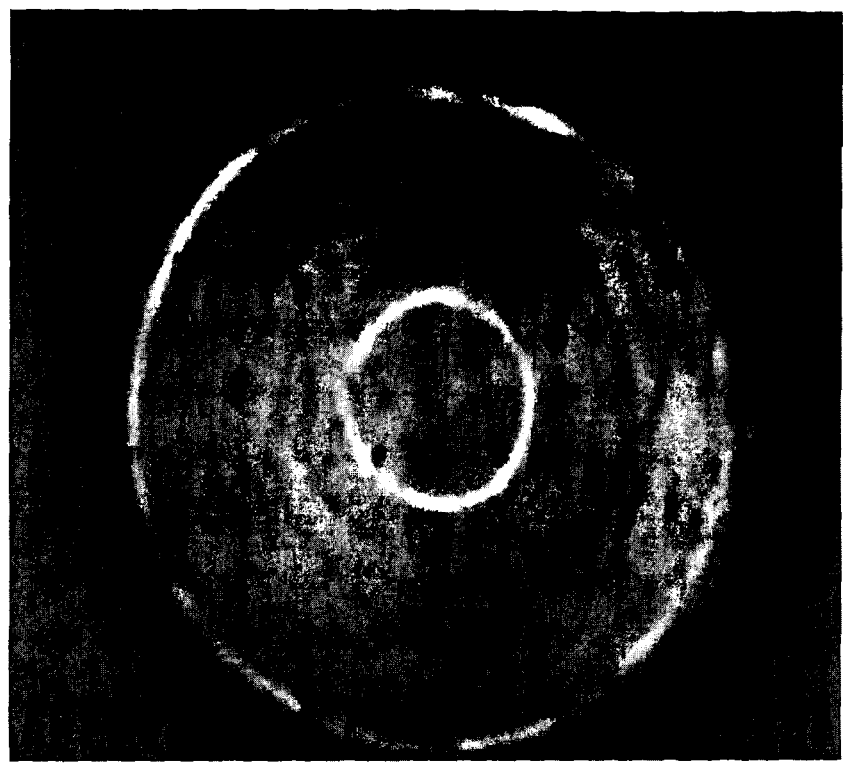

When a drop of water containing 1 micrometer glass beads is positioned within the cavity illustrated in FIG. 53, the beads align in concentric rings due to the standing waves created. FIG. 53 shows this effect in a 5 microliter water drop actuated with SAWs at 6.5 MHz at 1.6 W applied power.

Next, a superstrate was fabricated formed of glass having a phononic structure of SU-8 pillars formed on the upper surface of the glass.

Figure 54:
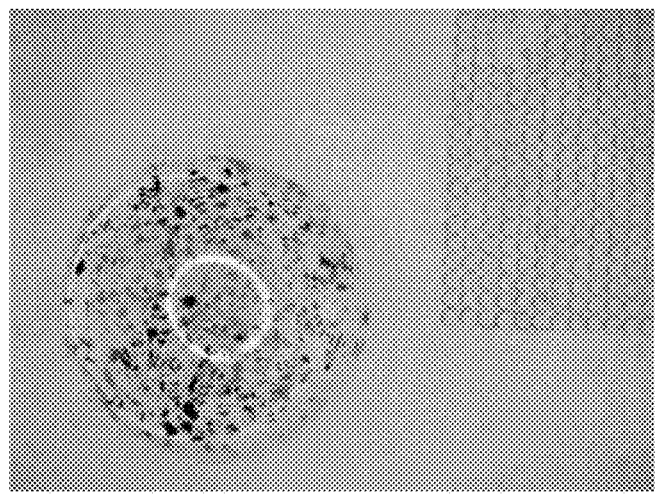
Figure 55:
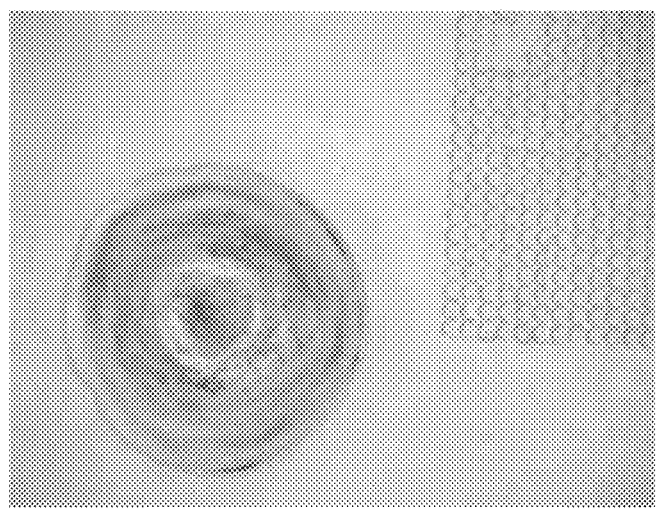
Figure 56:
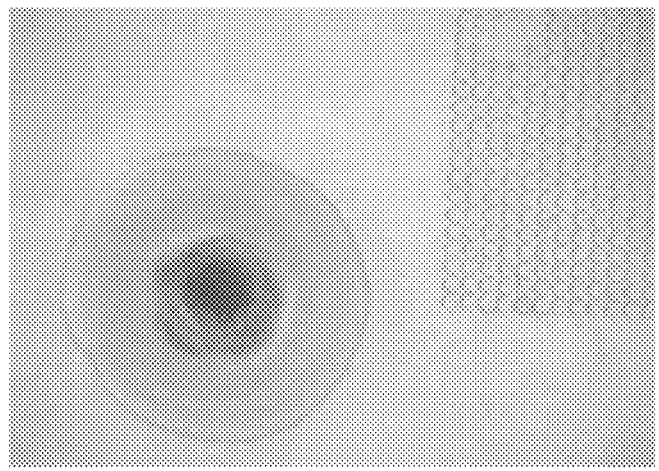

Using this system, it is shown that 1 micrometer glass beads can be centrifuged in the centre of a 5 microliter water drop positioned at the edge of the phononic lattice. FIGS. 54, 55 and 56 show sequential microscopic images of the glass beads in the water drop actuated with an excitation signal at 10.4 MHz with about 1.26 W applied, the SAWs being applied from the right side of each image. The SAWs are filtered by the phononic SU-8 pillars lattice, driving rotational flows resulting in centrifugation, with the particles ultimately becoming concentrated at the centre of the drop, as shown in FIG. 56.

This work demonstrates microfluidic actuation using SAWs that are phononically shaped by a SU-8 phononic structure formed on a glass superstrate. This device therefore forms the basis of a low-cost diagnostic device incorporating a particle concentration stage. The device can be formed at low cost because glass can be processed cheaply, compared with the processing of $LiNbO_3$ or other piezoelectric materials.

Prior patent applications and prior publications referred to in this disclosure are hereby incorporated herein by reference in their entirety.

The preferred embodiments of the invention have been described by way of example. Modifications of these embodiments, further embodiments and modifications thereof will be apparent to the skilled person on reading this disclosure and as such are within the scope of the present invention.

ABBREVIATIONS

ATP Adenosine triphosphate
ADP Adenosine diphosphate
cAMP Cyclic adenosine monoposphate
ELISA Enzyme-linked immunosorbent assay
IDT Interdigitated transducer (also known as an interdigital transducer)
PBS Phosphate buffered saline
PCR Polymerase chain reaction
SAW Surface acoustic wave

The invention claimed is:

1. A fluidics apparatus for manipulation of at least one fluid sample, the apparatus including: a manipulation surface for location of the fluid sample; a surface acoustic wave (SAW) generation material layer, wherein either: the material of the SAW generation material layer is selected from the group consisting of: polycrystalline material, textured polycrystalline material, biaxially textured polycrystalline material, microcrystalline material, nanocrystalline material, amorphous material and composite material, or the SAW generation material layer is not in the form of a single crystal layer; and a transducer electrode structure arranged at the SAW generation material layer to provide SAWs at the manipulation surface for interaction with the fluid sample, wherein the manipulation surface comprises a plurality of surface acoustic wave (SAW) scattering elements for affecting the transmission, distribution and/or behaviour of SAWs at the manipulation surface, said plurality of surface acoustic wave (SAW) scattering elements comprising a two dimensional periodic arrangement, and wherein the plurality of SAW scattering elements extends at least partially into the SAW generation material layer and intersects with the surface of the SAW generation material layer.

2. The fluidics apparatus according to claim 1 wherein the SAW generation material layer is formed from a ferroelectric material, pyroelectric material, piezoelectric material or magnetostrictive material.

3. The fluidics apparatus according to claim 1 wherein the transducer electrode structure is at least partially embedded in the SAW generation material layer.

4. The fluidics apparatus according to claim 1 wherein the transducer is tunable, such that the lateral position of a SAW emission train is movable.

5. The fluidics apparatus according to claim 1 wherein the manipulation surface is a surface of the SAW generation material layer, optionally covered with a surface-passivation film.

6. The fluidics apparatus according to claim 1 wherein at least one additional SAW scattering element is provided, said additional SAW scattering element including a linearly extending change in the profile of the manipulation surface.

7. The fluidics apparatus according to claim 1 wherein the apparatus includes at least one enclosed channel for the fluid sample, the channel being bounded on at least one side by the manipulation surface.

8. The fluidics apparatus according to claim 7 wherein the opposing side of the channel is bounded by a passive encapsulation surface.

9. The fluidics apparatus according to claim 7 wherein two or more sides of the channel may be bounded by a manipulation surface, each manipulation surface being adapted to be provided with SAWs for interaction with the fluid sample in the channel, and wherein each manipulation surface optionally has at least one SAW scattering element for affecting the transmission, distribution and/or behaviour of SAWs at the manipulation surface.

10. The fluidics apparatus according claim 1 having:
- a first SAW generation material layer and associated transducer electrode structure;
- a first manipulation surface at which SAWs are provided from the first SAW generation material layer;
- a second SAW generation material layer and associated transducer electrode structure; and
- a second manipulation surface at which SAWs are provided from the second SAW generation material layer, wherein the first and second manipulation surfaces define between them a channel for the fluid sample.

11. The fluidics apparatus according to claim 1 wherein the apparatus further includes at least one reservoir.

12. The fluidics apparatus according to claim 1 wherein the apparatus further includes at least one aperture.

13. A method of using a fluidics apparatus to manipulate at least one fluid sample comprising: providing a fluidics apparatus comprising: a manipulation surface at which the fluid sample is located; a surface acoustic wave (SAW) generation material layer, wherein either: the material of the SAW generation material layer is selected from the group consisting of: polycrystalline material, textured polycrystalline material, biaxially textured polycrystalline material, microcrystalline material, nanocrystalline material, amorphous material and composite material, or the SAW generation material layer is not in the form of a single crystal layer, a transducer electrode structure arranged at the SAW generation material layer; wherein the apparatus is operated to provide SAWs at the manipulation surface for interaction with the fluid sample, and wherein the manipulation surface comprises a plurality of surface acoustic wave (SAW) scattering elements for affecting the transmission, distribution and/or behaviour of SAWs at the manipulation surface, said plurality of surface acoustic wave (SAW) scattering elements comprising a two dimensional periodic arrangement, and wherein the plurality of SAW scattering elements extends at least partially into the SAW generation material layer and intersects with the surface of the SAW generation material layer; and manipulating the fluid sample with the apparatus.

14. The method of using a fluidics apparatus according to claim 13 wherein the manipulation of the fluid sample includes one or more of: movement of the sample along the sample manipulation zone; splitting of the sample; combining two or more samples; atomisation of the sample from the sample manipulation zone; heating of the sample; concentration of species in the sample; mixing of the sample; sorting fluid samples; sorting particles or cells within fluid samples.

* * * * *